United States Patent
Lurie

(10) Patent No.: US 12,144,777 B2
(45) Date of Patent: *Nov. 19, 2024

(54) METHODS AND SYSTEMS TO REDUCE BRAIN DAMAGE

(71) Applicant: Keith G. Lurie, Minneapolis, MN (US)

(72) Inventor: Keith G. Lurie, Minneapolis, MN (US)

(73) Assignee: Resuscitation Innovations LLC, Minneapolis, MN (US)

( * ) Notice: Subject to any disclaimer, the term of this patent is extended or adjusted under 35 U.S.C. 154(b) by 842 days.

This patent is subject to a terminal disclaimer.

(21) Appl. No.: 17/335,922

(22) Filed: Jun. 1, 2021

(65) Prior Publication Data
US 2021/0322264 A1    Oct. 21, 2021

Related U.S. Application Data

(63) Continuation-in-part of application No. 16/058,851, filed on Aug. 8, 2018, now Pat. No. 11,020,314, (Continued)

(51) Int. Cl.
*A61H 31/00* (2006.01)
*A61G 13/12* (2006.01)
*A61G 13/04* (2006.01)

(52) U.S. Cl.
CPC ......... *A61H 31/004* (2013.01); *A61G 13/121* (2013.01); *A61G 13/122* (2013.01); (Continued)

(58) Field of Classification Search
CPC .... A61H 31/00; A61H 31/004; A61H 31/008; A61H 1/0229; A61G 7/005
See application file for complete search history.

(56) References Cited

U.S. PATENT DOCUMENTS

| 1,995,583 A | 3/1935 | Sanderson |
| 2,566,351 A | 9/1951 | Meuler |

(Continued)

FOREIGN PATENT DOCUMENTS

| EP | 2308440 A2 | 4/2011 |
| EP | 2289477 A1 | 9/2014 |

(Continued)

OTHER PUBLICATIONS

U.S. Appl. No. 14/626,770, "Corrected Notice of Allowability", Jan. 4, 2019, 2 pages.

(Continued)

*Primary Examiner* — Justine R Yu
*Assistant Examiner* — Christopher E Miller
(74) *Attorney, Agent, or Firm* — Kilpatrick Townsend & Stockton LLP

(57) ABSTRACT

A method to improve neurologically-intact survival rates after cardiac arrest may include performing CPR on an individual in cardiac arrest while the individual is in a supine position in general alignment with a horizontal plane. The method may include elevating the individual's head, shoulders, and heart relative to the individual's lower body while the individual's lower body remains generally aligned with the horizontal plane to cause blood to actively drain venous blood from the brain to reduce intracranial pressure. The method may include performing chest compressions on the individual and actively decompressing the individual's chest while the individual's head, shoulders, and heart are elevated.

18 Claims, 27 Drawing Sheets

Related U.S. Application Data which is a continuation-in-part of application No. 15/986,466, filed on May 22, 2018, now Pat. No. 10,406,069, which is a continuation-in-part of application No. 15/850,827, filed on Dec. 21, 2017, now Pat. No. 10,667,987, which is a continuation-in-part of application No. 15/601,494, filed on May 22, 2017, now Pat. No. 10,350,137, which is a continuation-in-part of application No. 15/285,063, filed on Oct. 4, 2016, now Pat. No. 10,406,068, which is a continuation-in-part of application No. 15/160,492, filed on May 20, 2016, now Pat. No. 11,259,988, which is a continuation-in-part of application No. 15/133,967, filed on Apr. 20, 2016, now Pat. No. 9,801,782, which is a continuation-in-part of application No. 14/996,147, filed on Jan. 14, 2016, now Pat. No. 9,750,661, which is a continuation-in-part of application No. 14/935,262, filed on Nov. 6, 2015, now Pat. No. 9,707,152, said application No. 14/935,262 is a continuation-in-part of application No. 14/677,562, filed on Apr. 2, 2015, now Pat. No. 10,092,481, which is a continuation of application No. 14/626,770, filed on Feb. 19, 2015, now Pat. No. 10,245,209.

(60) Provisional application No. 62/542,394, filed on Aug. 8, 2017, provisional application No. 62/509,469, filed on May 22, 2017, provisional application No. 62/242,655, filed on Oct. 16, 2015, provisional application No. 62/000,836, filed on May 20, 2014, provisional application No. 61/941,670, filed on Feb. 19, 2014.

(52) U.S. Cl.
CPC ......... *A61H 31/005* (2013.01); *A61H 31/008* (2013.01); *A61G 13/04* (2013.01); *A61H 31/006* (2013.01); *A61H 31/007* (2013.01); *A61H 2201/1623* (2013.01); *A61H 2201/1676* (2013.01); *A61H 2201/5007* (2013.01); *A61H 2201/5097* (2013.01); *A61H 2230/208* (2013.01); *A61H 2230/305* (2013.01)

(56) References Cited

U.S. PATENT DOCUMENTS

| | | |
|---|---|---|
| 2,683,452 A | 7/1954 | McCavic |
| 3,461,858 A | 8/1969 | Michaelson |
| 3,509,899 A | 5/1970 | Hewson |
| 3,804,082 A | 4/1974 | Tarjan et al. |
| 3,866,604 A | 2/1975 | Curless |
| 3,870,038 A | 3/1975 | Arblaster |
| 3,931,653 A | 1/1976 | Bien |
| 3,985,126 A | 10/1976 | Baralow |
| 4,060,079 A | 11/1977 | Reinhold, Jr. |
| 4,095,590 A | 6/1978 | Harrigan |
| 4,168,554 A | 9/1979 | Hindes |
| 4,194,732 A | 3/1980 | Liebman |
| 4,266,759 A | 5/1981 | Liebman |
| 4,362,336 A | 12/1982 | Zapf et al. |
| 4,534,075 A | 8/1985 | Schnitzler |
| 4,915,095 A | 4/1990 | Chun |
| 5,048,136 A | 9/1991 | Popitz |
| 5,316,907 A | 5/1994 | Lurie |
| 5,399,148 A | 3/1995 | Waide et al. |
| 5,400,448 A | 3/1995 | Zwickey |
| 5,423,772 A | 6/1995 | Lurie |
| 5,454,779 A | 10/1995 | Lurie et al. |
| 5,487,722 A | 1/1996 | Sherman et al. |
| 5,490,820 A | 2/1996 | Schock et al. |
| 5,538,002 A | 7/1996 | Boussignac et al. |
| 5,549,581 A | 8/1996 | Lurie |
| 5,551,420 A | 9/1996 | Lurie et al. |
| 5,588,422 A | 12/1996 | Lurie |
| 5,618,665 A | 4/1997 | Lurie |
| 5,634,222 A | 6/1997 | Zwickey |
| 5,643,231 A | 7/1997 | Lurie |
| 5,645,522 A | 7/1997 | Lurie et al. |
| 5,692,498 A | 12/1997 | Lurie et al. |
| 5,722,963 A | 3/1998 | Lurie |
| 5,730,122 A | 3/1998 | Lurie |
| 5,730,136 A | 3/1998 | Laufer |
| 5,827,893 A | 10/1998 | Lurie |
| 5,919,210 A | 7/1999 | Lurie |
| 5,984,909 A | 11/1999 | Lurie |
| 6,001,085 A | 12/1999 | Lurie |
| 6,029,667 A | 2/2000 | Lurie |
| 6,062,219 A | 5/2000 | Lurie et al. |
| 6,078,834 A | 6/2000 | Lurie |
| 6,116,288 A | 9/2000 | Yamamura |
| 6,142,962 A | 11/2000 | Mollenauer |
| 6,155,257 A | 12/2000 | Lurie et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie |
| 6,312,399 B1 | 11/2001 | Lurie et al. |
| 6,357,065 B1 | 3/2002 | Adams |
| 6,371,119 B1 | 4/2002 | Zadini et al. |
| 6,425,393 B1 | 7/2002 | Lurie et al. |
| 6,446,288 B1 | 9/2002 | Pi |
| 6,446,962 B1 | 9/2002 | Pi |
| 6,459,933 B1 | 10/2002 | Lurie et al. |
| 6,463,327 B1 | 10/2002 | Lurie et al. |
| 6,486,206 B1 | 11/2002 | Lurie |
| 6,526,973 B1 | 3/2003 | Lurie et al. |
| 6,587,726 B2 | 7/2003 | Lurie et al. |
| 6,604,523 B2 | 8/2003 | Lurie et al. |
| 6,656,166 B2 | 12/2003 | Lurie |
| 6,751,818 B2 | 6/2004 | Troop |
| 6,776,156 B2 | 8/2004 | Lurie et al. |
| 6,810,257 B1 | 10/2004 | Amin |
| 6,863,656 B2 | 3/2005 | Lurie |
| 6,935,336 B2 | 8/2005 | Lurie et al. |
| 6,938,618 B2 | 9/2005 | Lurie et al. |
| 6,986,349 B2 | 1/2006 | Lurie |
| 7,044,128 B2 | 5/2006 | Lurie |
| 7,056,296 B2 | 6/2006 | Sherman et al. |
| 7,060,041 B1 | 6/2006 | Weil et al. |
| 7,082,945 B2 | 8/2006 | Lurie |
| 7,174,891 B2 | 2/2007 | Lurie et al. |
| 7,185,649 B2 | 3/2007 | Lurie |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,275,542 B2 | 10/2007 | Lurie et al. |
| 7,296,312 B2 | 11/2007 | Menkedick |
| 7,311,668 B2 | 12/2007 | Lurie et al. |
| 7,347,832 B2 | 3/2008 | Jensen et al. |
| 7,410,649 B2 | 8/2008 | Yoshimi et al. |
| 7,569,021 B2 | 8/2009 | Sebelius et al. |
| 7,682,312 B2 | 3/2010 | Lurie |
| 7,766,011 B2 | 8/2010 | Lurie |
| 7,836,881 B2 | 10/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,291,534 B2 | 10/2012 | Karlson |
| 8,336,142 B1 | 12/2012 | See |
| 8,408,204 B2 | 4/2013 | Lurie |
| 8,690,807 B2 | 4/2014 | Hiebert |
| 8,702,633 B2 | 4/2014 | Voss et al. |
| 8,752,220 B2 | 6/2014 | Soderberg et al. |
| 8,755,902 B2 | 6/2014 | Lurie et al. |
| 8,763,610 B2 | 7/2014 | Schmidt |
| 8,967,144 B2 | 3/2015 | Lurie |
| 9,107,800 B2 | 8/2015 | Sebelius et al. |

(56) References Cited

U.S. PATENT DOCUMENTS

| | | |
|---|---|---|
| 9,707,152 B2 | 7/2017 | Lurie et al. |
| 9,750,661 B2 | 9/2017 | Lurie |
| 9,801,782 B2 | 10/2017 | Lurie |
| 10,092,481 B2 | 10/2018 | Lurie |
| 10,245,209 B2 | 4/2019 | Lurie |
| 10,350,137 B2 | 7/2019 | Lurie et al. |
| 10,406,068 B2 | 9/2019 | Lurie et al. |
| 10,406,069 B2 | 9/2019 | Lurie et al. |
| 10,667,987 B2 | 6/2020 | Lurie |
| 11,020,314 B2 | 6/2021 | Lurie |
| 11,096,861 B2 | 8/2021 | Lurie |
| 11,246,794 B2 | 2/2022 | Lurie |
| 11,259,988 B2 | 3/2022 | Lurie et al. |
| 2002/0002347 A1 | 1/2002 | Kelly et al. |
| 2002/0069878 A1 | 6/2002 | Lurie et al. |
| 2002/0170562 A1 | 11/2002 | Lurie et al. |
| 2003/0062040 A1 | 4/2003 | Lurie et al. |
| 2003/0181834 A1 | 9/2003 | Sebelius |
| 2004/0016428 A9 | 1/2004 | Lurie |
| 2004/0058305 A1 | 3/2004 | Lurie et al. |
| 2004/0116840 A1 | 6/2004 | Cantrell et al. |
| 2004/0200474 A1 | 10/2004 | Lurie |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt |
| 2006/0162077 A1 | 7/2006 | McDaniel et al. |
| 2006/0258964 A1 | 11/2006 | Biondo |
| 2006/0277683 A1 | 12/2006 | Lamire et al. |
| 2007/0021683 A1 | 1/2007 | Benditt et al. |
| 2007/0157385 A1 | 7/2007 | Lemire |
| 2007/0277826 A1 | 12/2007 | Lurie |
| 2008/0045867 A1 | 2/2008 | Jensen et al. |
| 2008/0047555 A1 | 2/2008 | Lurie et al. |
| 2008/0255482 A1 | 10/2008 | Lurie |
| 2009/0062701 A1 | 3/2009 | Yannopoulos et al. |
| 2009/0277447 A1 | 11/2009 | Voss et al. |
| 2009/0308400 A1 | 12/2009 | Wilson et al. |
| 2010/0031961 A1 | 2/2010 | Schmidt |
| 2010/0179442 A1 | 7/2010 | Lurie |
| 2010/0319691 A1 | 12/2010 | Lurie et al. |
| 2011/0030141 A1 | 2/2011 | Soderberg |
| 2011/0047709 A1 | 3/2011 | Tarsaud et al. |
| 2011/0083271 A1 | 4/2011 | Bhai |
| 2011/0098612 A1 | 4/2011 | Lurie |
| 2011/0132377 A1 | 6/2011 | Phillips |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016179 A1 | 1/2012 | Paradis |
| 2012/0042881 A1 | 2/2012 | Paulussen et al. |
| 2012/0109027 A1 | 5/2012 | Gozelski |
| 2012/0203147 A1 | 8/2012 | Lurie et al. |
| 2012/0260428 A1 | 10/2012 | Franklin |
| 2012/0266383 A1 | 10/2012 | Pi |
| 2012/0330199 A1 | 12/2012 | Lurie et al. |
| 2012/0330200 A1 | 12/2012 | Voss et al. |
| 2013/0231593 A1 | 9/2013 | Yannopoulos et al. |
| 2014/0005566 A1 | 1/2014 | Homuth et al. |
| 2014/0048061 A1 | 2/2014 | Yannopoulos et al. |
| 2014/0082842 A1 | 3/2014 | Jackson |
| 2014/0171839 A1 | 6/2014 | Fleming |
| 2014/0276269 A1 | 9/2014 | Illindala |
| 2014/0324763 A1 | 10/2014 | Lurie |
| 2014/0363391 A1 | 12/2014 | Yannopoulos et al. |
| 2015/0057580 A1 | 2/2015 | Illindala |
| 2015/0120201 A1 | 4/2015 | Silver et al. |
| 2015/0231026 A1 | 8/2015 | Lurie |
| 2015/0231027 A1 | 8/2015 | Lurie |
| 2016/0058660 A1 | 3/2016 | Lurie et al. |
| 2016/0128899 A1 | 5/2016 | Lurie et al. |
| 2016/0228326 A1 | 8/2016 | Lurie et al. |
| 2016/0338904 A1 | 11/2016 | Lurie et al. |
| 2016/0354271 A1 | 12/2016 | Ladozhskay-Gapeenko |
| 2017/0119622 A1 | 5/2017 | Lurie et al. |
| 2017/0258677 A1 | 9/2017 | Lurie et al. |
| 2018/0000687 A1 | 1/2018 | Lurie et al. |
| 2018/0008510 A1 | 1/2018 | Lurie et al. |
| 2018/0125749 A1 | 5/2018 | Lurie et al. |
| 2019/0175444 A9 | 6/2019 | Lurie et al. |
| 2019/0269574 A1 | 9/2019 | Lurie |
| 2019/0282441 A1 | 9/2019 | Lurie |
| 2021/0000685 A1 | 1/2021 | Lurie |
| 2021/0322264 A1 | 10/2021 | Lurie |
| 2021/0361526 A1 | 11/2021 | Lurie et al. |
| 2022/0079839 A1 | 3/2022 | Lurie |
| 2022/0110826 A1 | 4/2022 | Lurie |
| 2022/0265509 A1 | 8/2022 | Lurie et al. |

FOREIGN PATENT DOCUMENTS

| | | |
|---|---|---|
| EP | 3107516 A2 | 12/2016 |
| TW | 200934469 A | 8/2009 |
| WO | 01-28484 A1 | 4/2001 |
| WO | 2015/127102 A2 | 8/2015 |
| WO | 2015127102 A3 | 11/2015 |
| WO | 2015/026460 A1 | 2/2016 |
| WO | 2017066770 A1 | 4/2017 |
| WO | 2019125682 A1 | 6/2019 |

OTHER PUBLICATIONS

U.S. Appl. No. 14/626,770, Non-Final Office Action, Mailed on Sep. 27, 2017, 10 pages.

U.S. Appl. No. 14/626,770, Non-Final Office Action, Mailed on Oct. 16, 2017, 11 pages.

U.S. Appl. No. 14/935,262, "Corrected Notice of Allowability", May 4, 2017, 6 pages.

U.S. Appl. No. 15/285,063, Non-Final Office Action, Mailed on Jan. 12, 2018, 17 pages.

U.S. Appl. No. 15/601,494, "Corrected Notice of Allowability", May 30, 2019, 2 pages.

U.S. Appl. No. 15/652,023, Advisory Action, Mailed on Mar. 16, 2020, 3 pages.

U.S. Appl. No. 15/652,023, Advisory Action, Mailed on Feb. 24, 2021, 4 pages.

U.S. Appl. No. 15/652,023, Final Office Action, Mailed on Jan. 9, 2020, 14 pages.

U.S. Appl. No. 15/652,023, Final Office Action, Mailed on Nov. 17, 2020, 18 pages.

U.S. Appl. No. 15/652,023, Non-Final Office Action, Mailed on May 1, 2020, 14 pages.

U.S. Appl. No. 15/652,023, Notice of Allowance, Mailed on Apr. 2, 2021, 8 pages.

U.S. Appl. No. 15/689,670, Final Office Action, Mailed on Apr. 16, 2020, 16 pages.

U.S. Appl. No. 15/796,579, Advisory Action, Mailed on Jun. 24, 2020, 4 pages.

U.S. Appl. No. 15/796,579, Final Office Action, Mailed on Feb. 25, 2021, 15 pages.

U.S. Appl. No. 15/796,579, Final Office Action, Mailed on Apr. 16, 2020, 9 pages.

U.S. Appl. No. 15/796,579, Non-Final Office Action, Mailed on Aug. 6, 2020, 13 pages.

U.S. Appl. No. 16/432,633, Non-Final Office Action, Mailed on Jan. 14, 2021, 7 pages.

U.S. Appl. No. 17/559,637, Non-Final Office Action, Mailed on Mar. 30, 2023, 10 pages.

Application No. AU2016337605, "First Examination Report", Jul. 16, 2020, 5 pages.

Application No. AU2016337605, "Second Examination Report", Apr. 23, 2021, 4 pages.

Application No. EP15751853.1, Office Action, Mailed on Nov. 14, 2019, 9 pages.

(56) References Cited

OTHER PUBLICATIONS

Application No. EP16856418.5, Extended European Search Report, Mailed on Jun. 4, 2019, 8 pages.
Application No. EP16856418.5, Notice of Decision to Grant, Mailed on Jul. 23, 2020, 3 pages.
Application No. JP2018-539249, Notice of Allowance, Mailed on Apr. 27, 2021, 6 p. (pp. 1-3 English translation, pp. 4-6 original document).
Application No. JP2018-539249, Office Action, Mailed on Oct. 27, 2020, 13 p. (pp. 1-5 English translation, pp. 6-13 original document).
Application No. JP2018-539249, Office Action, Mailed on Feb. 24, 2021, 6 p. (pp. 1-3 English translation, pp. 4-6 original document).
Application No. PCT/US2018/061789, International Preliminary Report on Patentability, Mailed on Jul. 2, 2020, 8 pages.
Yannopoulos et al., "Controlled Pauses at the Initiation of Sodium Nitroprusside-enhanced Cardiopulmonary Resuscitation Facilitate Neurological and Cardiac Recovery After 15 Mins of Untreated Ventricular Fibrillation", Critical Care Medicine, vol. 40, No. 5, May 2012, pp. 1562-1569.
Song, et al., "Effectiveness of Chest Compression Feedback During Cardiopulmonary Resuscitation in Lateral Tilted and Semirecumbent Positions"; A Randomised Controlled Stimulation Study, 2015, Anaesthesia, vol. 70, Issue 11 (Year: 2015).
Gocze et al., "The Effects of the Semirecumbent Position on Hemodynamic Status in Patients on Invasive Mechanical Ventilation"; Prospective Randomized Multivariable Analysis, 2013, Critical Care, 17:R80 (Year: 2013).
Notice of Allowance mailed Apr. 10, 2019 in U.S. Appl. No. 15/601,494, all pages.
Notice of Allowance mailed Jul. 8, 2019 in U.S. Appl. No. 15/986,466, all pages.
Final Office action mailed Jul. 11, 2019 in U.S. Appl. No. 15/160,492, all pages.
Notice of Allowance mailed Jul. 17, 2019 in U.S. Appl. No. 15/285,063, all pages.
Notice of Allowance mailed Feb. 5, 2021 in related U.S. Appl. No. 16/058,851, all pgs.
First Action Interview Pilot Program Pre-Interview Communication mailed Oct. 17, 2018 in related U.S. Appl. No. 15/986,466, all pgs.
Voelckel et al."The Effects of Positive End-expiratory Pressure During Active Compression Decompression Cardiopulmonary Resuscitation with the Inspiratory Threshold valve." Anesthesia and Analgesia. Apr. 2001: 92(4): 967-74.
Zoll Medical Corporation, "The System for High-Quality CPR", Retrieved from https://www.zoll.com/medical-technology/cpr, Accessed on Sep. 11, 2018, all pages.
Physio-Control Inc., "LUCAS CPR," retrieved from http://www.lucas.cpr.com/en/lucas_cpr/lucas_cpr, accessed on Sep. 7, 2018, all pages.
Website: https://www.physio-control.com/WCProductDetails.aspx?id=2147484788&langtype=5129.
Lurie, Keith G. (2015) "The Physiology of Cardiopulmonary Resuscitation," Anesthesia & Analgesia, doi: 10.1513/ANE. 0000000000000926, in Ryu, et al. "The Effect of Head Up Cardiopulmonary Resuscitation on Cerebral and Systemic Hemodynamics." Resuscitation. 2016: 102: 29-34.
Lurie, Keith G. "Mechanical Devices for Cardiopulmonary Resuscitation: An Update," "Emergency Medicine Clinics of North America," Dec. 2002, vol. 20, Issue 4, pp. 771-784.
EP Patent Application No. 15751853.1 filed Feb. 19, 2015, Extended European Search Report mailed Feb. 10, 2017, all pages.
Debaty G, et. al. "Tilting for perfusion: Head-up Position During Cardiopulmonary Resuscitation Improves Brain Flow in a Porcine Model of Cardiac Arrest." Resuscitation. 2015: 87: 38-43.
U.S. Appl. No. 15/133,967, filed Apr. 20, 2016, Final Office Action mailed Mar. 13, 2017, all pages.
Advisory Action Mailed Jul. 11, 2016, for U.S. Appl. No. 14/677,562, 4 pages.

Final Office Action Mailed May 27, 2016, for U.S. Appl. No. 14/667,562, 9 pages.
International Search Report and Written Opinion mailed on Jul. 8, 2015 for International Patent Application No. PCT/US2015/016651, all pages.
International Search Report and Written Opinion of PCT/US2016/057366 mailed Mar. 13, 2017, all pages.
Non-Final Office Action mailed Aug. 26, 2016, for U.S. Appl. No. 14/996,147, 15 pages.
Non-Final Office Action Mailed Jan. 6, 2016, for U.S. Appl. No. 14/677,562, 33 pages.
Non-Final Office Action mailed Sep. 9, 2016, for U.S. Appl. No. 14/935,262, all pages.
Non-Final Office Action mailed Sep. 6, 2016, for U.S. Appl. No. 14/677,562, 12 pages.
U.S. Appl. No. 14/677,562, filed Apr. 2, 2015, Non-Final Office Action mailed Jun. 13, 2017, all pages.
U.S. Appl. No. 15/133,967, filed Apr. 20, 2016, Advisory Action mailed Jun. 7, 2017, all pages.
U.S. Appl. No. 14/677,562 received a Corrected Notice of Allowability, mailed Sep. 4, 2018, 2 pages.
Notice of Allowance mailed Apr. 21, 2021 in related U.S. Appl. No. 16/432,633, all pgs.
U.S. Appl. No. 14/677,562 received a Final Office Action, mailed Jan. 23, 2018, 9 pages.
U.S. Appl. No. 14/677,562 received a Non-Final Office Action, mailed Sep. 24, 2015, 12 pages.
U.S. Appl. No. 14/677,562 received a Notice of Allowance, mailed Jul. 23, 2018, 10 pages.
U.S. Appl. No. 14/935,262 received a Restriction Requirement, mailed Jun. 2, 2016, 7 pages.
U.S. Application No. 14/996,147 received a Non-Final Office Action, mailed Aug. 26, 2016, 15 pages.
U.S. Application No. 14/996,147 received a Restriction Requirement, mailed Jul. 18, 2016, 7 pages.
U.S. Appl. No. 15/133,967 received a Notice of Allowance, mailed Jul. 5, 2017, 11 pages.
U.S. Appl. No. 15/160,492 received a Final Office Action, mailed Aug. 9, 2018, 15 pages.
U.S. Appl. No. 15/160,492 received a Non-Final Office Action, mailed Jan. 11, 2018, 15 pages.
U.S. Appl. No. 15/285,063 received a Final Office Action, mailed May 11, 2018, 19 pages.
EP15751853.1 received an Extended European Search Report, mailed Oct. 2, 2017, 9 pages.
PCT/US2015/016651 received an Invitation to Pay Additional Fees and Partial Search Report, mailed Apr. 27, 2015, 3 pages.
PCT/US2016/057366 received an Invitation to Pay Additional Fees and Partial Search Report, mailed Dec. 12, 2016, 2 pages.
International Patent Application No. PCT/US2015/016651 received an International Preliminary Report on Patentability, mailed Aug. 23, 2016, 10 pages.
U.S. Appl. No. 14/935,262 received a Notice of Allowance, mailed Jan. 4, 2017, 16 pages.
U.S. Appl. No. 14/996,147 received a Notice of Allowance, mailed Jan. 18, 2017, all pages.
U.S. Appl. No. 14/677,562 received a Final Office Action, mailed Jan. 9, 2017, all pages.
International EP Patent Application No. 15751853.1 received an Extended European Search Report, mailed Feb. 10, 2017, all pages.
U.S. Appl. No. 14/677,562 received a Final Office Action, mailed Jan. 9, 2017, 19 pages.
U.S. Appl. No. 14/677,562 received a Notice of Allowance, mailed Jul. 23, 2018, 13 pages.
U.S. Appl. No. 14/996,147 received a Notice of Allowance, mailed Jan. 18, 2017, 17 pages.
U.S. Appl. No. 15/160,492 received a Final Rejection mailed Aug. 9, 2018, all pages.
U.S. Appl. No. 15/285,063 Final Rejection mailed May 11, 2018, all pages.
U.S. Appl. No. 14/626,770 received Non-Final Rejection mailed Jun. 7, 2018, all pages.

(56) References Cited

OTHER PUBLICATIONS

PCT/US2016/057366 Application No. received an International Preliminary Report on Patentability, issued Apr. 17, 2018, all pages.
U.S. Appl. No. 14/935,262 received a Notice of Allowance mailed, Jan. 4, 2017, all pages.
Voelckel et al."The Effects of Positive end-25 Expiratory Pressure During Active Compression Decompression Cardiopulmonary Resuscitation with the Inspiratory Threshold Valve." Anesthesia and Analgesia. Apr. 2001: 92(4): 967-74.
Ryu, et. al. "The Effect of Head Up Cardiopulmonary Resuscitation on Cerebral and Systemic Hemodynamics." Resuscitation. 2016: 102: 29-34. Print.
Moore, et al., "Head and Thorax Elevation During Active Compression Decompression Cardiopulmonary Resuscitation with an Impedance Threshold Device Improves Cerebral Perfusion in a Swine Model of Prolonged Cardiac Arrest" doi.org/10.1016/j.resuscitation.2017.07.033.
Khandelwal, et al. "Head-Elevated Patient Positioning Decreases 25 Complications of Emergent Tracheal Intubation in the Ward and Intensive Care Unit." Anesthesia & Analgesia. Apr. 2016: 122: 1101-1107.
U.S. Appl. No. 15/285,063 received an Advisory Action, mailed Dec. 20, 2018, 4 pages.
U.S. Appl. No. 14/626,770 received a Notice of Allowance, mailed Dec. 14, 2018, 9 pages.
U.S. Appl. No. 15/160,492 received an Advisory Action, mailed Dec. 3, 2018, 3 pages.
Non-Final Office action mailed on Jun. 28, 2019 in U.S. Appl. No. 15/652,023, all pgs.
U.S. Appl. No. 15/160,492 received a Non-Final Office Action, mailed Dec. 13, 2018, 25 pages.
International Preliminary Report on Patentability mailed Apr. 26, 2018 in related PCT application No. PCT/US2016/057366, all pages.
First Action Interview Summary mailed Jan. 7, 2019 in related U.S. Appl. No. 15/986,466, 6 pgs.
Non-Final Office Action mailed Jan. 28, 2019 in related U.S. Appl. No. 15/285,063, 18 pgs.
Notice of Allowance mailed Jul. 8, 2019 in related U.S. Appl. No. 15/986,466, all pgs.
International Search Report and Written Opinion mailed Feb. 11, 2019 in related PCT application No. PCT/US2018/061789, all pgs.
International Preliminary Report on Patentability mailed Sep. 1, 2016, for International Patent Application No. PCT/US2015/016651, all pages.
Notice of Allowance mailed Feb. 3, 2020 in related U.S. Appl. No. 15/580,827, all pgs.
Advisory Action mailed Oct. 3, 2019 in U.S. Appl. No. 15/160,492, all pages.
Non-Final Action mailed Oct. 4, 2019 in U.S. Appl. No. 15/796,579, all pages.
Non-Final Action mailed Oct. 4, 2019 in U.S. Appl. No. 15/689,670, all pages.
Non-Final Action mailed Nov. 1, 2019 in U.S. Appl. No. 15/160,492, all pages.
Notice of Publication mailed Aug. 11, 2016 in related U.S. Appl. No. 15/133,967, all pgs.
Non-Final Office action mailed on Jun. 28, 2019 in U.S. Appl. No. 15/652,023, all pages.
Non-Final Office Action mailed Oct. 11, 2016 in related U.S. Appl. No. 15/133,967, all pgs.
Non-Final Office Action issued in U.S. Appl. No. 17/409,294, dated Jul. 13, 2023 in 7 pages.
Notice of Allowance issued in U.S. Appl. No. 17/409,294, dated Oct. 25, 2023 in 5 pages.
Notice of Allowance issued in U.S. Appl. No. 17/559,637, dated Sep. 15, 2023 in 8 pages.
Non-Final Office Action issued in U.S. Appl. No. 17/668,944, dated Jun. 26, 2023 in 11 pages.
Non-Final Office Action issued in U.S. Appl. No. 18/161,751, dated Jun. 8, 2023 in 13 pages.
Notice of Allowance issued in U.S. Appl. No. 18/161,751, dated Jul. 31, 2023 in 8 pages.

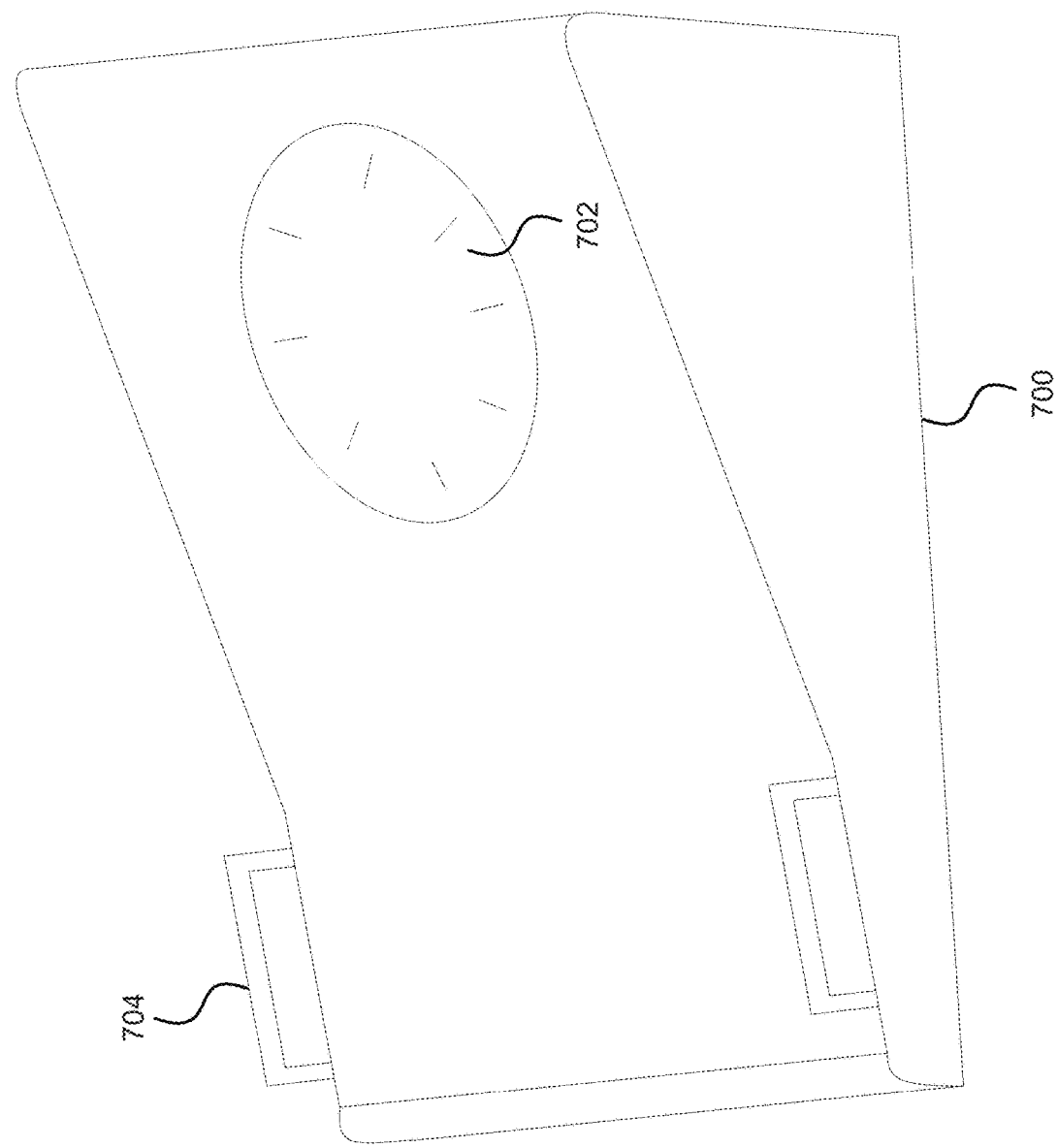

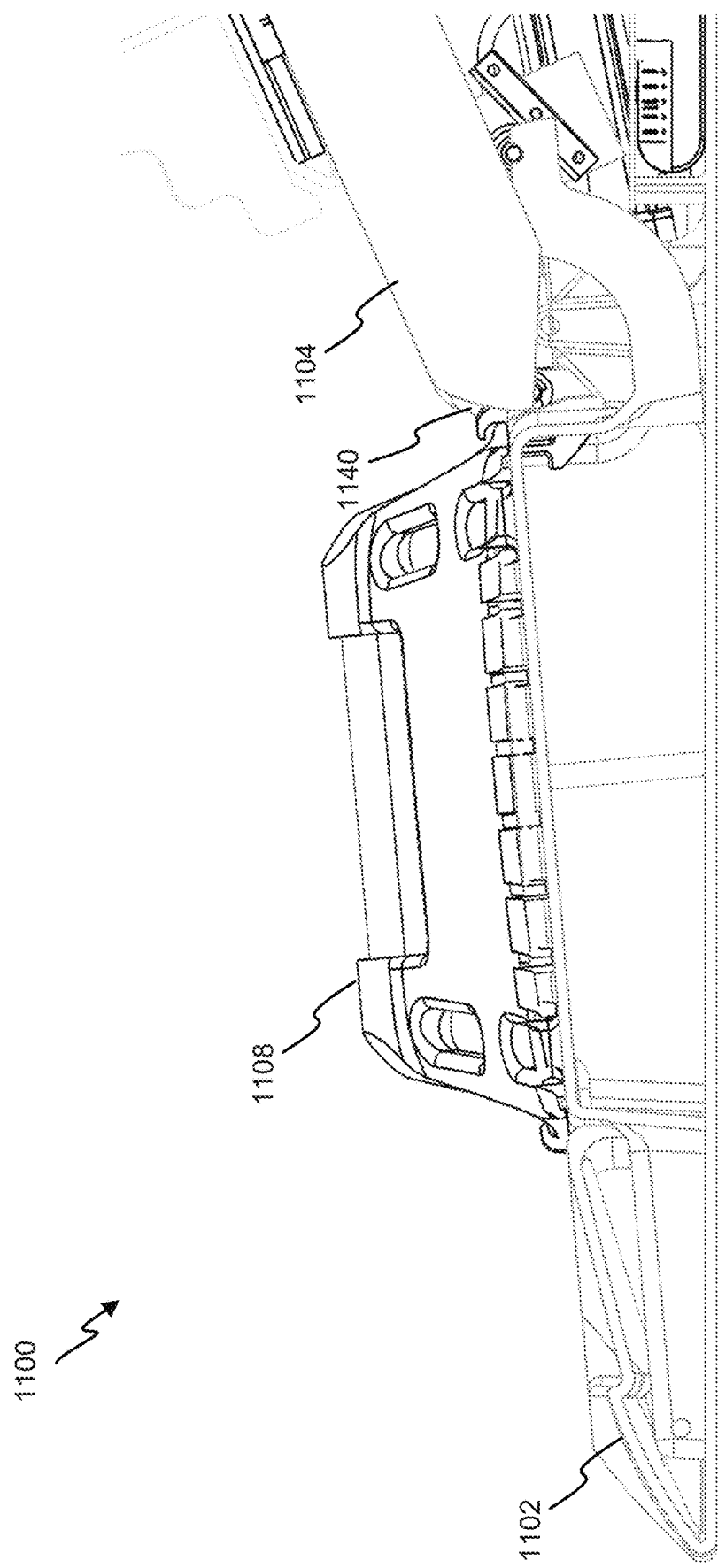

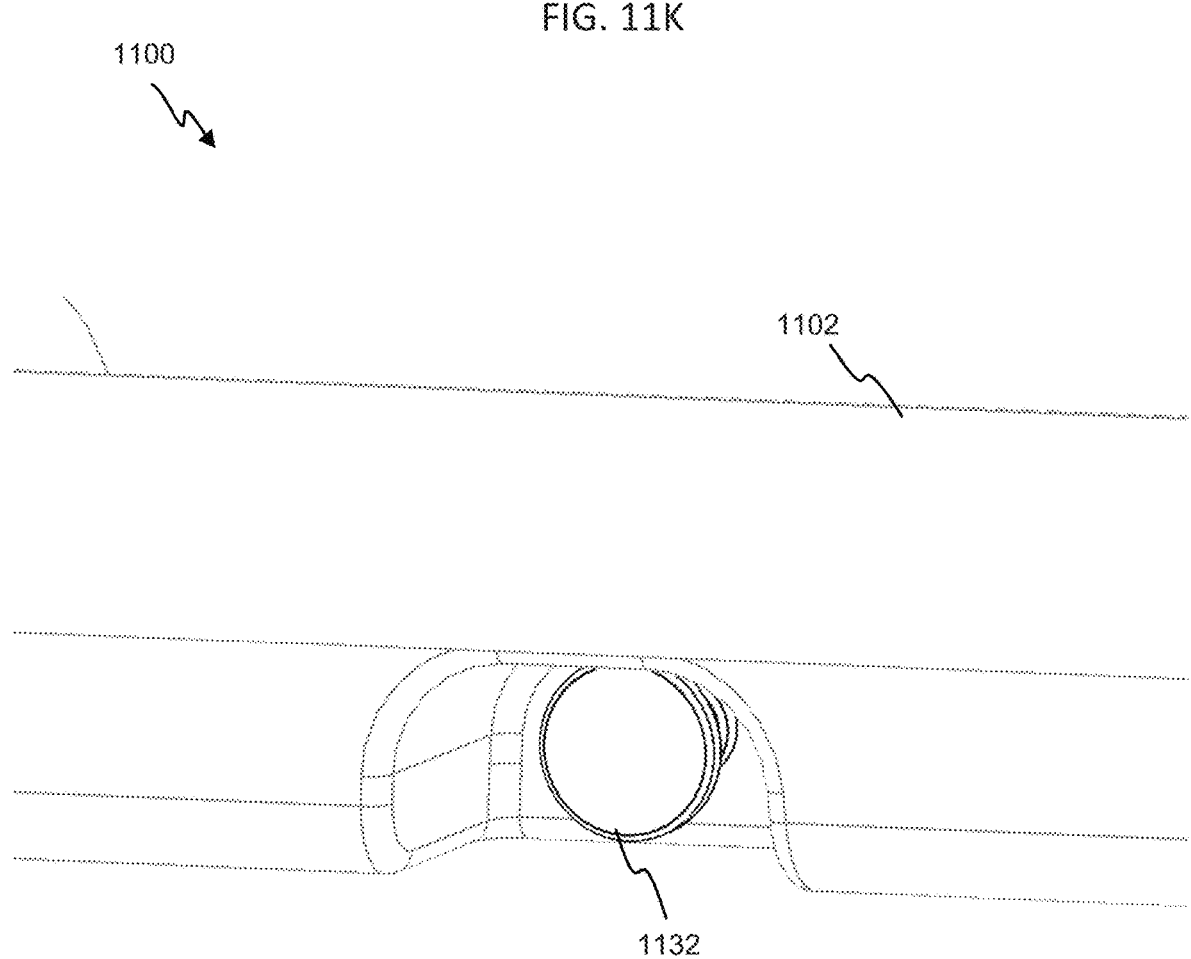

METHODS AND SYSTEMS TO REDUCE BRAIN DAMAGE

CROSS-REFERENCES TO RELATED APPLICATIONS

This application is a continuation in part of U.S. application Ser. No. 16/058,851, filed Aug. 8, 2018, which is a continuation in part of U.S. application Ser. No. 15/986,466, filed May 22, 2018, which is a continuation in part of U.S. application Ser. No. 15/850,827, filed Dec. 21, 2017, which is a continuation in part of U.S. application Ser. No. 15/601, 494, filed May 22, 2017, which is a continuation in part of U.S. application Ser. No. 15/285,063, filed Oct. 4, 2016, which is a continuation in part of U.S. application Ser. No. 15/160,492, filed May 20, 2016, which is a continuation in part of U.S. application Ser. No. 15/133,967, filed Apr. 20, 2016, now U.S. Pat. No. 9,801,782, issued Oct. 31, 2017, which is a continuation in part of U.S. application Ser. No. 14/996,147, filed Jan. 14, 2016, now U.S. Pat. No. 9,750, 661, issued Sep. 5, 2017, which is a continuation in part of U.S. application Ser. No. 14/935,262, filed Nov. 6, 2015, now U.S. Pat. No. 9,707,152, issued Jul. 18, 2017, which claims the benefit of U.S. Provisional Application No. 62/242,655, filed Oct. 16, 2015, the complete disclosures of which are hereby incorporated by reference for all intents and purposes.

U.S. application Ser. No. 16/058,851, filed Aug. 8, 2018 (referenced above) also claims the benefit of U.S. Provisional Application No. 62/542,394, filed Aug. 8, 2017, the entire disclosure of which is hereby incorporated by reference for all intents and purposes.

U.S. application Ser. No. 15/986,466, filed May 22, 2018 (referenced above) also claims the benefit of U.S. Provisional Application No. 62/509,469, filed May 22, 2017, the complete disclosure of which is hereby incorporated by reference for all intents and purposes.

U.S. application Ser. No. 14/935,262, filed Nov. 6, 2015, now U.S. Pat. No. 9,707,152, issued Jul. 18, 2017 (referenced above) is also a continuation in part of U.S. application Ser. No. 14/677,562, filed Apr. 2, 2015, now U.S. Pat. No. 10,092,481, issued Oct. 9, 2018, which is a continuation of U.S. application Ser. No. 14/626,770, filed Feb. 19, 2015, which claims the benefit of U.S. Provisional Application No. 61/941,670, filed Feb. 19, 2014, U.S. Provisional Application No. 62/000,836, filed May 20, 2014, and U.S. Provisional Application No. 62/087,717, filed Dec. 4, 2014, the complete disclosures of which are hereby incorporated by reference for all intents and purposes.

BACKGROUND OF THE INVENTION

Cardiac arrest is a leading cause of death. Despite progress, the vast majority of patients never wake up again after cardiac arrest. While there are many reasons for the currently dismal outcomes, one important reason involves the rapid onset of brain swelling and edema after cardiac arrest and resuscitation techniques. Improvements to reduce brain damage, swelling, and edema after cardiac arrest are needed.

BRIEF SUMMARY OF THE INVENTION

Embodiments of the invention are directed toward systems, devices, and methods of reducing brain edema and brain swelling. Such techniques reduce the spikes in intracranial pressure (ICP) associated with various resuscitation techniques and result in lower intracranial pressure while increasing cerebral perfusion pressure, cerebral output, and systolic blood pressure (SBP) during CPR and after resuscitation compared with CPR administered to an individual in the flat and supine position. The configuration may also preserve a central blood volume and lower pulmonary vascular resistance and circulate drugs to the brain and heart used during CPR more effectively. This provides a more effective and safe method of performing CPR for extended periods of time. The head and thorax up configuration during CPR and after resuscitation may also preserve the patient in the sniffing position to optimize airway management and reduce complications associated with endotracheal intubation.

In one aspect, a method to reduce brain injury and brain swelling is provided. Even when patients survive a cardiac arrest, ⅓-⅔ or them may have brain injury (e.g. Alameda County CA and Seoul, Korea). The greater the reduction in the potential brain injury, the better the brain function of the survivors. The method may include performing conventional manual CPR and/or performing active compression decompression cardiopulmonary resuscitation on an individual in a supine position with an intrathoracic pressure regulation device. The individual's head, shoulders, and heart may be elevated relative to the individual's lower body. The head may be elevated to a height of between about 10 cm and 30 cm above the horizontal plane and the heart may be elevated to a height of between about 1 cm to 10 cm or 2 cm and 10 cm above the horizontal plane. Chest compressions may be performed on the individual and actively decompressing the individual's chest while the individual's head, shoulders, and heart are elevated. Intrathoracic pressure of the individual may be regulated, for example, using an impedance threshold device both while the individual is in the supine position and while the individual's head, shoulders, and heart are elevated relative to the lower body, thereby reducing brain edema during CPR. After a successful resuscitation the head and thorax remain elevated as long as there is adequate blood flow to the brain, which is generally associated with a mean arterial pressure (MAP) of >65 mmHg.

In some embodiments a method to reduce brain injury and brain swelling may also include, upon stopping the performance of CPR, maintaining the individual in a head up position with the individual's head, shoulders, and heart elevated as long as a sufficient mean arterial pressure is maintained to support blood flow to the brain in the head up position.

In some embodiments, a method to reduce brain injury and brain swelling may include performing active compression decompression cardiopulmonary resuscitation (ACD-CPR) on an individual while the individual's heart is at a position of between about 0 cm to 8 cm above horizontal and the individual's head is at a position of between about 0 and 15 cm above horizontal. The method may also include elevating the individual's head, shoulders, and heart relative to the individual's lower body while the individual's lower body remains generally aligned with the horizontal plane to cause blood to actively drain venous blood from the brain to reduce intracranial pressure. The head may be elevated to a height of between about 10 cm and 30 cm above the horizontal plane and the heart may be elevated to a height of between about 1 cm to 10 cm or 2 cm and 10 cm above the horizontal plane. The method may further include performing chest compressions on the individual and actively decompressing the individual's chest while the individual's head, shoulders, and heart are elevated. The method may include regulating an intrathoracic pressure of the individual using a pressure regulation device, such as an impedance threshold device both while the individual is in the supine position and while the individual's head, shoulders, and heart are elevated relative to the lower body, thereby reducing brain edema during CPR by significantly reducing an amplitude of a venous pressure wave with each chest compression. The method may also include, upon stopping the performance of CPR, maintaining the individual in a head up position with the individual's head, shoulders, and heart elevated as long as a sufficient mean arterial pressure is maintained to support blood flow to the brain in the head up position.

In some embodiments, a method to reduce brain injury and brain swelling includes performing cardiopulmonary resuscitation (CPR) on an individual in cardiac arrest while the individual's heart is at a position of between about 0 cm to 8 cm above horizontal and the individual's head is at a position of between about 0 and 15 cm above horizontal. The method may also include elevating the individual's head, shoulders, and heart relative to the individual's lower body while the individual's lower body remains generally aligned with the horizontal plane to cause blood to actively drain venous blood from the brain to reduce intracranial pressure. The head may be elevated to a height of between about 10 cm and 30 cm above the horizontal plane and the heart is elevated to a height of between about 1 cm to 10 cm or 2 cm and 10 cm above the horizontal plane. The method may also include delivering chest compressions to the individual's chest using a CPR assist device while the individual's head, shoulders, and heart are elevated and regulating an intrathoracic pressure of the individual using an intrathoracic pressure regulation device both while the individual is in the supine position and while the individual's head, shoulders, and heart are elevated relative to the lower body, thereby reducing brain edema during CPR by significantly reducing an amplitude of a venous pressure wave with each chest compression. The method may further include, upon stopping the performance of CPR, maintaining the individual in a head up position with the individual's head, shoulders, and heart elevated as long as a sufficient mean arterial pressure is maintained to support blood flow to the brain in the head up position.

In another aspect, a device to reduce brain injury after cardiac arrest and during CPR is provided. The device may include an elevation support having a generally planar surface in general alignment with a horizontal plane. A portion of the generally planar surface may be configured to be bent upward to elevate the head, shoulders, and heart of an individual at an angle of between about 10 and 60 degrees above the horizontal plane. The generally planar surface may include a mounting point that is configured to receive a cardiopulmonary resuscitation (CPR) assist device such that the CPR assist device is positioned in alignment with the heart of the individual. The generally planar surface may also incorporate a CPR assist device.

BRIEF DESCRIPTION OF THE DRAWINGS

FIG. 7 depicts one embodiment of an elevation device according to embodiments.

FIG. 11G depicts the elevation device of FIG. 11A in a lowered position.

FIG. 11K depicts a release knob of the elevation device of FIG. 11A.

DETAILED DESCRIPTION OF THE INVENTION

Under normal physiological conditions arterial blood is pumped to the brain and drains through the venous system.

Figure 1:
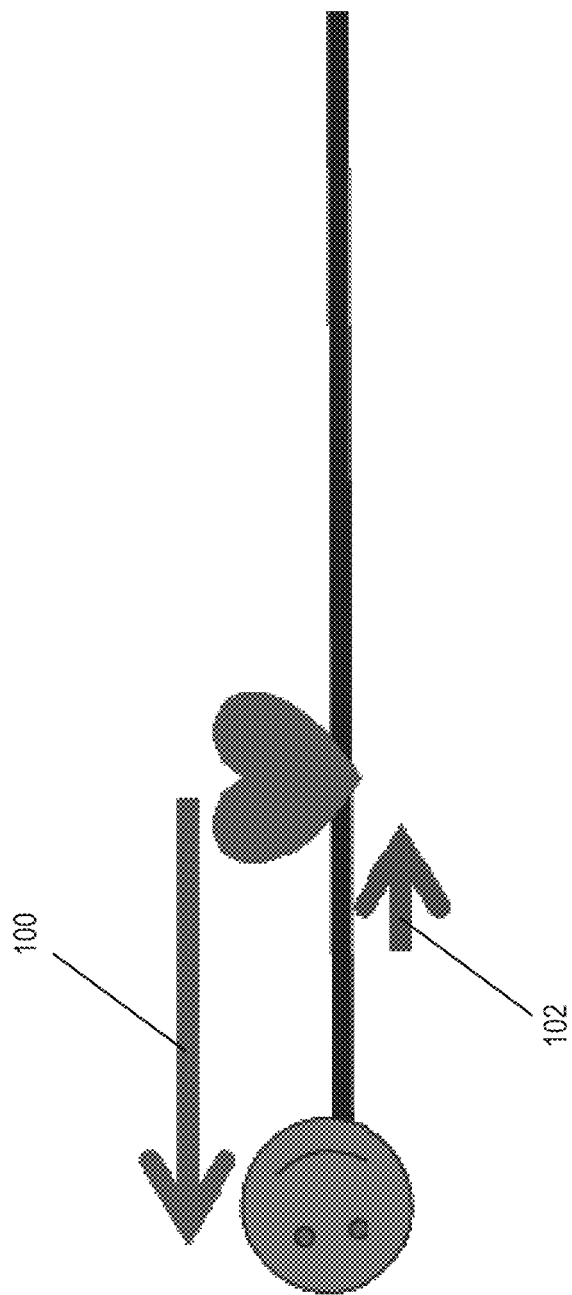
FIG. 1 is a schematic showing arterial and venous blood flow under normal physiological conditions.
Figure 2:
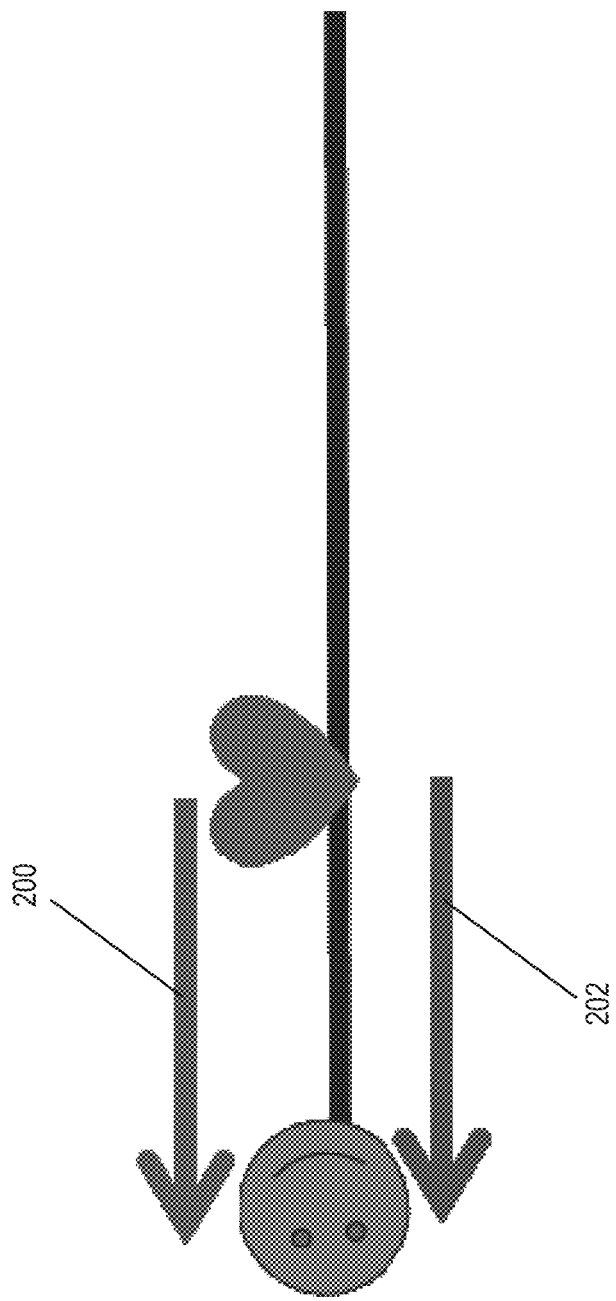
FIG. 2 is a schematic showing arterial and venous pressures during conventional closed chest CPR.

This is shown schematically in FIG. 1 with the red arrow 100 representing arterial blood being pumped to the brain and the blue arrow 102 representing the blood draining through the venous system. During conventional manual closed chest cardiopulmonary resuscitation or standard (S) CPR (performed when the patient is in a generally supine or horizontal position), chest compressions increase arterial and venous pressures simultaneously as depicted in FIG. 2 with the red arrow 200 representing the arterial pressure and the blue arrow 202 representing the venous pressure. A bidirectional high pressure compression wave is delivered to the brain with every compression. The pressure within the thorax increases with each compression and this rise in pressure is transmitted nearly instantaneously to the brain via the arterial and venous blood vessels and paravertebral venous sinuses, a complex and large network of veins that surround the spinal column from the base of the skull to the sacrum. This is an inherent limitation of S-CPR and can result in a spike in ICP resulting in reduced blood flow to the brain during the compression phase of CPR and a "concussion with every compression". The ICP can increase to dangerously high levels with each compression during CPR in the horizontal plane. This results in brain damage, brain swelling, and brain injury, especially in the setting of simultaneous lack of oxygen.

Brain edema can occur very rapidly, within one hour, in the setting of this trauma. Approximately half of all patients who have cardiac arrest outside the hospital and then undergo CT scan have evidence of moderate to severe brain swelling. These patients rarely wake up.

Figure 3:
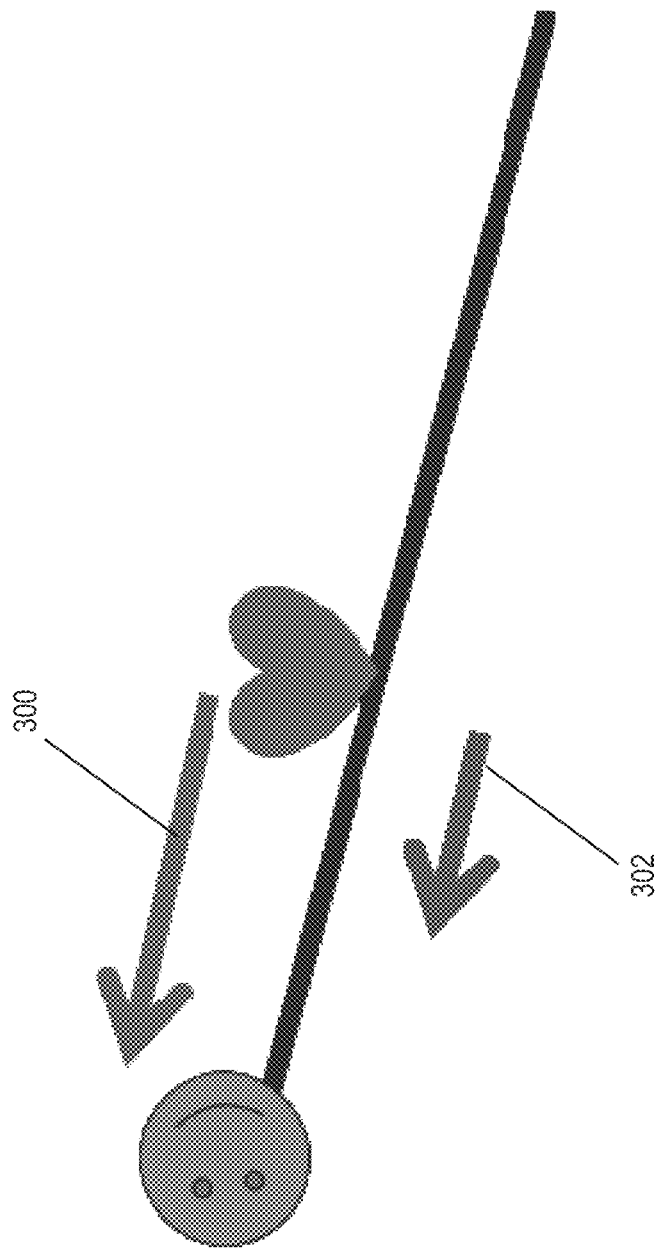
FIG. 3 is a schematic showing arterial and venous pressures during CPR with the head elevated.

Embodiments of the present invention reduce brain injury after cardiac arrest by reducing the potential for bidirectional high pressure compression waves bombarding the brain with every S-CPR chest compression and the benefits are continued after a successful resuscitation. Embodiments of the invention provide methods and devices to elevate the heart alone or the head and the thorax, to reduce the venous pressure head and thus reduce the potential for bidirectional high pressure compression waves to damage the brain while still providing sufficient arterial blood flow to the brain. The reduction of the venous pressure head is depicted in FIG. 3 with the arterial blood flow being represented by the red arrow 300 and the reduced venous pressure head being represented by blue arrow 302. Elevation of the head and heart has recently been shown to reduce ICP as gravity draws venous blood out of the brain almost immediately upon elevation of the head. Thus, the venous pressure wave amplitude is significantly reduced as is the ICP, resulting in a lower potential for brain injury with each chest compression. The lower the concussion potential the lower the chances that brain selling and edema will develop after CPR is discontinued and the patient is resuscitated.

Figure 4A:
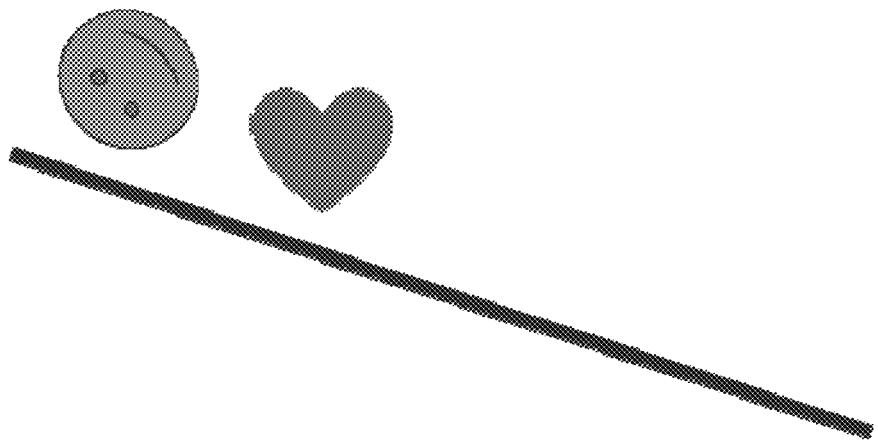
FIG. 4A is a schematic showing a head up configuration according to embodiments.
Figure 4B:
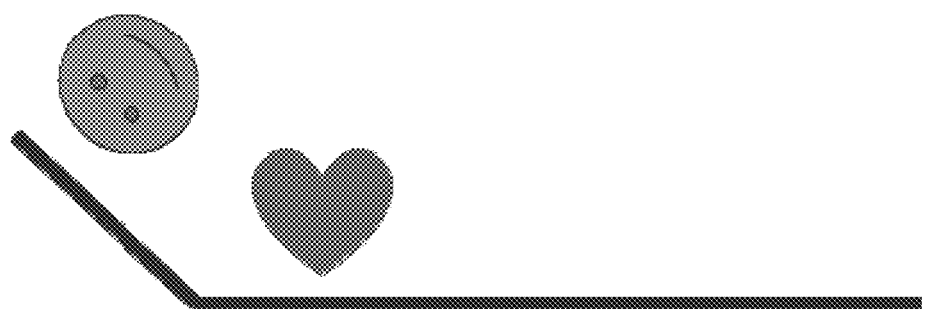
FIG. 4B is a schematic showing a head up configuration according to embodiments.
Figure 4C:
FIG. 4C is a schematic showing a head up configuration according to embodiments.
Figure 4D:
FIG. 4D is a schematic showing a head up configuration according to embodiments.

To achieve the desired reduction in the venous pressure head, an individual's entire body could be elevated in a head up tilt position as depicted in FIG. 4A, elevation of the head alone as depicted in FIG. 4B, elevation of the upper body to a single angular position by bending the body at the waist as depicted in FIG. 4C, or elevation of the heart and the head to different angular positions as depicted in FIG. 4D. For example, FIG. 4D shows that the optimal head elevation may include a way to elevate the head and thorax only, with different levels of elevation. While such a change in position may seem obvious, elevation of the head in any of the positions shown in FIGS. 4A-4D with simultaneous performance of S-CPR for a prolonged period of time would actually accelerate the odds of death. This is because S-CPR is very inefficient and unable to effectively pump blood uphill to the brain. Blood would flow out of the brain due to gravity and brain perfusion and blood flow would be reduced.

In order to pump blood "uphill" to the brain during head up CPR for more than between about 5-10 minutes it is necessary to enhance circulation overall. One approach is to include a mechanism to increase the decompression phase negative intrathoracic pressures during CPR to turn the thorax into a more efficient blood pump. These mechanisms to increase the decompression phase negative intrathoracic pressures during CPR a) enhance blood flow back to the right heart from the non-thoracic structures (e.g. brain, abdomen, extremities), b) lower ICP, and c) enhance forward blood flow to the brain, heart, and other vital organs. One approach is to generate greater decompression phase negative intrathoracic pressure includes use of the family of technologies including the impedance threshold device (ITD), an active compression-decompression CPR device (ACD CPR) device, and other methods to deliver CPR and regulate intrathoracic pressure, including manual and automated CPR devices (LUCAS, AutoPulse, Weil Minicompressor, Michigan thumper, and the like) and intrathoracic pressure regulators. For example, CPR with at least the head and heart elevated may be performed using any one of a variety of manual or automated conventional CPR devices (e.g. active compression-decompression CPR, load-distributing band, or the like) alone or in combination with any one of a variety of systems for regulating intrathoracic pressure, such as a threshold valve that interfaces with a patient's airway (e.g., an ITD), the combination of an ITD and a Positive End Expiratory Pressure valve, or other means to regulate intrathoracic pressure to generate a sub-atmospheric pressure during the decompression phase of CPR. When CPR is performed with the head and heart elevated, gravity drains venous blood from the brain to the heart, resulting in refilling of the heart after each compression and a substantial decrease in ICP, thereby reducing resistance to forward brain flow. This maneuver also reduces the likelihood of simultaneous high-pressure waveform simultaneously compressing the brain during the compression phase. While this may represent a potential significant advance, tilting the entire body upward has the potential to reduce coronary and cerebral perfusion during a prolonged resuscitation effort since over time gravity will cause the redistribution of blood to the abdomen and lower extremities.

Some of the head up devices (HUD) described herein mechanically elevate the thorax and the head, maintain the head and thorax in the correct position for CPR when head up and supine using an expandable and retractable thoracic back plate and a neck support, and allow a thoracic plate to angulate during head elevation so the piston of a CPR assist device always compresses the sternum in the same place and a desired angle (such as, for example, a right angle) is maintained between the piston and the sternum during each chest compression. Embodiments were developed to provide each of these functions simultaneously, thereby enabling maintenance of the compression point at the anatomically correct place when the patient is flat (supine) or their head and chest are elevated.

In some embodiments, it may be advantageous to carefully control the speed at which a patient is elevated and/or lowered before, during, and/or after CPR. For example, it is advantageous to elevate the head slowly when first starting CPR since the blood flow "uphill" may barely be adequate to provide sufficient blood flow to the head and brain. In other words, it takes time to pump blood uphill with the types of chest compression techniques described herein, so it is advantageous to elevate the patient's upper body slowly to make this uphill pumping easier. In contrast, blood drains rapidly from the head when the patient has no blood pressure and the head and upper body are elevated. As a result, there may be a need to lower the head fairly rapidly to prevent blood loss in the brain if CPR is stopped while the head is elevated but the patient is still in cardiac arrest. Typically, this means that the patient's head and upper body may be elevated at a different rate than it is lowered. For example, the patient's head may be elevated over a period of between about 2 and 60 seconds, and typically between about 5 and 20 seconds. The patient's head may be lowered between about 1 and 10 seconds, and typically between about 1-5 seconds.

The elevation devices described herein may include and/or be used in conjunction with one or more physiological sensors to determine rates and timing of elevation and lowering. For example, if the end tidal $CO_2$ ($ETCO_2$) is being measured as a non-invasive indicator of circulation, the head and thorax could be elevated towards the desired target height but that process could be slowed or stopped once the $ETCO_2$ levels off or starts to decrease, indicating that further elevation would potentially reduce overall circulation within the patient. In another example, the patient on the elevation device may be monitored using an electrocardiogram (ECG) or a means to non-invasively assess ICP or cerebral perfusion or cerebral perfusion pressure, either directly or indirectly. The ECG may detect a regular heart rhythm even if the individual has no palpable pulse. Based on this detection of the regular heart rhythm, it may be determined to stop the performance of chest compressions and to promptly lower the head, heart, and shoulders to the horizontal plane. This ensures that when CPR is stopped and it is observed that there is a regular heart rhythm but there is an absence of a palpable pulse (a condition termed pulseless electrical activity), the head, heart, and shoulders are rapidly lowered so that excessive blood does not drain from the brain while attempting to lower the patient. In other words, although the patient may have a stable or regular heart rhythm so that CPR could potentially be stopped, the patient's heart may not be strong enough to keep pumping blood "uphill" and so the patient is quickly lowered so that the blood in the brain does not immediately drain. It will be appreciated that other sensors [e.g. blood pressure, end tidal $CO_2$, cerebral oximetry and flow and pressure, cerebral or thoracic or carotid artery impedance, etc.] may be used in conjunction with the elevation device to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

In some embodiments, the elevation and/or de-elevation declination speeds of an elevation device may be regulated by a controller. For example, the controller may adjust an actuation speed of a motor or other elevation mechanism to raise or lower an upper support surface of the elevation device within the necessary time frame. In some embodiments, a hydraulic lift mechanism may be used to elevate the upper support surface. In such embodiments, the hydraulic lift mechanism may be gradually pressurized to elevate the upper support surface. To quickly lower the upper support surface, a pressure valve may be opened allowing the pressure within the hydraulic lift mechanism to quickly drop, allowing the upper support to be lowered to a generally supine position very rapidly. Other lock and release handle mechanical devices could also be used to slowly elevate and rapidly lower the head and upper thorax as medically needed.

In one embodiment, an elevation device may include an elevation support having a generally planar surface in general alignment with a horizontal plane. The generally planar surface may be positioned under an individual to support the individual in a supine position. A portion of the generally planar surface may be configured to be bent upward to elevate the head, shoulders, and/or heart of an individual at an angle of between about 10 and 60 degrees above the horizontal plane. In some embodiments, the generally planar surface may be configured to bend upward at a position in line with the individual's waist to elevate the entire upper body. In other embodiments, the generally planar surface may be configured to bend at a higher position to elevate just the head, shoulders, and/or heart of the individual. In some embodiments, the generally planar surface is configured to bend at multiple locations to allow the heart and head to be elevated at different angles. As just one example, the fulcrum of the bend may be at the waist and/or mid-back level. In some embodiments, the generally planar surface includes a mounting point that is configured to receive a CPR assist device, such as a manual and/or automatic chest compression and/or decompression device, such that the CPR assist device is positioned in alignment with the heart of the individual. In some embodiments, the CPR assist device may be permanently attached and/or assembled with the elevation device such that the elevation device and the CPR assist device are a single unit. The elevation device may further include and/or be used in conjunction with an ITD and/or other mechanism for intrathoracic pressure regulation.

Figure 5A:
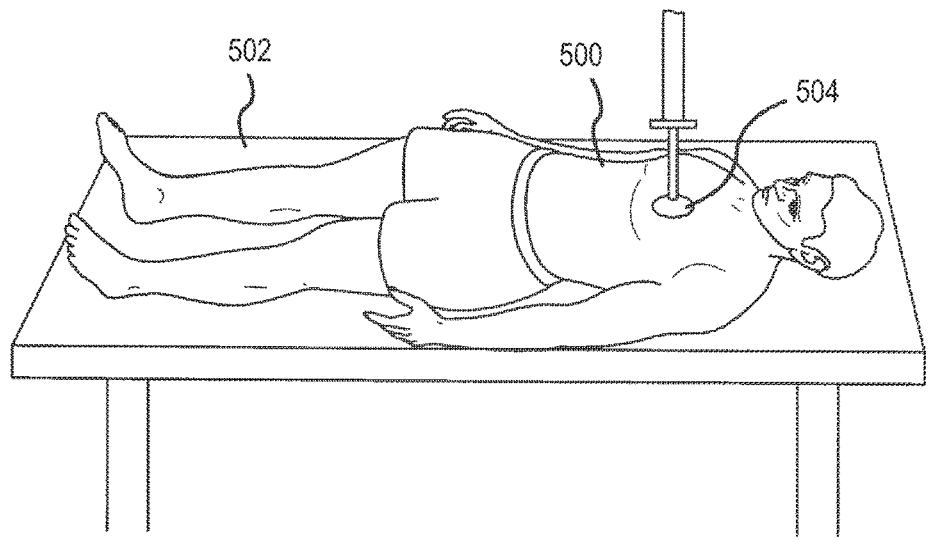
FIG. 5A is a schematic of a patient receiving CPR in a supine configuration according to embodiments.
Figure 5B:
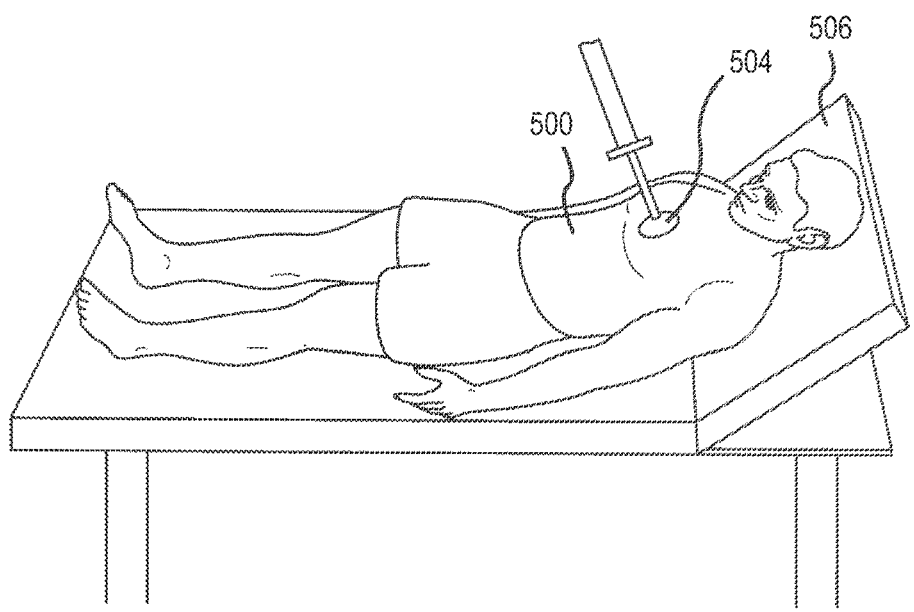
FIG. 5B is a schematic of a patient receiving CPR in a head and thorax up configuration according to embodiments.

Turning now to FIG. 5A, a demonstration of the standard supine (SUP) CPR technique is shown. Here, a patient 500 is positioned horizontally on a flat or substantially flat surface 502 while CPR is performed. CPR may be performed by hand and/or with the use of an automated CPR device and/or ACD+CPR device 504. In contrast, a head and thorax up (HUP) CPR technique is shown in FIG. 5B. Here, the patient 500 has his head and thorax elevated above the rest of his body, notably the lower body. The elevation may be provided by one or more wedges or angled surfaces 506 placed under the patient's head and/or thorax, which support the upper body of the patient 500 in a position where both the head and thorax are elevated, with the head being elevated above the thorax. HUP CPR may be performed with ACD alone, with the ITD alone, with the ITD in combination with conventional standard CPR alone, and/or with ACD+ITD together. Such methods regulate and better control intrathoracic pressure, causing a greater negative intrathoracic pressure during CPR when compared with conventional manual CPR. In some embodiments, HUP CPR may also be performed in conjunction with extracorporeal membrane oxygenation (ECMO).

Figure 6:
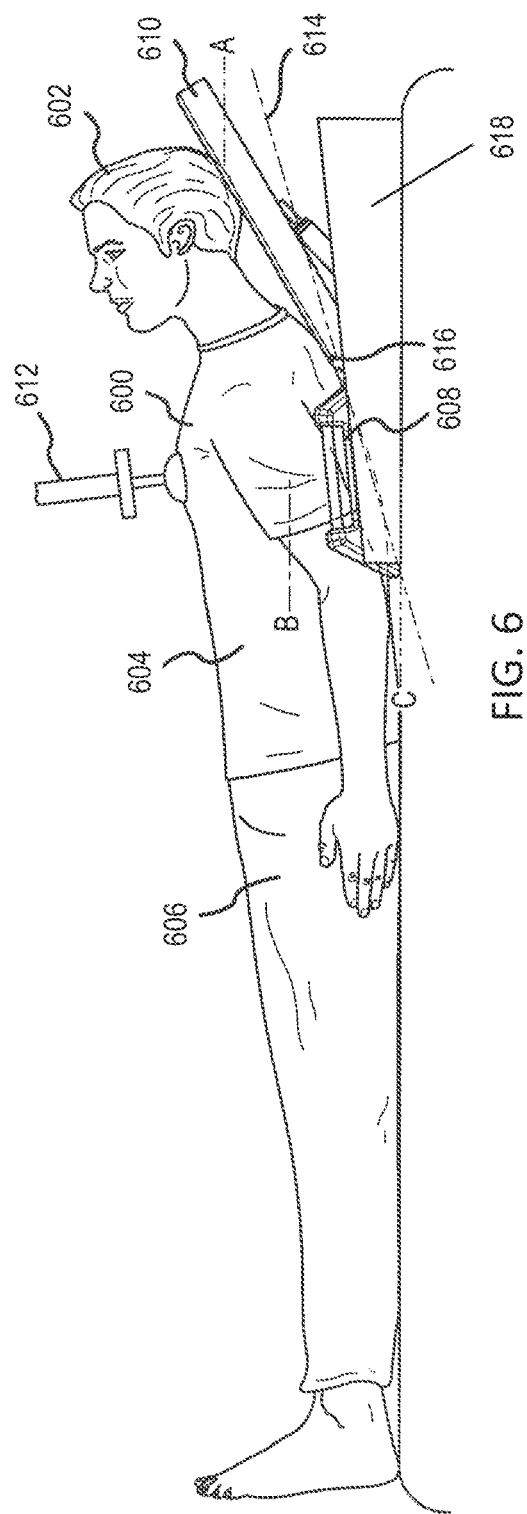
FIG. 6 shows a patient receiving CPR in a head and thorax up configuration according to embodiments.

FIG. 6 depicts a patient 600 having the head 602 and thorax 604 elevated above the lower body 606 using elevation device 618. This may be done, for example, by using one or more supports of elevation device 618 to position the patient 600 appropriately. Here thoracic support 608 is positioned under the thorax 604 to elevate the thorax 604 to a desired height B, which is typically between about 6 cm and 8 cm. Upper support 610 is positioned under the head 602 such that the head 602 is elevated to a desired height A, typically between about 10 cm and 30 cm. Thus, the patient 600 has its head 602 at a higher height A than thorax at height B, and both are elevated relative to the flat or supine lower body at height C. Typically, the height of thoracic support 608 may be achieved by the thoracic support 608 being at an angle of between about 0° and 15° from a substantially horizontal plane with which the patient's lower body 606 is aligned. Upper support 610 is often at an angle between about 15° and 45° above the substantially horizontal plane. In some embodiments, one or both of the upper support 610 and thoracic support 608 is adjustable such that an angle and/or height may be altered to match a type a CPR, ITP regulation, and/or body size of the individual. As shown here, thoracic plate or support 608 is fixed at an angle, such as between 0° and 15° from a substantially horizontal plane. The upper support 610 may adjust by pivoting about an axis 614. This pivoting may involve a manual adjustment in which a user pulls up or pushes down on the upper support 610 to set a desired position. In other embodiments, the pivoting may be driven by a motor or other drive mechanism. For example, a hydraulic lift coupled with an extendable arm may be used. In other embodiments, a screw or worm gear may be utilized in conjunction with an extendable arm or other linkage. Any adjustment or pivot mechanism may be coupled between a base of the support structure and the upper support 610. In some embodiments, a neck support may be positioned on the upper support to help maintain the patient in a proper position.

As one example, the lower body 606 may define a substantially horizontal plane. A first angled plane may be defined by a line formed from the patient's chest 604 (heart and lungs) to his shoulder blades. A second angled plane may be defined by a line from the shoulder blades to the head 602. The first plane may be angled about between 5° and 15° above the substantially horizontal plane and the second plane may be at an angle of between about 15° and 45° above the substantially horizontal plane. In some embodiments, the first angled plane may be elevated such that the heart is at a height of about 4-8 cm above the horizontal plane and the head is at a height of about 10-30 cm above the horizontal plane.

The type of CPR being performed on the elevated patient may vary. Examples of CPR techniques that may be used include manual chest compression, chest compressions using an assist device such as chest compression device 612, either automated or manually, ACD CPR, a load-distributing band, standard CPR, stutter CPR, and the like. Such processes and techniques are described in U.S. Pat. Pub. No. 2011/0201979 and U.S. Pat. Nos. 5,454,779 and 5,645,522, all incorporated herein by reference. Further, various sensors may be used in combination with one or more controllers to sense physiological parameters as well as the manner in which CPR is being performed. The controller may be used to vary the manner of CPR performance, adjust the angle of inclination, the speed of head and thorax rise and descent, provide feedback to the rescuer, and the like. Further, a compression device could be simultaneously applied to the lower extremities or abdomen to squeeze venous blood back into the upper body, thereby augmenting blood flow back to the heart. Further, a compression-decompression band could be applied to the abdomen that compresses the abdomen only when the head and thorax are elevated either continuously or in a pulsatile manner, in synchrony or asynchronously to the compression and decompression of the chest. Further, a rigid or semi-rigid cushion could be simultaneously inserted under the thorax at the level of the heart to elevate the heart and provide greater back support during each compression.

Additionally, a number of other procedures may be performed while CPR is being performed on the patient in the torso-elevated state. One such procedure is to periodically prevent or impede the flow in respiratory gases into the lungs. This may be done by using a threshold valve, sometimes also referred to as an impedance threshold device (ITD) that is configured to open once a certain negative intrathoracic pressure is reached. The invention may utilize any of the threshold valves or procedures using such valves that are described in U.S. Pat. Nos. 5,551,420; 5,692,498; 5,730,122; 6,029,667; 6,062,219; 6,810,257; 6,234,916; 6,224,562; 6,526,973; 6,604,523; 6,986,349; and 7,204,251, the complete disclosures of which are herein incorporated by reference.

Another such procedure is to manipulate the intrathoracic pressure in other ways, such as by using a ventilator or other device to actively withdraw gases from the lungs. Such techniques as well as equipment and devices for regulating respirator gases are described in U.S. Pat. Pub. No. 2010/0031961, incorporated herein by reference. Such techniques as well as equipment and devices are also described in U.S. patent application Ser. Nos. 11/034,996 and 10/796,875, and also U.S. Pat. Nos. 5,730,122; 6,029,667; 7,082,945; 7,410,649; 7,195,012; and 7,195,013, the complete disclosures of which are herein incorporated by reference.

In some embodiments, the angle and/or height of the head and/or heart may be dependent on a type of CPR performed and/or a type of intrathoracic pressure regulation performed. For example, when CPR is performed with a device or device combination capable of providing more circulation during CPR, the head may be elevated higher, for example 10-30 cm above the horizontal plane (10-45 degrees) such as with ACD+ITD CPR. When CPR is performed with less efficient means, such as manual conventional standard CPR, then the head may be elevated less, for example 10-20 cm or 10 to 20 degrees.

A variety of equipment or devices may be coupled to or associated with the structure used to elevate the head and torso to facilitate the performance of CPR and/or intrathoracic pressure regulation. For example, a coupling mechanism, connector, or the like may be used to removably couple a CPR assist device to the structure. This could be as simple as a snap fit connector to enable a CPR assist device to be positioned over the patient's chest. Examples of CPR assist devices that could be used with the elevation device (either in the current state or a modified state) include the Lucas device, sold by Physio-Control, Inc. and described in U.S. Pat. No. 7,569,021, the entire contents of which is hereby incorporated by reference, the Defibtech Lifeline ARM—Hands-Free CPR Device, sold by Defibtech, the Thumper mechanical CPR device, sold by Michigan Instruments, automated CPR devices by Zoll, such as the AutoPulse, as also described in U.S. Pat. No. 7,056,296, the entire contents of which is hereby incorporated by reference, the Weil Mini Chest Compressor Device, such as described in U.S. Pat. No. 7,060,041 (Weil Institute), and the like. Additional devices that could be coupled to the structure include an external defibrillator/pacing system and physiological sensors to assess the patient's physiological status. The structure thereby serves as a means to elevate the head and thorax, provide CPR, and as a workstation for other tools and equipment to facilitate the resuscitation effort.

In some embodiments, an elevation device, such as those described in U.S. application Ser. No. 15/850,827 and U.S. application Ser. No. 15/601,494, the entire contents of which are hereby incorporated by reference, may be programmed to perform sequential elevation HUP CPR and/or used in the treatment of other low blood flow conditions as described herein. For example, an elevation device may include a base and an upper support coupled with the base. The upper support may be configured to elevate an individual's heart, shoulders, and head relative to horizontal. In some embodiments, the upper support may include a single support surface that is configured to elevate the heart and head at a single angle, such as by bending the patient at or near the waist. In other embodiments, the upper support may include multiple support surfaces that may elevate the heart and head at different angles. The upper support may include an adjustment mechanism that is configured to adjust a degree of elevation of the upper support. For example, a motor or other actuator may be used to drive the angular and/or height adjustment of the upper support relative to the base. In some embodiments, a controller may be coupled with the adjustment mechanism and may be used to control the elevation of the upper support. For example, the controller may execute instructions that determine when and to what degree the adjustment mechanism adjusts the elevation position of the upper support. This may be based off of timing instructions that are derived from empirical studies and/or the elevation may be controlled based on one or more physiological parameters measured by one or more sensors that are in communication with the controller. For example, blood flow sensors, blood pressure sensors, end tidal $CO_2$ sensors, cerebral oximetry sensors, and/or sensors that monitor other physiological parameters that correlate directly or indirectly with cardio-pulmonary circulation and perfusion may be connected to the controller such that the controller may make adjustments in elevation degree and/or timing based on the sensed parameters.

The elevation device may also include a chest compression device, such as an automated chest compression device. In some embodiments, the chest compression device may be a load distributing band, a piston-based chest compression device, a combination of a load distributing band and an active decompression device, and/or other automated and/or manually actuated chest compression device. In some embodiments, the chest compression device may be configured to actively decompress the individual's chest between each compression such that the chest compression device may be used in the performance of ACD-CPR. In some embodiments, the controller may be coupled with the chest compression device such that the controller may control a rate and/or timing of the chest compressions being delivered to an individual according to the sequential elevation procedures described herein. The compression depth, decompression depth, rate of compression and decompression, and/or duty cycle may be varied based on a particular individual and/or based on measurements from the physiological sensors. In some embodiments, the CPR may be delivered continuously or with pauses for a positive pressure breath and/or with 3-5 short and intentional pauses at the start of CPR to allow for reperfusion injury protection. In each of these examples, the head and thorax can also be lowered if clinically required, in some cases rapidly in less than 6 seconds.

As an individual's head is elevated using an elevation device, such as elevation device 618, the individual's thorax is forced to constrict and compress, which causes a more magnified thorax migration during the elevation process. This thorax migration may cause the misalignment of a chest compression device, which leads to ineffective, and in some cases, harmful, chest compressions. It can also cause the head to bend forward thereby potentially restricting the airway. Thus, maintaining the individual in a proper position throughout elevation, without the compression and contraction of the thorax, is vital to ensure that safe and effective CPR can be performed. Embodiments of the elevation devices described herein provide upper supports that may expand and contract, such as by sliding along a support frame to permit the thorax to move freely upward and remain elongate, rather than contract, during the elevation process. For example, the upper support may be supported on rollers with minimal friction. As the head, neck, and/or shoulders are lifted, the upper support may slide away from the thoracic compression, which relieves a buildup of pressure on the thorax and minimizes thoracic compression and migration. Additionally, such elevation devices are designed to maintain optimal airway management of the individual, such as by supporting the individual in the sniffing position throughout elevation. In some embodiments, the upper supports may be spring biased in a contraction direction such that the only shifting or expansion of the upper support is due to forces from the individual as the individual is subject to thoracic shift. Other mechanisms may be incorporated to combat the effects of thoracic shift. For example, adjustable thoracic plates may be used that adjust angularly relative to the base to ensure that the chest compression device remains properly aligned with the individual's sternum. Typically, the thoracic plate may be adjusted between an angle of between about 0° and 8° from a substantially horizontal plane. In some embodiments, as described in greater detail below, the adjustment of the thoracic plate may be driven by the movement of the upper support. In such embodiments, a proper amount of thoracic plate adjustment can be applied based on the amount of elevation of the upper support.

In traditional CPR the patient is supine on an underlying flat surface while manual or automated CPR is implemented. During automated CPR, the chest compression device may migrate due to limited stabilization to the underlying flat surface, and may often require adjustment due to the migration of the device and/or body migration. This may be further exaggerated when the head and shoulders are raised. The elevation devices described herein offer a more substantial platform to support and cradle the chest compression device, such as, for example, a LUCAS device, providing stabilization assistance and preventing unwanted migratory motion, even when the upper torso is elevated. The elevation devices described herein provide the ability to immediately commence CPR in the lowered/supine position, continuing CPR during the gradual, controlled rise to the "Head-Up/Elevated" position. Such elevation devices provide ease of patient positioning and alignment for automated CPR devices. Correct positioning of the patient is important and readily accomplished with guides and alignment features, such as a shaped shoulder profile, a neck/shoulder support, a contoured thoracic plate, as well as other guidelines and graphics. The elevation devices may incorporate features that enable micro adjustments to the position of an automated CPR device position, providing control and enabling accurate placement of the automated CPR device during the lift process. In some embodiments, the elevation devices may establish the sniffing position for intubation when required, in both the supine position and during the lifting process. Features such as stationary pads and adjustable cradles may allow the reduction of neck extension as required while allowing ready access to the head for manipulation during intubation.

In some embodiments, the chest compression device 612 and the elevation device 618 may share a common power source. For example, the chest compression device 612 or the elevation device 618 may include a power source, such as a power cord and/or battery. The non-powered device may then plug into the other device to share the power source. In other embodiments, the chest compression device 612 and the elevation device 618 may be formed as a single device, with the elevation mechanism of the elevation device 618 and the chest compression device 612 both being wired to a single power source.

Additionally, the chest compression device 612 and/or elevation device 618 may be configured to communicate with other devices, such as computers, mobile devices like mobile phones and tablet computers, e-readers, other medical equipment, such as electrocardiographs and defibrillators, and the like. To enable such communication, one or more wired and/or wireless communication networks may be established. For example, various data cables may be used to communicatively couple the chest compression device 612 and/or elevation device 618 to one or more remote devices. In some embodiments, the chest compression device 612 and/or elevation device 618 may include a wireless communications interface that is configured to communicate with one or more remote devices using WiFi, Bluetooth, 3G, 4G, LTE, and/or other wireless communications protocols.

In some embodiments, the elevation device 618 may be coupled with a stretcher-like device for transport that has features that allow the heart and head to be elevated above the plane of the abdomen and lower extremities. For example, the stretcher or stretcher-like device may include rails or other rigid or semi-rigid support members that may be used to secure the elevation device 618 and/or the chest compression device 612 to the stretcher. The elevation device 618 and/or the chest compression device 612 may be coupled to the support members using clamps cables, and/or other securement mechanisms that may ensure the elevation device 618 and/or the chest compression device 612 do not shift relative to the stretcher. In some embodiments, the elevation device serve as a stretcher as well.

In the embodiment shown in FIG. 7, an elevation device may take the form of a wedge 700 or other pre-formed device. The wedge 700 may be configured to be placed on a support surface, such as a floor, stretcher, bed, ground, etc., and under an individual to raise the individual's head, shoulders, and heart. In some embodiments, the wedge 700 may be designed such that a portion of the wedge 700 that is designed to support the area of the chest around the patient's heart is at a different, oftentimes lower, angle than a portion of the wedge 700 that supports the shoulders and head. For example, the portion of the wedge 700 that supports the heart may be at an angle of between about 0° and 15° relative to horizontal such that the heart is elevated between about 1 cm to 10 cm or 2 cm and 10 cm (typically about 10 cm) above the support surface. The portion of the wedge 700 that supports the shoulders and head may be at an angle of between about 15° and 45° relative to horizontal such that the shoulders and/or head are elevated between about 10 cm and 30 cm (typically about 20 cm) above the support surface. Further, the portion of the pre-formed device under the chest may be rigid so that chest compressions are more effective as the chest is compressed rather than the structure under the chest (e.g. a mattress).

In some embodiments, the wedge 700 may include a depression 702 that is configured to receive the patient's head. The depression 702 allows the occiput portion of the head to be positioned downward, opening the patient's airways. In some embodiments, some or all of the wedge 700 may be formed with a curved profile such that a body of the wedge curves downward from its edges along a length of the wedge 700. This shape helps the wedge 700 more closely conform to a shape of the patient's back. In some embodiments, the wedge 700 may include a mounting support 704 on each side of the wedge 700 that allows a chest compression device (not shown) to be coupled with the wedge 700 at a position that is generally aligned with the patient's heart.

The wedge 700 may be formed of a semi rigid material, such as a foam or other synthetic material. The wedge 700 may be a semi-rigid material that allows for some flexing. This flexing may be particularly helpful when the wedge 700 is used in conjunction with a chest compression device, as the flexibility ensures that the right amount force applied to the patient's chest. For example, a central portion of the wedge 700 may flex in the presence of excessive force, thereby acting as a flexible back plate to absorb some of the force. For example, as a plunger of a chest compression device is pressed into the patient's chest, some force is transmitted through the patient to the wedge 700. The wedge 700 may be configured to bend away from the patient if this transferred force exceeds a threshold. This allows for the delivery of compression at the appropriate depth for patients with differing chest wall sizes and the stiffness of their skeletal structure and/or their musculature. This helps prevent broken ribs and/or other injuries to the patient caused by too much force being applied to the patient's chest, as the flexing back plate, rather than the ribs or other body structures, absorbs a significant portion of the excess force. It should be appreciated that the portion of the wedge 700 under the heart and thorax could also contain force, pressure, impedance, and/or position sensors to provide feedback to the chest compression device, assuring the proper compression depth and force are delivered, even though the amounts needed to provide the proper CPR may differ from patient to patient and may change over time.

In some embodiments, a contact surface of the wedge 700 may be textured and/or coated with and/or formed from a non-slip material to help prevent the patient from sliding downward, thereby maintaining the patient in a desired treatment position. In some embodiments, the wedge 700 may include a neck pad, armpit flaps, and/or other positioning aids to both help properly positioning a patient on the wedge and to ensure that the patient remains in the correct treatment position. For example, a neck pad may be provided that supports the individual's neck. The neck pad may be configured to support the individual's spine in a region of the individual's C7 and C8 vertebrae. Such positioning may help maintain the patient in the sniffing position to maintain the patient's airway in a proper position for endotracheal intubation. In such a position, the neck is flexed and the head extended, allowing for patient intubation, if necessary, and airway management.

In some embodiments, the chest compression device and wedge 700 may be configured to communicate with each other and/or with remote devices. For example, one or more network or other data cables and/or wireless interfaces may couple processors and/or sensors of each device to one another and/or with remote devices such as computers, mobile devices like mobile phones and tablet computers, e-readers, other medical equipment, such as electrocardiographs and defibrillators, and the like. Data regarding the CPR rate, force applied to the patient, and/or other data may be measured and shared between the devices. Additionally, data from physiological sensors may be shared with the chest compression device. This physiological data, such as ICP, blood flow data, blood pressure, intrathoracic pressure measurements, and the like may be used to control the various parameters such as chest compression depth and/or force and the like.

In some embodiments, the wedge 700 may be coupled with a stretcher-like device for transport that has features that allow the heart and head to be elevated above the plane of the abdomen and lower extremities. For example, the stretcher or stretcher-like device may include rails or other rigid or semi-rigid support members that may be used to secure the wedge 700 and/or a chest compression device to the stretcher. The wedge 700 and/or the chest compression device 32 may be coupled to the support members using clamps, cables, and/or other securement mechanisms that may ensure the wedge 700 and/or the chest compression device do not shift relative to the stretcher.

In some embodiments, the wedge 700 may include a stowable shelf (not shown). The stowable shelf may be configured to be maintained in a stowed position in which most or all of the shelf is disposed within an interior of the wedge 700, with only a handle and/or outer surface of the stowable shelf remaining exposed exteriorly of the elevation device. The stowable shelf may be extended outward into an extended position in which all or a large portion of the stowable shelf protrudes from a side of the wedge 700. This protruding portion may be used by medical personnel as a support for their knees so that the rescuer may be elevated relative to the ground and positioned properly for administering CPR. For example, the stowable shelf may be configured to elevate the rescuer to a height of between about 2 and 4 inches relative to the ground. Oftentimes, the stowable shelf may be positioned on a roller track or other sliding mechanism that enables the stowable shelf to be manipulated between the stowed position and the extended position.

Figure 8A:
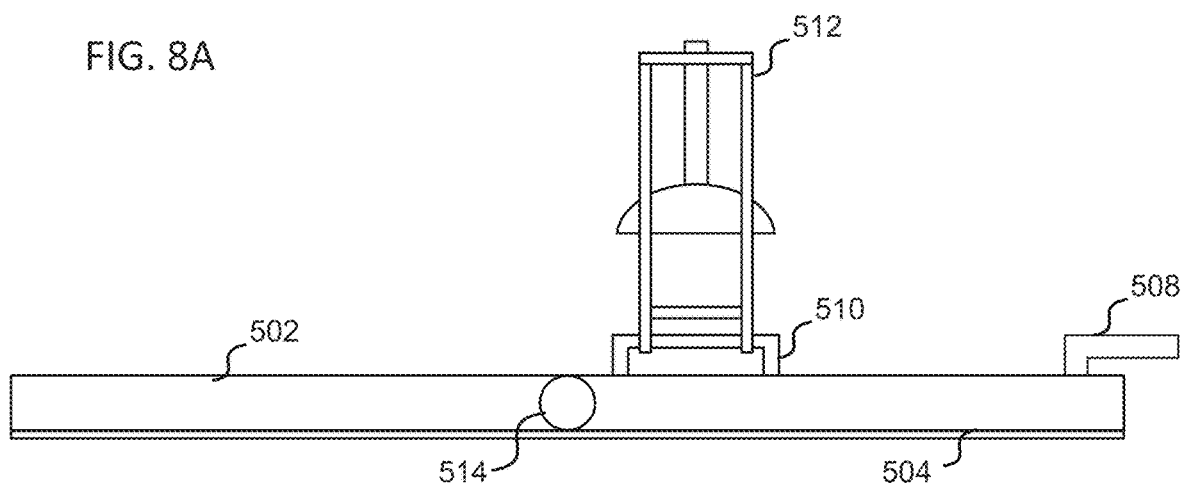
FIG. 8A depicts an elevation device in a stowed position according to embodiments.

FIGS. 8A-10C illustrate embodiments of simplified elevation devices according to the invention. Turning first to FIG. 8A, an elevation device 800 is shown in a stowed position. Elevation device 800 may be configured to be supported by a generally flat surface, such as a floor, the ground, a stretcher, a table, a bed, and/or other generally flat, supportive surface. The elevation device 800 may be configured to elevate the entire upper body of an individual, bending the individual at the waist. Elevation device 800 includes two support surfaces that are moveable relative to one another. A first support surface 802 may be generally aligned with a first plane and may be configured to support the individual's lower body at a position below the individual's waist. In some embodiments, the first support surface 802 may be entirely flat, and thus completely aligned with a first plane, while in other embodiments, the first support surface 802 may have a contoured profile that is largely, but not entirely, aligned with a single plane. The first plane may be aligned with a horizontal plane or at a slight angle (between about 0 and 5 degrees) above the horizontal plane. The first support surface 802 may be pivotally coupled with a second support surface 804 that is generally aligned with a second plane. The second support surface 804 may be similar to the upper supports described elsewhere herein. A pivot point 814 may couple the two support surfaces together at a position proximate an individual's waist. The second support surface 804 may be configured to be positioned under and to support the entirety of the individual's upper body, including the heart, shoulders, and head. The second support surface 804 is angularly positionable relative to the first support surface 802 such that an angle of the second plane may be adjusted. When pivoted, the second support surface 804 may be raised to elevated the individual's upper body as shown in FIG. 8B. For example, the second support surface 804 may be pivoted between about 5 and 45 degrees above the first support surface 802 and/or the horizontal plane to sufficiently elevate the individual's head, shoulders, and heart relative to the rest of the patient's body.

In some embodiments, the first support surface 802 and/or the second support surface 806 may have a curved profile such that a medial section of the portion of the support surface is lower relative to end sections of the portion of the support surface. Such a profile may allow the support surface to more closely match the contour of an individual's back. Additionally, the curved profile may make the support surface flexible. This flexibility helps when the elevation device 800 is used in conjunction with a chest compression device, as the flexibility ensures that the right amount force applied to the patient's chest. For example, a central portion of the support surface may flex in the presence of excessive force, thereby acting as a flexible backplate to absorb some of the force. For example, as a plunger of a chest compression device is pressed into the patient's chest, some force is transmitted through the patient to the support surface. The support surface may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing backplate, rather than the ribs or other body structures, absorbs a significant portion of the excess force. In another example the compression device also actively decompresses the chest back to or above the resting chest position. Such a head up CPR device design is particularly useful when the elevation device 800 is used in conjunction with a chest compression device 812 such as the Lucas device, sold by Physio-Control, Inc. and/or the Zoll AutoPulse. However, it will be appreciated that the flexible support surface may be used in conjunction with any of the embodiments of elevation devices described herein. It should be appreciated that the portion of the elevation device 800 under the heart and thorax could also contain force, pressure, impedance, and/or position sensors to provide feedback to the chest compression device 812, assuring the proper compression depth and force are delivered, even though the amounts needed to provide the proper CPR may differ from patient to patient and may change over time.

In some embodiments, a contact surface of the first support surface 802 and/or the second support surface 804 may be textured and/or coated with and/or formed from a non-slip material to help prevent the patient from sliding downward during elevation of the second support surface 804, thereby maintaining the patient in a desired treatment position. In some embodiments, a neck pad, head cradle, arm pit flaps, and/or other positioning aids may be included on the first support surface 802 and/or the second support surface 804 to both aid in properly positioning a patient on the elevation device 800 and to ensure that the patient remains in the correct treatment position throughout the elevation and lowering of the patient's upper body. For example, a neck pad may be provided that supports the individual's neck. The neck pad may be configured to support the individual's spine in a region of the individual's C7 and C8 vertebrae. Such positioning may help maintain the patient in the sniffing position to maintain the patient's airway in a proper position for endotracheal intubation. In such a position, the neck is flexed and the head extended, allowing for patient intubation, if necessary, and airway management. In some embodiments, a position and/or angle of the neck pad and/or a different head support, such as a head cradle or head support pad, may be adjustable. This allows for better airway management as well as better support of the patient's head, and allows the elevation device 800 to be usable with patients of various sizes and flexibility levels. For example, a patient with a particularly stiff neck may need to be positioned and/or supported differently than a patient having a neck with normal levels of flexibility. The neck pad and/or head support may be configured to raise and/or lower relative to the second support surface 804 to adjust the height of the patient's head and/or neck. For example, second support surface 804 may have an opening that is configured to receive the patient's head. The head support may be in the form of a cradle that is coupled with the second support surface 804 using cables, rods, and/or other supports. The supports may be extended and/or retracted to raise and/or lower the cradle. In other embodiments, the head support may include an inflatable pad that contacts a portion of the patient's head. The pad may be inflated to raise the head and deflated to lower the head.

Elevation device 800 may include one or more support mechanisms that are configured to maintain the second support surface at a desired elevation. For example, elevation device 800 may include one or more support posts 806 that are each configured to maintain the second support surface 804 at an elevated position relative to the first support surface 802. Each support post 806 may be in the form of a kickstand, such as a top board prop of a grand piano that maintains the top board in an open position or like a prop rod that holds an automobile hood open. The support post 806 may be extended or otherwise positioned upward in engagement with an underside of the second support surface 804 to maintain the second support surface 804 at a desired elevation. For example, an underside of the second support surface 804 may include one or more receptacles that are configured to receive and secure an end of the support post 806. In some embodiments, multiple receptacles may be provided at different positions on the underside of the second support surface 804 such that the support post 806 may be used to elevate the second support surface 804 at various heights/angles.

In some embodiments, support post 806 may be hinged. A hinged support post 806 may be lockable in an extended position that allows the second support surface 804 to be raised relative to the first support surface 802 and locked into place. As just one example, a hinge of the hinged support post 806 may be locked in a straight, extended positon and/or may include a sleeve that may be positioned over the hinge to prevent the hinge from pivoting, thereby maintaining the second support surface 804 at a desired position. In other embodiments, the support post 806 may be a telescoping pole, such as a rod formed by a number of nesting rods of various diameters. Friction between the rods may act to maintain the second support surface at a desired height. In some embodiments, the telescoping pole may include a lock mechanism, such as a clamp or sleeve that prevents the telescoping pole from contracting under the weight of the individual's upper body.

Other support posts 806 may be in the form of pneumatic and/or hydraulic struts that utilize pressurized fluids to maintain the second support surface 804 at a desired elevation. Each of these support posts 806 may be disengaged to lower the second support surface 804. For example, one end of a gas strut may be positioned at a pivot point on a base of elevation device 800 while the other end is fixed to an underside of the second support surface 804. The strut may be extended or contracted as the elevation of the second support surface 804 changes.

Depending on the type of support post 806 used, the second support surface 804 may be lowered with or without downward force being applied by an operator of the elevation device 800. For example, if the support post 806 is in the form of a kickstand, once the kickstand is disengaged, the second support surface 804 may lower under the weight of the patient's head. In other embodiments, such as those using telescoping, pneumatic, and/or hydraulic support posts 806, the operator of the elevation device 800 may need to press down on the second support surface 804 to lower it. In some embodiments using pneumatic and/or hydraulic support posts 806, the second support surface 804 may be lowered by depressurizing the support post 806, such as by actuating a pressure relief valve.

To aid in the raising and lowering of the second support surface 804, the second support surface 804 may include one or more handles 808. For example, the handles 808 may be provided on one or more sides of the second support surface 804 and/or along a top edge of the second support surface 804. It will be appreciated that while described using manual means for elevation, elevation device 800 may be fitted with controllers, motors, threaded rods, lead screws, pneumatic and/or hydraulic actuators, motor driven telescopic rods, other elevation mechanisms, and/or combinations thereof. In some embodiments, the motors may be coupled with a controller or other computing device. The controller may communicate with one or more input devices such as a keypad. This allows a user to select an angle and/or height of the heart and/or head to be raised using the motor and/or other actuator. Additionally, the controller may be coupled with one or more sensors, such as flow and pressure sensors. Sensor inputs may be used to automatically control the motor and angle of the supports based on flow and pressure measurements. A type of CPR and/or ITP regulation may also be controlled using these and/or other sensor inputs. In some embodiments, the electro-mechanical lift mechanisms may include disengagement mechanisms that allow the elevation device 800 to be operated manually. This allows the elevation device 800 to be operable even if a power source for the electromechanical features is unavailable, such as when a battery is dead or when there is no power outlet or other power source available.

In some embodiments, the elevation device 800 may include elevation mechanisms that do not require a pivot point. As just one example, the support posts 806 may be raisable arms that are positioned underneath the second support surface 804 at a front and back of the second support surface 804. The front arms may raise slower and/or raise to a shorter height than the back arms, thus raising a back portion of the second support surface 804 to a higher elevation than a front portion.

Oftentimes, the first support surface 802 and/or the second support surface 804 include a mounting site 810 for a chest compression device 812. The mounting site 810 may allow a chest compression device 812 to be removably and/or permanently attached to the elevation device 800. The mounting site 810 may be positioned such that when coupled, the chest compression device 812 is disposed in alignment with the patient's heart and generally perpendicular (within about 5 degrees of perpendicular) with the patient's chest. In embodiments where the elevation device 800 is configured to elevate the entire upper body of a patient, the mounting site 810 may be on the second support surface 804. The chest compression device 812 may be configured to repeatedly compress the individual's chest using manual and/or electro-mechanical force. For example, the chest compression device 812 may include one or more handles that are operably coupled with a plunger. An operator of the chest compression device 812 may grasp the handles and apply downward force to the plunger to compress the patient's chest. In some embodiments, the chest compression device 812 may be an active compression/decompression device. For example, a suction cup, adhesive pad, and/or other fastening mechanism may be secured to the patient's chest. The operator may then pull up on the handle to lift the patient's chest, thereby actively decompressing the chest.

Automatic chest compression devices 812 may also be used. For example, automatic chest compression devices 812 may include a reciprocating plunger that may be actuated by a motor, solenoid, and/or other electro-mechanical actuator. In other embodiments, active decompression may be provided to the patient receiving CPR with a modified load distributing band device (e.g. modified Zoll Autopulse® band) by attaching a counter-force mechanism (e.g. a spring) between the load distributing band and the head up device or elevation device 800. Each time the band squeezes the chest, the spring, which is mechanically coupled to the anterior aspect of the band via an arch-like suspension means, is actively stretched. Each time the load distributing band relaxes, the spring recoils pulling the chest upward. The load distributing band may be modified such that between the band and the anterior chest wall of the patient there is a means to adhere the band to the patient (e.g. suction cup or adhesive material). Thus, the load distributing band compresses the chest and stretches the spring, which is mounted on a suspension bracket over the patient's chest and attached to the head up device. It will be appreciated that the above chest compression devices are merely provided as examples, and that numerous variants may be contemplated in accordance with the present invention.

In some embodiments, the second support surface 804 may be slidable and/or otherwise expandable and contractible lengthwise during elevation of the patient's upper body to maintain the patient in a correct position and to assist in preventing the patient from curling forward during the elevation process. For example, the second support surface 804 may include multiple pieces that are slidable or otherwise movable relative to one another to expand and contract to maintain the patient in a desired position. This expansion and contraction may be particular useful in embodiments with automatic chest compression devices 812, as the expansion and/or contraction may be useful in ensuring that chest compressions are delivered at a proper position and angle relative to the patient's chest. In some embodiments, the second support structure 804 may include an upper section that is slidable along a support frame to permit the thorax to move freely upward and remain elongate, rather than contract, during the elevation process. For example, the upper section may be supported on rollers with minimal friction. As the head, neck, and/or shoulders are lifted, the upper section may slide away from the thoracic compression, which relieves a buildup of pressure on the thorax and minimizes thoracic compression and migration. In some embodiments, the second support surface 804 or a portion thereof may be spring biased in a contraction direction such that the only shifting or expansion of the upper section or other component of the second support surface 804 is due to forces from the individual as the individual is subject to thoracic shift. In other embodiments, the second support surface 804 may be coupled with the first support surface 802 using telescoping rods or supports. These supports may extend and contract to move and/or otherwise adjust a position of the second support surface 804 (and the patient's head) relative to the first support surface 802. It will be appreciated by those skilled in the art that other mechanisms may be incorporated to combat the effects of thoracic shift.

In some embodiments, intrathoracic pressure management may be used during the administration of chest compressions. For example, an impedance threshold device configured to interface with the individual's airway may be attached to and/or used in conjunction with the elevation device 800.

In one embodiment, a controller may adjust an actuation speed of a motor or other elevation mechanism to raise or lower an upper support surface of the elevation device within the necessary time frame. For example, medical personnel may set a desired elevation time, such as between about 2 and 30 seconds. The controller will then operate a motor or other elevation mechanism to slowly raise the second support surface 804 from a starting elevation angle to a final elevation angle over the selected time period. The controller may also instruct the elevation mechanism to quickly lower the upper support 804 within a desired timeframe, often between about 1 and 10 seconds. In some embodiments, the controller may receive data from one or more physiological sensors and use this data to determine rates and timing of elevation and lowering. For example, the patient on the elevation device 800 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the second support surface 804. For example, once it is detected that the patient has a stable heart rhythm, the controller may alert medical personnel that chest compressions should be ceased, and may send a signal to the motor or other actuator to cause the second support surface to rapidly lower. In some embodiments, alerting medical personnel may involve producing a visual indicator, such as lighting up a light emitting diode (LED) or other light source and/or presenting a textual and/or image-based display on a screen of the elevation device 800. In one embodiment, upon detecting a stable heart rhythm, the controller may send a command to the automatic chest compression device 812 that causes the chest compression device 812 to stop the delivery of chest compressions and/or decompressions. In another embodiment, upon detecting the stable heart rhythm, the controller will alert medical personnel, who may then operate the elevation device 800 to lower the second support surface 804. It will be appreciated that other sensors may be used in conjunction with the elevation device 800 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

Figure 8B:
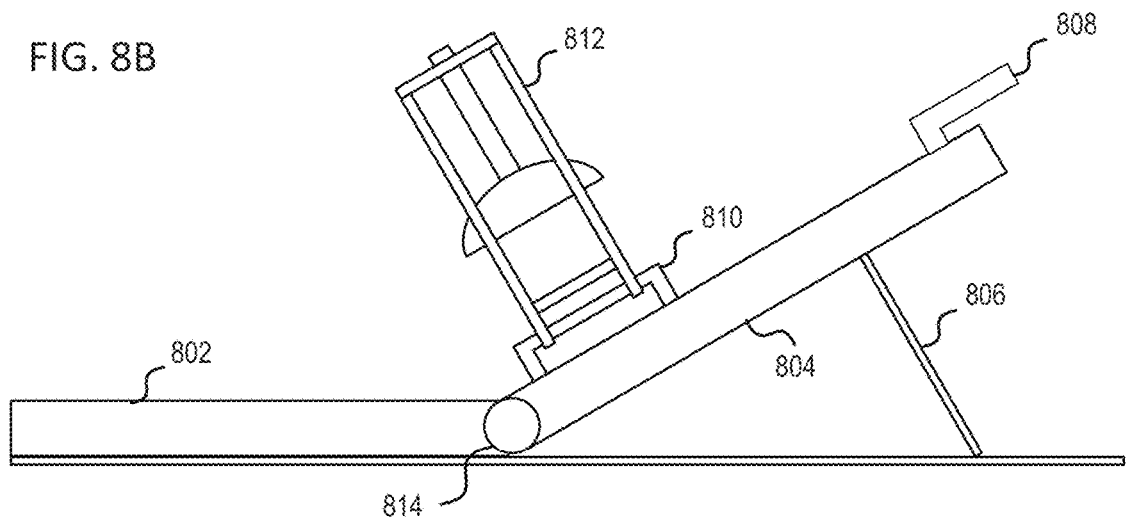
FIG. 8B depicts the elevation device of FIG. 8A in an elevated position according to embodiments.
Figure 9A:
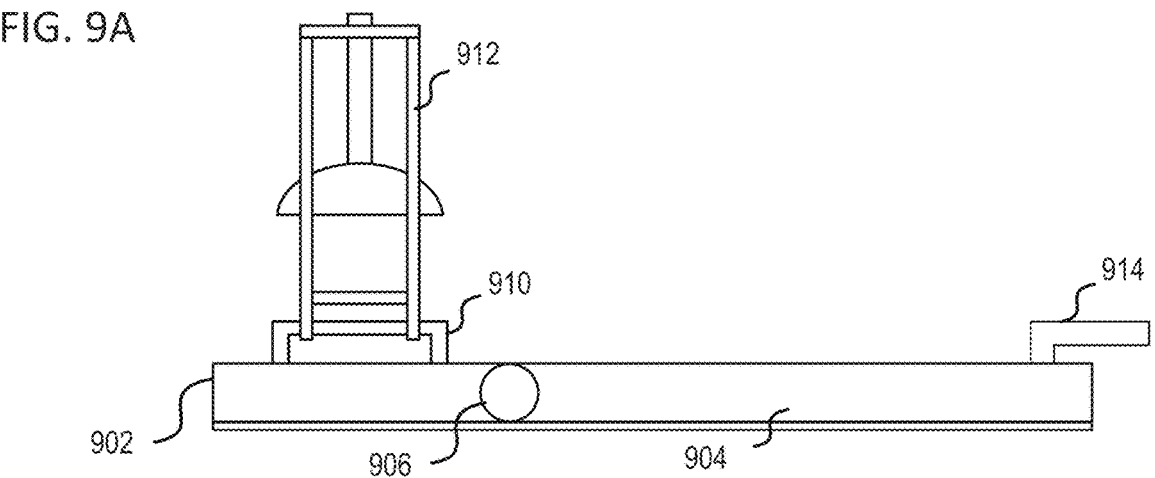
FIG. 9A depicts an elevation device in a stowed position according to embodiments.
Figure 9B:
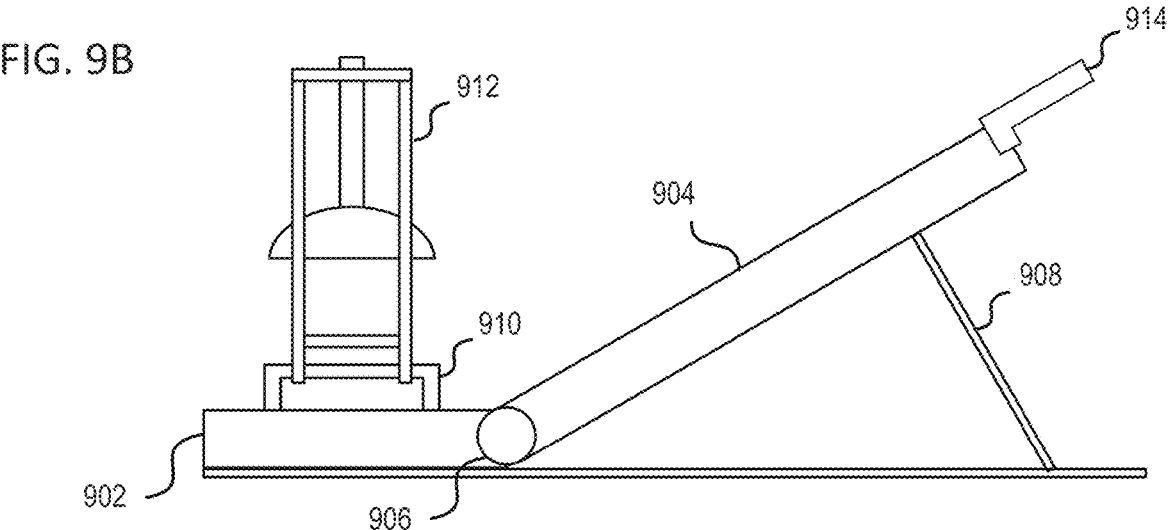
FIG. 9B depicts the elevation device of FIG. 9A in an elevated position according to embodiments.

In one embodiment shown in FIG. 9A, an elevation device 900 may be configured to elevate only a portion of the patient's upper body, including the upper chest/heart, shoulders, and head. Elevation device 900 is similar to elevation device 800 and may include similar features. Elevation device 900 includes a first support surface 902 that is configured to support at least a portion of the upper body, including the heart. Typically, the first support surface 902 extends below the individual's rib cage, and may extend to support all or a portion of the patient's lower body. In some embodiments, the first support surface 902 may be generally aligned with a horizontal plane, while in other embodiments the first support surface 902 may be aligned with a plane that is angled slightly above horizontal, such as between about 1 and 5 degrees above horizontal. A second support surface 904 may be configured to support the individual's shoulders and head, with a pivot point 906 between the first support surface 902 and the second support surface 904 at a position proximate the individual's rib cage. The second support surface 904 may be pivoted relative to the first support surface 902 to raise the patient's shoulders and head as shown in FIG. 9B. Elevation device 900 may include one or more support posts 908 similar to those described in relation to FIGS. 8A and 8B that are configured to maintain the second support surface 904 at a desired elevation. The elevation device 900 may also include a mounting site 910 for a chest compression device 912. The mounting site 910 is typically positioned on the second support surface 904 at a position in general alignment with the patient's heart. Elevation device 900 may also include one or more handles 914 to assist an operator in raising and/or lowering the second support surface. Elevation device 900 may also include one or more motors, controllers, and/or other lift mechanisms, similar to those described in relation to elevation device 500. These controllers and lift mechanisms may work in conjunction with the chest compression device 912 to raise and/or lower the patient's upper body and/or control a rate and/or timing of chest compressions as described in relation to FIGS. 8A and 8B.

Figure 10A:
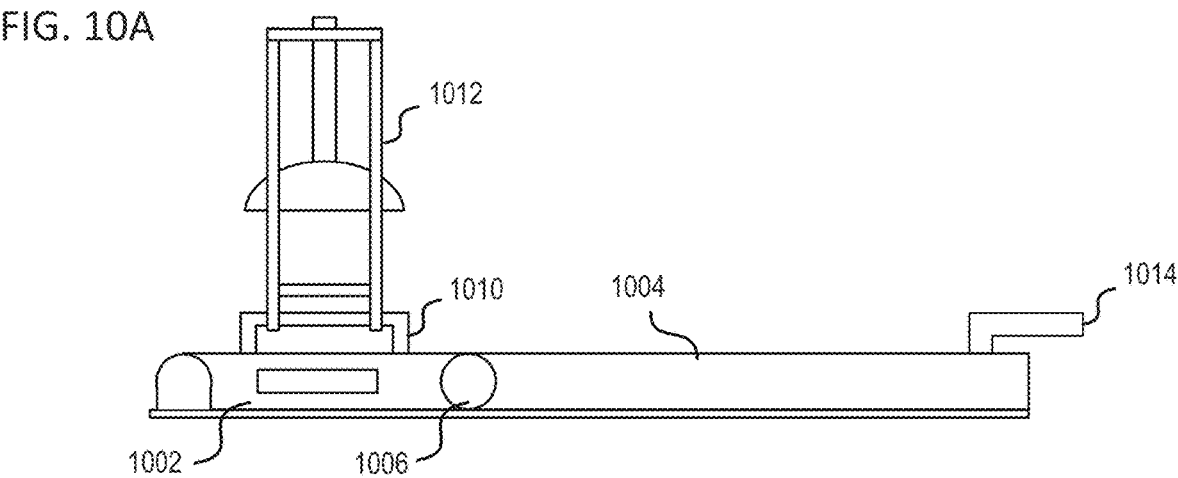
FIG. 10A depicts an elevation device in a stowed position according to embodiments.
Figure 10B:
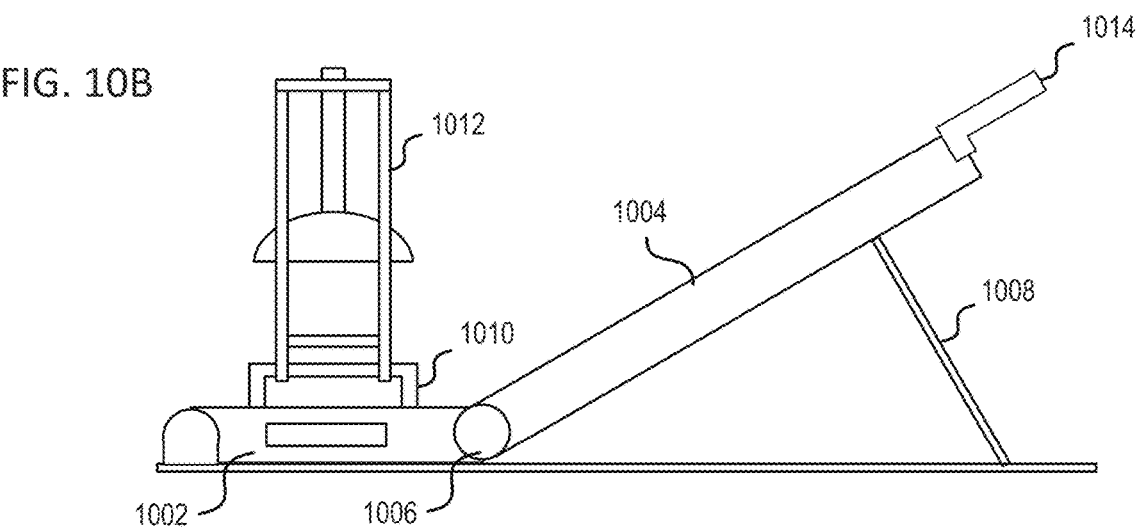
FIG. 10B depicts the elevation device of FIG. 10A in a partially elevated position according to embodiments.
Figure 10C:
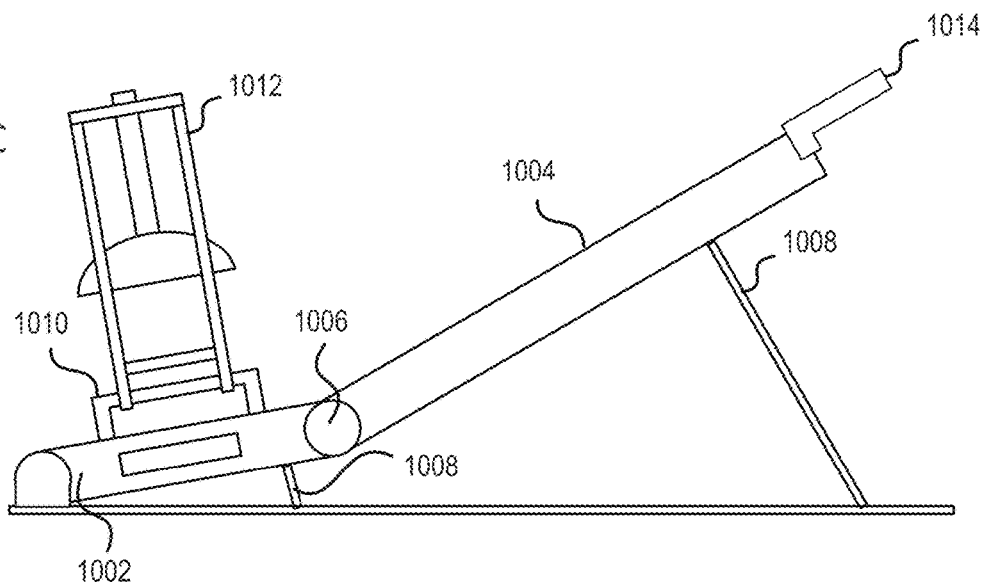
FIG. 10C depicts the elevation device of FIG. 10A in a fully elevated position according to embodiments.

In one embodiment shown in FIG. 10A, an elevation device 1000 may be configured to elevate a portion of the patient's upper body, including the upper chest/heart, shoulders, and head. Elevation device 1000 is similar to elevation devices 800 and 900 and may include similar features. Elevation device 1000 includes a first support surface 1002 that is configured to support at least a portion of the upper body. Typically, the first support surface 1002 supports at least the patient's heart, similar to the thoracic plates described elsewhere herein. The first support surface 1002 may be moved between a generally supine position and an elevated position, along with any angles therebetween. The generally supine position may involve the first support surface 1002 being between about 0 and 10 degrees relative to a horizontal plane. The elevated position may have a maximum height of between about 4 cm and 15 cm. A second support surface 1004 may be configured to support the individual's shoulders and head, with a pivot point 1006 between the first support surface 1002 and the second support surface 1004 being disposed at a position just above the patient's heart. The second support surface 1004 may be pivoted relative to the first support surface 1002 to raise the patient's shoulders and head as shown in FIG. 10B. For example, the second support surface 1004 may be raised to an angle of between about 15 and 45 degrees relative to horizontal while the first support surface 1002 is left in the generally supine position. In some embodiments, both the first support surface 1002 and the second support surface 1004 may be elevated, such as shown in FIG. 10C. The first support surface 1002 and the second support surface 1004 may be elevated to the same or different angles, typically with the second support surface 1004 being elevated at a larger angle relative to horizontal than the first support surface 1002. In some embodiments, elevation device 1000 may include a base (not shown) that is coupled with one or both of the first support surface 1002 and the second support surface 1004.

Elevation device 1000 may include one or more support posts 1008 similar to those described in relation to FIGS. 8A and 8B that are configured to maintain the first support surface 1002 and/or the second support surface 1004 at a desired elevation. In some embodiments, the support posts 1008 may be configured to rest upon a support surface, while in other embodiments, the support posts 1008 extend between the base and the respective support surface. The elevation device 1000 may also include a mounting site 1010 for a chest compression device 1012. The mounting site 1010 is typically positioned on the first support surface 1002 at a position in general alignment with the patient's heart. Elevation device 1000 may also include one or more handles 1014 on the first support surface 1002 and/or the second support surface 1004 to assist an operator in raising and/or lowering the respective support surface. Elevation device 1000 may also include one or more motors, controllers, and/or other lift mechanisms, similar to those described in relation to elevation device 500. These controllers and lift mechanisms may work in conjunction with the chest compression device 1012 to raise and/or lower the patient's upper body and/or control a rate and/or timing of chest compressions as described in relation to FIGS. 8A and 8B.

In some embodiments, the elevation devices described herein may be foldable for easy carrying. For example, the elevation devices may be configured to fold up, much like a briefcase, at or near the axis of rotation of the upper support such that the upper support may be brought in close proximity with the thoracic plate and/or base. In some embodiments, the upper support may be parallel or substantially parallel (such as within 10° of parallel) to the base. In some embodiments, an underside of the base and/or upper support may include a handle that allows the folded elevation device to be carried much like a briefcase. In other embodiments, rather than having a fixed handle, the elevation device may include one or more mounting features, such as clips or snaps that allow a handle to be attached to the elevation device for transportation while in the folded state. In some embodiments, a lock mechanism or latch may be included to lock the elevation device in the folded and/or unfolded state. In some embodiments the foldable head and thorax elevation CPR device may be folded up in a briefcase and include an automated defibrillator, physiological sensors, and the like.

Figure 11A:
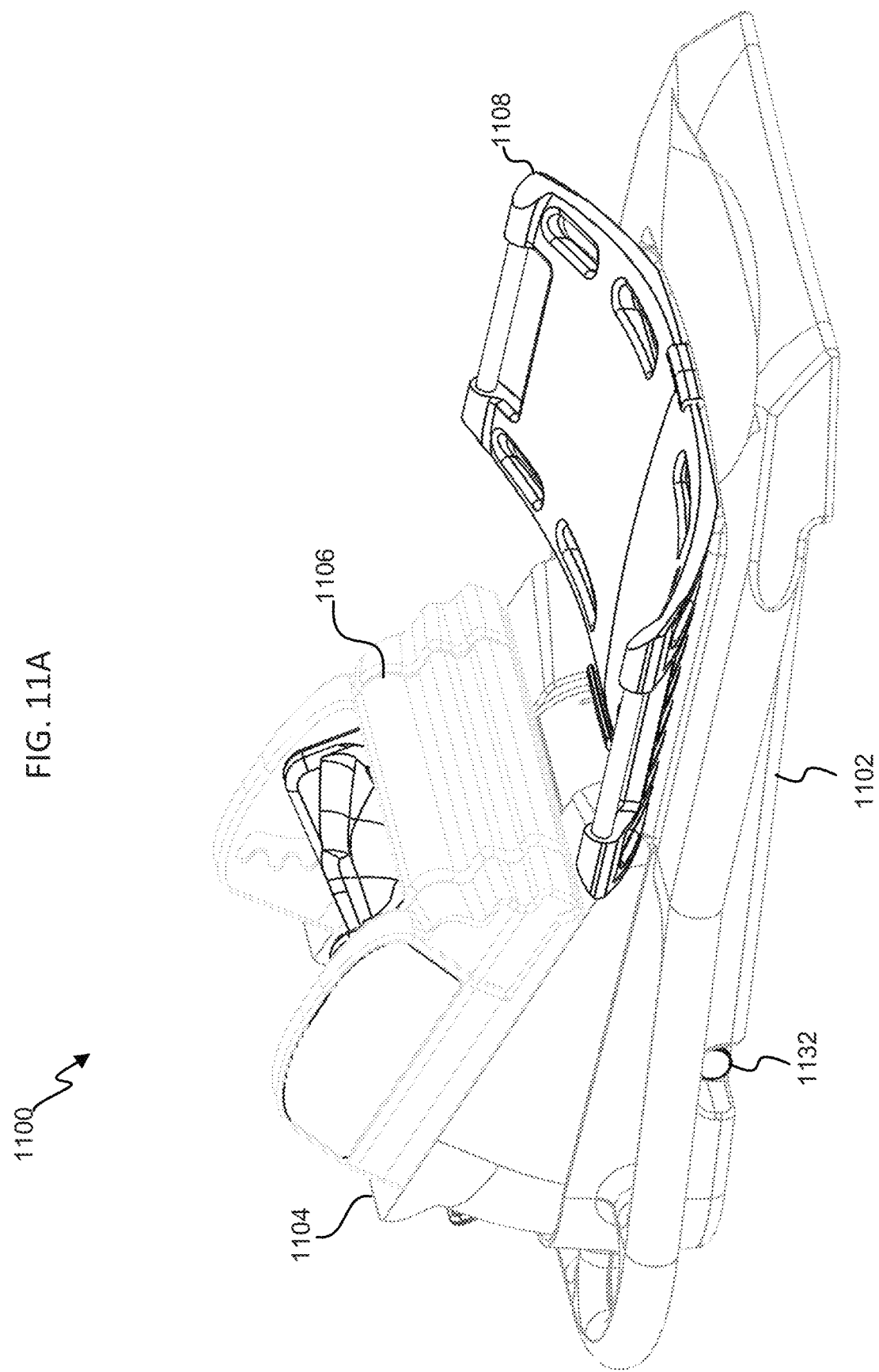
FIG. 11A depicts an elevation device in a lowered position according to embodiments.

FIGS. 11A-11L depict an example of an elevation device 1100, which may be similar to other elevation devices described herein. This device is designed to be placed under the patient, for example, as soon as a cardiac arrest is diagnosed. It has a low profile designed to slip under the patient's body rapidly and easily. For example, FIG. 11A shows that elevation device 1100 may include a base 1102 that supports and is pivotally or otherwise operably coupled with an upper support 1104. Upper support 1104 may include a neck pad or neck support 1106, as well as areas configured to receive a patient's upper back, shoulders, neck, and/or head. An elevation mechanism may be configured to adjust the height and/or angle of the upper support 1104 throughout the entire ranges of 0° and 45° relative to the horizontal plane and between about 5 cm and 45 cm above the horizontal plane. In some embodiments, the upper support 1104 may be configured to elevate the middle of the patient's head to a height that is between about 2 and 42 cm above a middle of the heart. In some embodiments, an angle between the middle of the patient's head and a middle of the heart is between about 10 and 40 degrees relative to horizontal.

A user may be positioned on the elevation device 1100 with his neck positioned on the neck support 1106. In some embodiments, the neck support 1106 may contact the individual's spine at a location near the C7 and C8 vertebrae. This position may help maintain the individual in the sniffing position, to help enable optimum ventilation of the individual. In some embodiments, the individual may be aligned on the elevation device 1100 by positioning his nipples just above a center line of the back plate 1108. The chest compression device is coupled with the back plate 1108 such that the chest compression device is in alignment with the individual's sternum at a generally orthogonal angle to ensure that the chest compressions are delivered at a proper angle and with proper force. In some embodiments, the alignment of the chest compression device may be achieved may configuring the chest compression device to pivot and/or otherwise adjust angularly to align the chest compression device at an angle substantially orthogonal to the sternum.

Figure 11B:
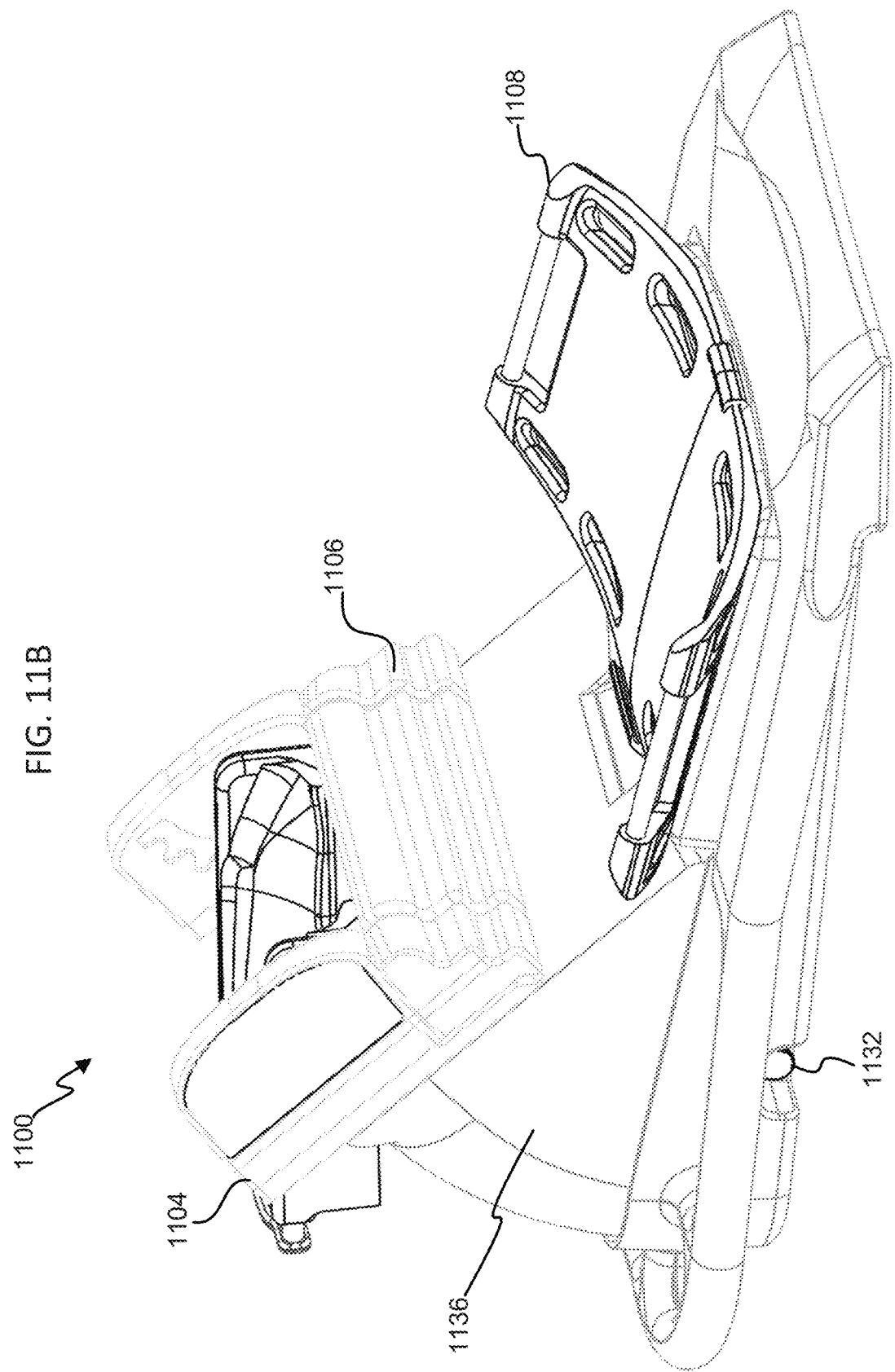
FIG. 11B depicts the elevation device of FIG. 11A in an elevated position.
Figure 11C:
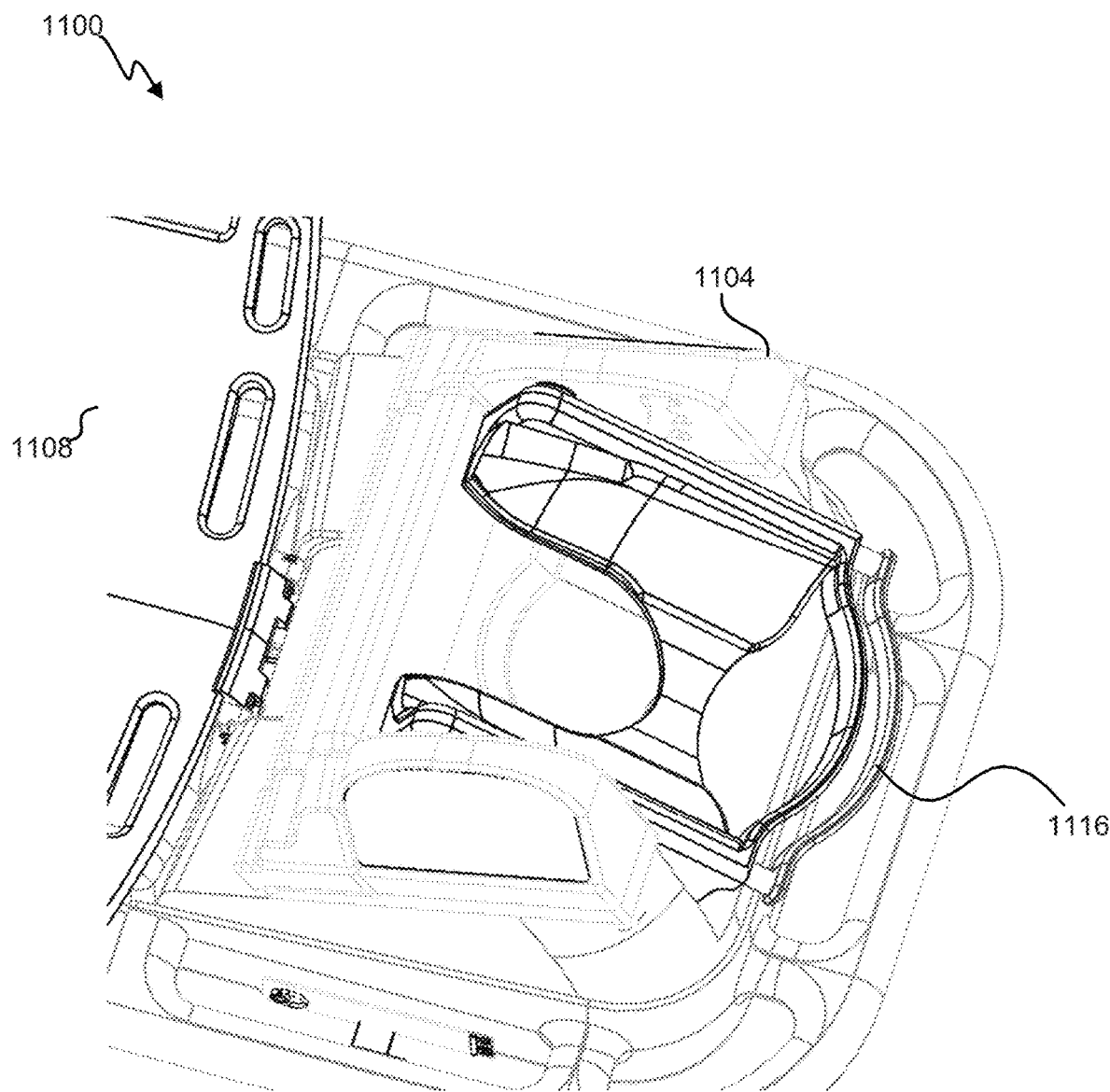
FIG. 11C depicts a locking handle of the elevation device of FIG. 11A.
Figure 11D:
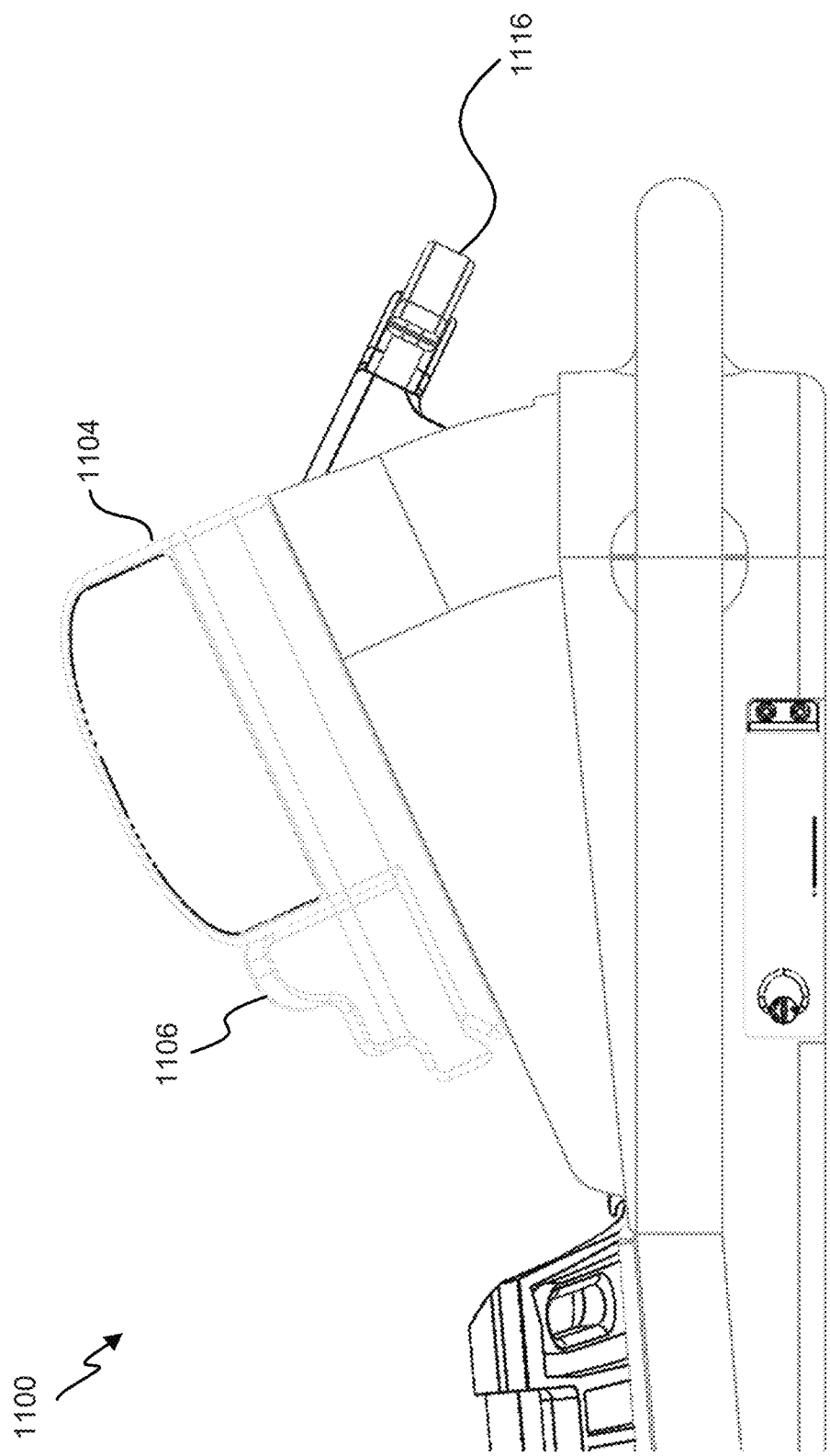
FIG. 11D depicts the locking handle of the elevation device of FIG. 11A.

As shown in FIG. 11A, elevation device 1100 is in a lowered position, with the upper support 1104 being configured to maintain the patient's head at a position that is slightly elevated relative to the heart, which is supported by back plate 1108. In the lowered position, a head-receiving portion of the upper support 1104 (which is designed to maintain the patient in the sniffing position and extends downward from a top surface of the upper support 1104) maintains the base of the head at a generally horizontal level (within about 5 degrees) when in a fully lowered position. The upper support 1104 may be raised as shown in FIG. 11B to elevate the patient's head, shoulders, and/or heart, which the head being supported at heights of between about 5 cm and 45 cm relative to a horizontal support surface on which the base 1102 is supported. Upper support 1104 may be configured to be adjustable such that the upper support 1104 may slide along a longitudinal axis of base 1102 to accommodate patients of different sizes as well as to accommodate movement of a patient associated with the elevation of the head by upper support 1104. Without such sliding ability, a patient's upper body has a tendency to curl forward on the elevation device 1100 as the patient's upper body is elevated. As shown in FIG. 11B, the upper support 1104, including neck support 1106, are extended away from the back plate 1108 when the upper support 1104 is elevated. In some embodiments, this sliding movement may be locked once an individual is positioned on the elevated upper support 1104. In some embodiments, the upper support 1104 may include one or more springs that may bias the upper support 1104 toward the torso. This allows the upper support 1104 to slide in a controlled manner when the individual's body shifts during the elevation process. In some embodiments, the one or more springs may have a total spring force of between about 10 lb. and about 50 lbs., more commonly between about 25 lb. and about 30 lb. Such force allows the upper support 1104 to maintain a proper position, yet can provide some give as the head and upper torso are elevated. Further, the elevation device may include a slide mechanism such that with elevation of the head and neck the portion of elevation device behind the head and shoulder elongates. For example, the slide mechanism may include roller bearings that are mounted on a track that allows the upper support 1104 to slide to accommodate patients of different sizes as well as to handle shifting of the body during elevation, which helps to maintain the neck in the sniffing position. In some embodiments, such as those shown in FIGS. 11C and 11D, a locking handle 1116 is provided that allows medical personnel to adjust a lateral position of the upper support 1104 relative to the base 1102. To actuate the handle 1124, a user must apply force to push a distal portion 1126 of the handle 1124 toward a fixed, proximal portion 1128 of the handle 1116. This action pushes a locking member (not shown) into a free space of a ratchet mechanism, allowing the user to adjust the lateral position of the upper support 1104. Once released, the locking member may enter a tooth of the ratchet to set a position of the upper support 1104 based on a size of the user. The upper support 1104 may then only slide in small amounts to handle the shifting of the patient throughout the elevation process.

Figure 11E:
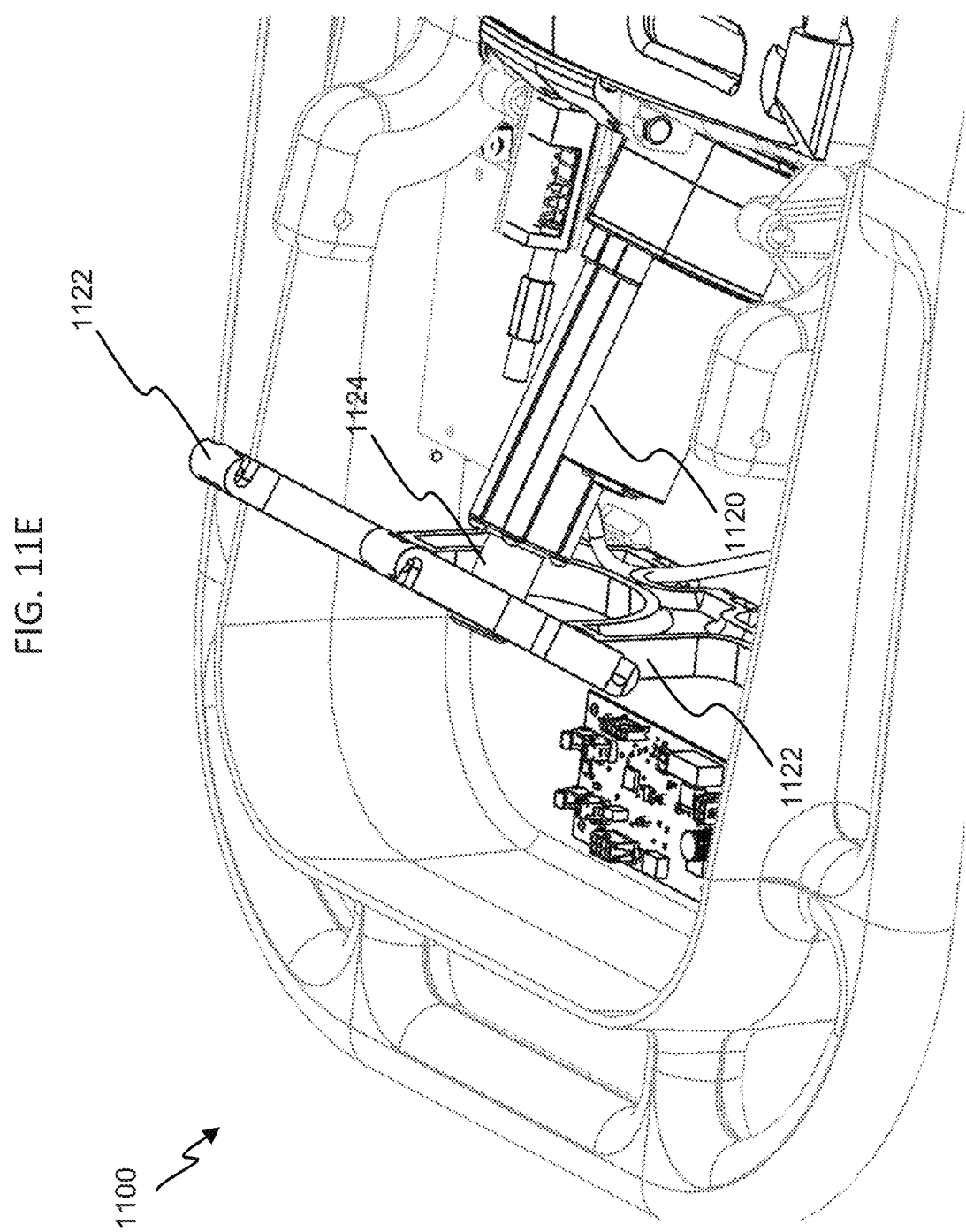
FIG. 11E depict a linear actuator of the elevation device of FIG. 11A in an elevated position.
Figure 11F:
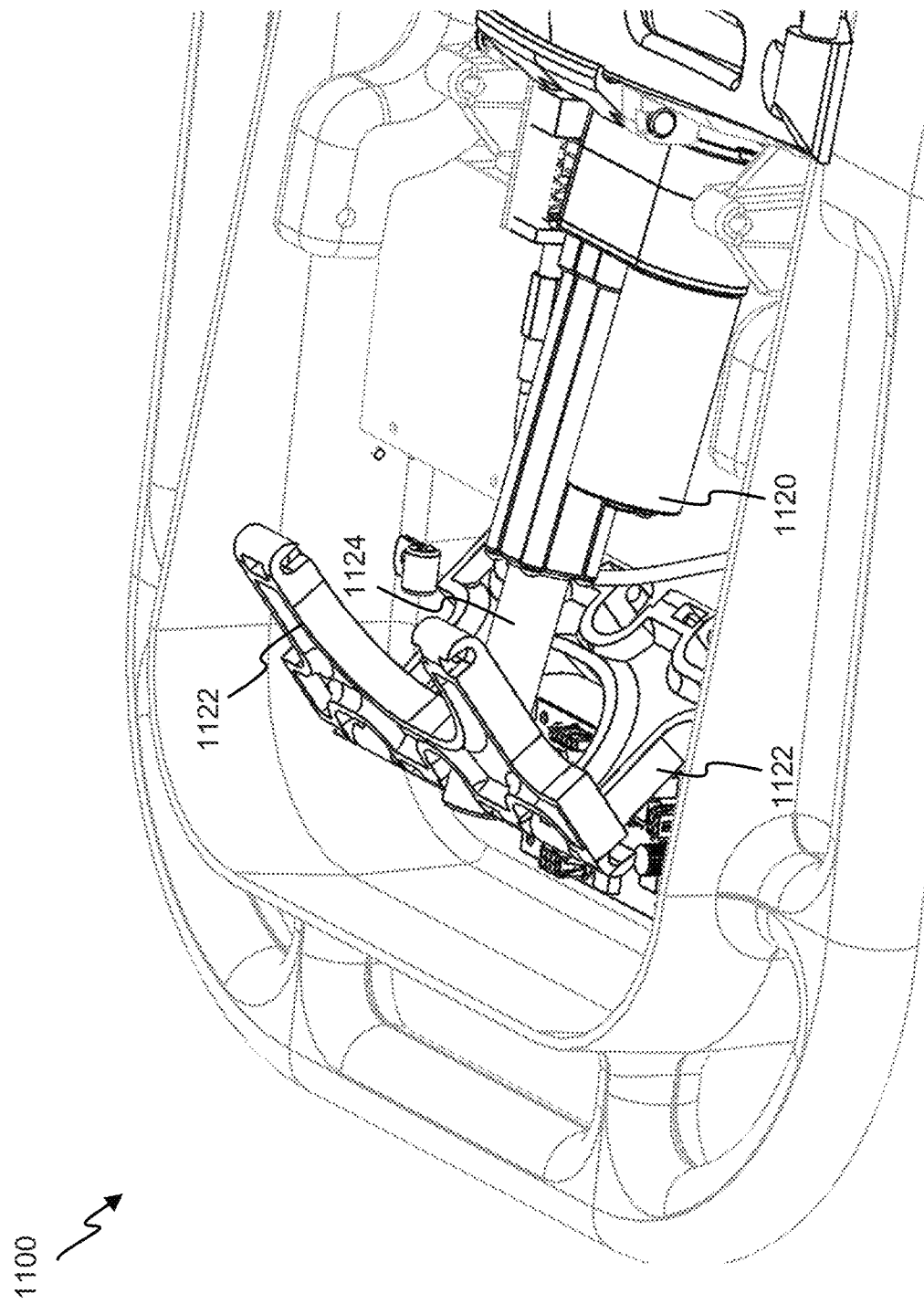
FIG. 11F depict the linear actuator of the elevation device of FIG. 11A in a lowered position.

FIGS. 11E and 11F depict a linear actuator 1120 that is used to raise and lower the upper support 1104. Linear actuator 1120 is coupled at a joint formed between two or more support members 1122. Support members 1122 are coupled between the base 1102 and a bottom surface of the upper support 1104 such that top support member(s) 1122 is coupled with the upper support 1104 and the bottom support member(s) 1122 is coupled with the base 1102. As linear actuator 1120 is operated, a rod 1124 of the linear actuator 1120 shortens to draw the joint of the support members 1122 toward the back plate 1108, which causes an angled between the top and bottom supper members 1122 to increase, such as shown in FIG. 11E, forcing the upper support 1104 upward to elevate a patient's upper body. When operated in reverse, the rod 1124 of linear actuator 1120 extends, pushing on the joint to decrease the angle between the top and bottom support members 1122 as shown in FIG. 11F, thereby lowering the upper support 1104. It will be appreciated that the direction of operation of the linear actuator 1120 and support members 1122 may be reversed in some embodiments such that lengthening rod 1124 causes elevation of the upper support 1104 and shortening of rod 1124 causes the lowering of the upper support 1104. While shown here with a linear actuator 1120 and support member 1122 elevation mechanism, it will be appreciated that elevation device 1100 may additionally or alternatively include other elevation mechanisms, such as threaded rods, lead screws, pneumatic and/or hydraulic actuators, motor driven telescopic rods, other elevation mechanisms, and/or combinations thereof.

Turning back to FIGS. 11A and 11B, the back plate 1108 may be sized and shaped to receive a portion of the patient's back, just behind the heart and may be configured to couple with a chest compression device (not shown). Examples of CPR assist devices that could be used with the elevation device (either in the current state or a modified state) include the Lucas device, sold by Physio-Control, Inc. and described in U.S. Pat. No. 7,569,021, the entire contents of which is hereby incorporated by reference, the Defibtech Lifeline ARM—Hands-Free CPR Device, sold by Defibtech, the Thumper mechanical CPR device, sold by Michigan Instruments, automated CPR devices by Zoll, such as the AutoPulse, as also described in U.S. Pat. No. 7,056,296, the entire contents of which is hereby incorporated by reference, the Weil Mini Chest Compressor Device, such as described in U.S. Pat. No. 7,060,041 (Weil Institute), and the like. Chest compression devices used in accordance with the present invention may be configured to compress and/or actively decompress the chest.

In some embodiments, the back plate 1108 may have a curved profile that may provide some flexibility to the back plate 1108. This flexibility helps when the elevation device 1100 is used in conjunction with a chest compression device, as the flexibility ensures that the right amount force applied to the patient's chest. For example, a central portion of the back plate 1108 may flex in the presence of excessive force, thereby absorbing some of the force. For example, as a plunger of a chest compression device is pressed into the patient's chest, some force is transmitted through the patient to the back plate 1108. The back plate 1108 may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing back plate 1108, rather than the ribs or other body structures, absorbs a significant portion of the excess force. Such a design is particularly useful when the elevation device is used in conjunction with a chest compression device such as the Lucas device, sold by Physio-Control, Inc. and/or the Zoll AutoPulse.

Figure 11H:
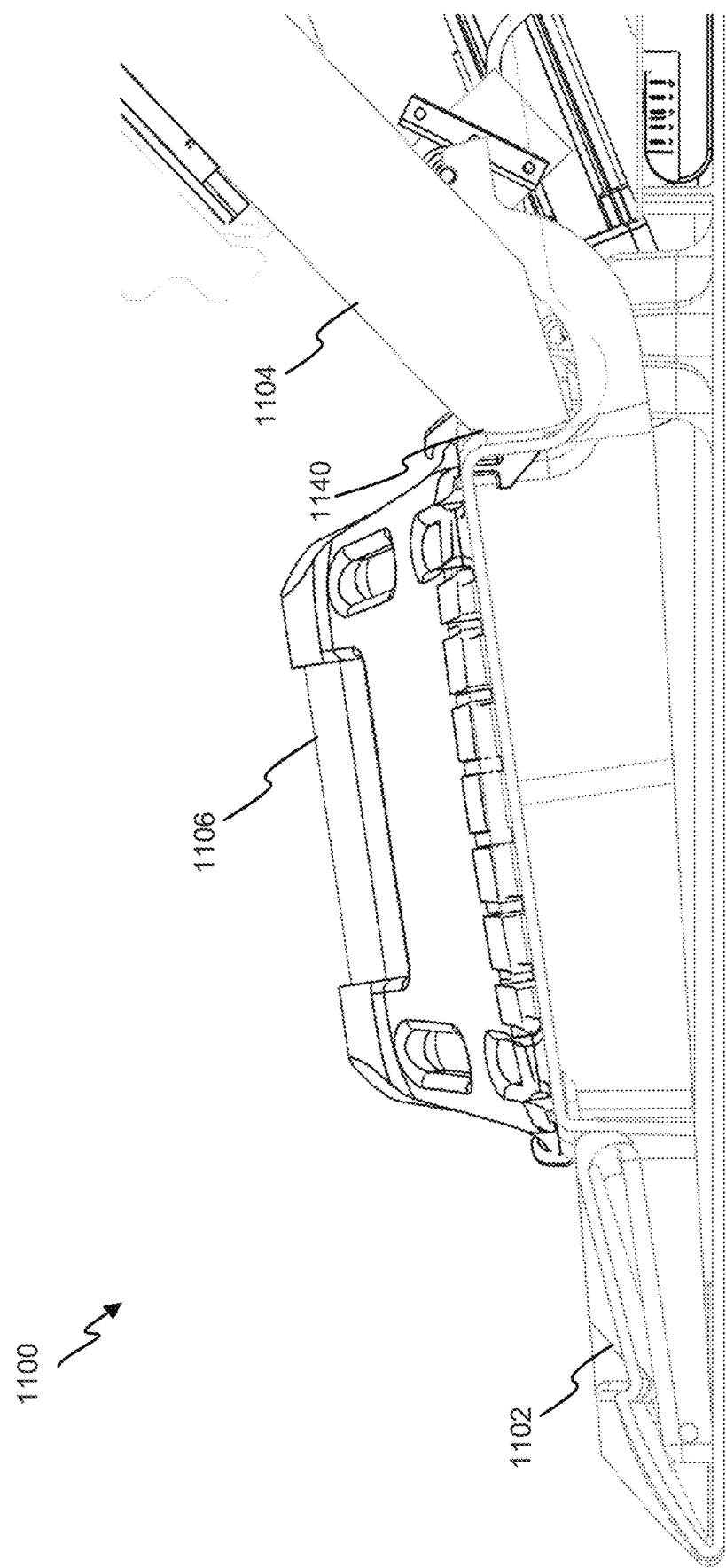
FIG. 11H depicts the elevation device of FIG. 11A in an elevated position.

In some embodiments, the back plate 1108 that is part of and/or is coupled with the upper support 1104 in such a manner that an angle of the back plate 1108 is adjustable relative to the base 1102 and/or the upper support 1104. The back plate 1108 may be configured to adjust angularly to help combat thoracic shift to help maintain a chest compression device at a generally orthogonal to the sternum. The adjustment of the back plate 1108 may create a separate elevation plane for the heart, with the head being elevated at a greater angle using the upper support 1104 as shown in FIG. 11B. In some embodiments, the back plate 1108 may be adjusted independently, while in other embodiments, adjustment of the back plate 1108 is tied to the elevation of the upper support 1104. For example, a back plate may include a roller (such as a v-groove bearing) positioned on an elevation track formed on or coupled with an underside of an upper support as illustrated in the embodiment discussed in relation to FIGS. 4G-4J of U.S. patent application Ser. No. 15/850,827, previously incorporated by reference. The roller may be positioned on a forward, raised portion of the elevation track. As the upper support 1104 is elevated, the roller is forced upward by elevation track, thereby forcing an end of the back plate 1108 proximate to the upper support 1104 upwards. This causes the back plate 1108 to tilt, thus maintaining the chest at a generally orthogonal angle relative to the chest compression device that is coupled with the back plate 1108. Oftentimes, elevation track may be slanted from a raised portion proximate to the back plate 1108 to a lowered portion. The elevation track may be tilted between about 4° and 20° to provide a measured amount of tilt relative to the thoracic shift expected based on a particular elevation level of the upper support 1104. Typically, the back plate 1108 will be tilted at a lower angle than the upper support 1104 is inclined. Such simultaneous movement is also demonstrated in FIGS. 11G and 11H. In FIG. 11G, the upper support 1104 is in the lowered position and the back plate 1108 is in its original position. In FIG. 11H, the upper support 1104 is elevated, which has caused the back plate 1108 to have a corresponding forward tilt, which is less that than the degree of elevation of the upper support 1104.

Figure 11I:
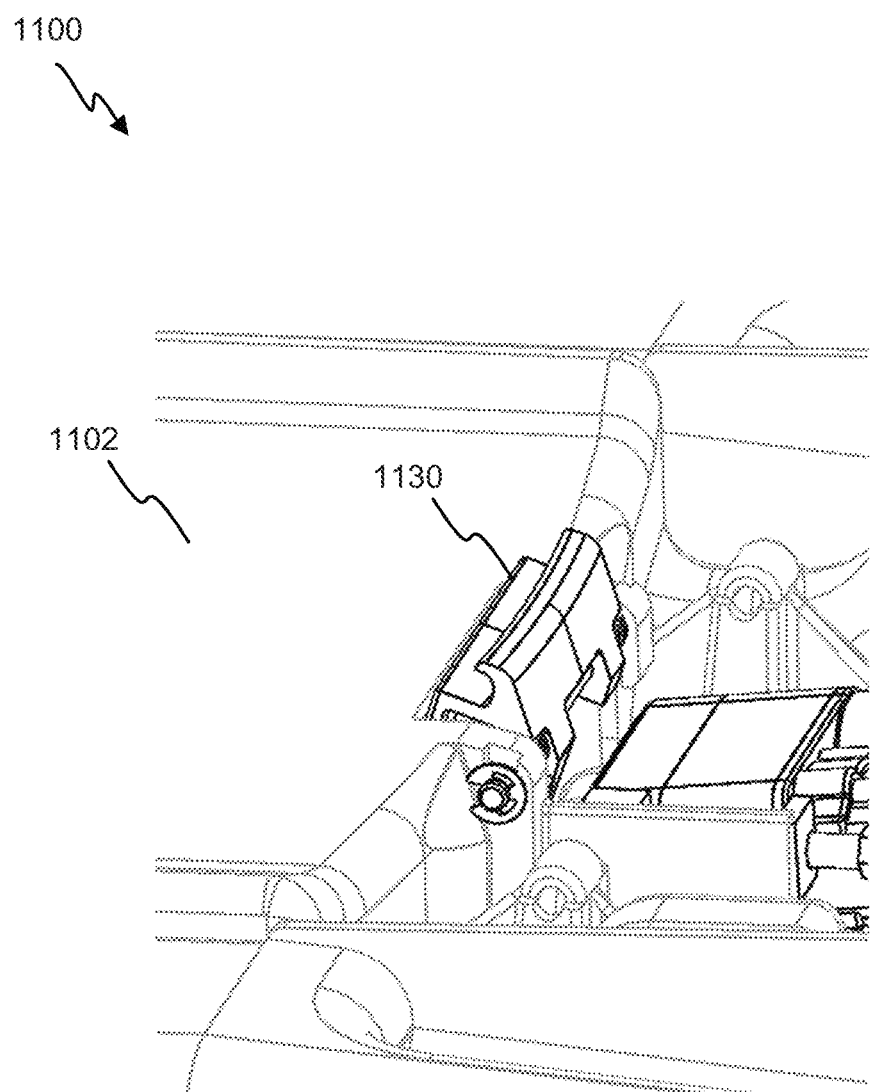
FIG. 11I depicts a latch of the elevation device of FIG. 11A.
Figure 11J:
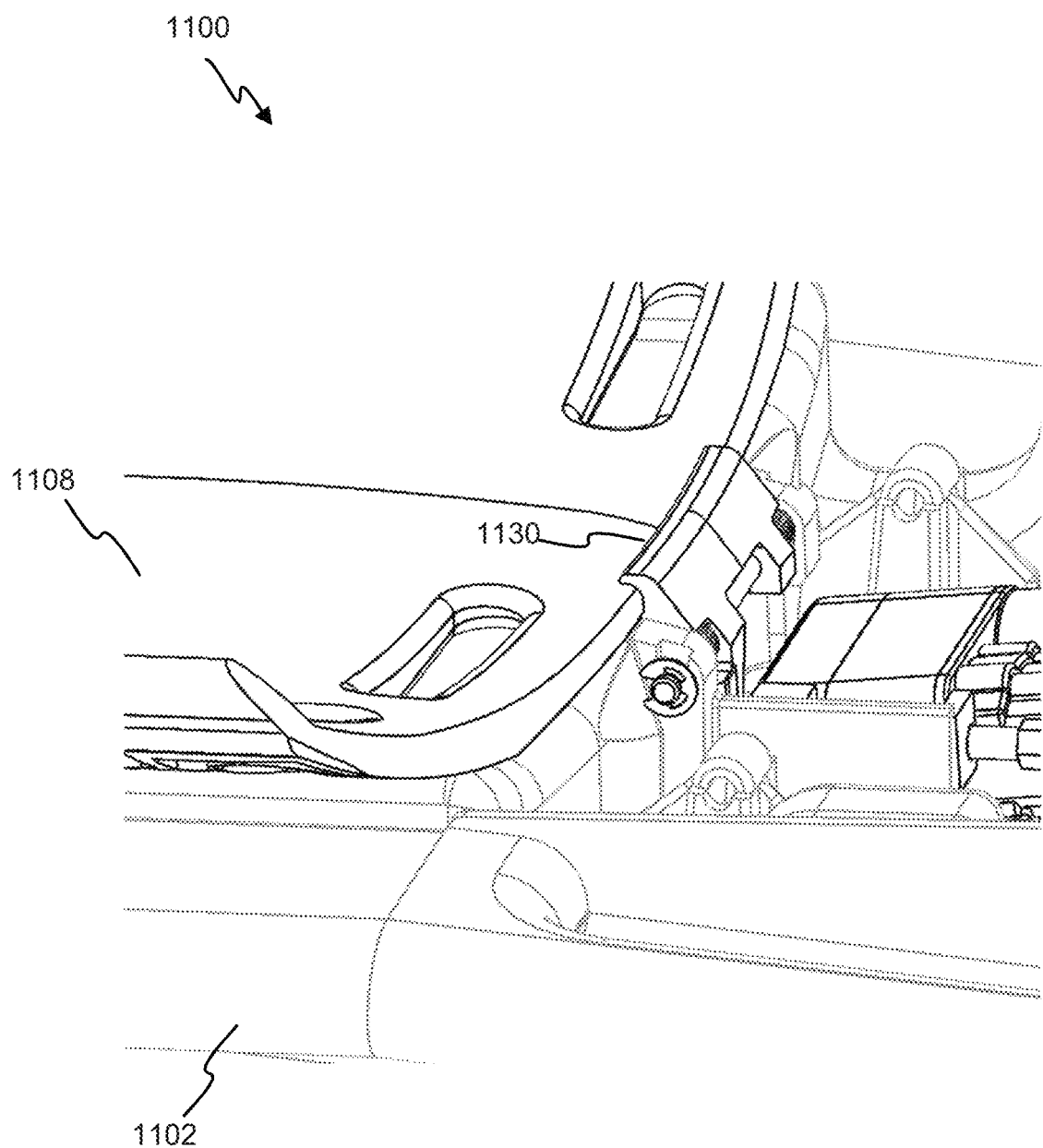
FIG. 11J depicts the latch of the elevation device of FIG. 11A.
Figure 11L:
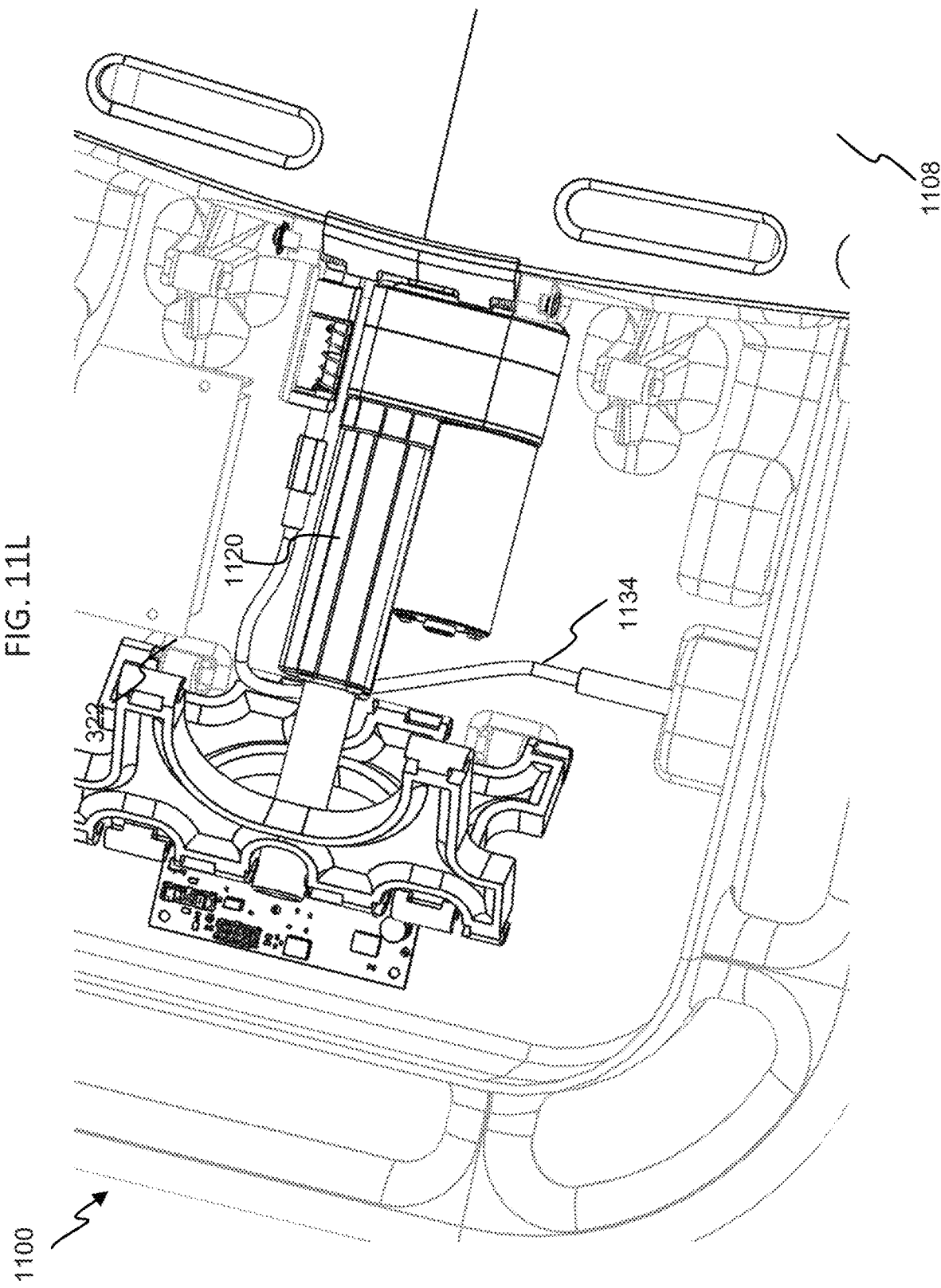
FIG. 11L depicts a release cable of the elevation device of FIG. 11A.

In some embodiments, the back plate may be removably coupled with the base 1102 and/or the upper support 1104. As shown in FIG. 11I, a latch 1130 is provided beneath the back plate 1108. The latch 1130 may be spring biased such that a bottom surface of the latch 1130 is able to receive a back edge of the back plate 1108. The latch 1130 may be pushed downward with the back plate 1108 secured by a tip of the latch 1130 until a spring-biased pin (not shown) slides along a bottom surface of the latch 1130 and engages with a hole formed within a body of the latch 1130. The pin secures the latch 1130 in a locked position in which the back plate 1108 is securely coupled with the base 1102 and/or upper support as shown in FIG. 11J. A release knob 1132 shown in FIG. 11K is coupled with the base 1102 and may be used to draw the pin out of the hole formed in the body of latch 1130 to release the back plate 1108. For example, as shown in FIG. 11L, release knob 1132 may be coupled to the pin via a flexible cable 1134, similar to a brake cable on a bicycle. When knob 1132 is pulled, the pin is drawn out of the hole and the spring force can push the latch 1130 into a release position in which the back plate 1108 may be removed from the base 1102.

In some embodiments, the elevation device 1100 may include a number of features that make the device more safe to operate. For example, as seen in FIG. 11A, elevation device 1100 may include a vinyl (or other natural or synthetic material) cover 1136 that may cover the moving components, such as the motor or actuator and/or slide mechanism. the cover 1136 can extend and retract as the upper support 1104 raises and lowers. For example, cover 1136 may operate in a manner similar to a convertible top for an automobile, and may retract in a compact, accordion style manner when the upper support 1104 is lowered. The upper support 1104 of elevation device 1104 may have a front surface 1140 that is curved in a manner such that as the upper support 1104 raises and lowers the front surface 1140 stays approximately the same distance from the back plate 1108. In other words, a gap between the two components remains generally constant, which eliminates any possible pinching hazard that could exist due to the relative movement between the two components.

In one embodiment, a controller and/or control system may adjust an actuation speed of a motor or other elevation mechanism to raise or lower the upper support 1104 of the elevation device 1100 within the necessary time frame. For example, medical personnel may set a desired elevation time, starting elevation angle, intermediate elevation angle(s), final elevation angle, rate of elevation, etc. The controller will then operate linear actuator 1120, a motor, and/or other elevation mechanism to slowly raise the upper support 1104 from a starting elevation angle to a final elevation angle over the selected time period. For example, the controller may be configured to elevate the head and thorax may be done in a sequence by 1) elevating the head and thorax over two or more sequential elevation steps and/or 2) elevating the head and thorax over a more prolonged period of time from the start of the elevation to the final height. In some embodiments, the controller may cause the chest compression device to perform CPR for a period of time (between about 30 seconds and 10 minutes, more commonly between about 2 minutes and 8 minutes, and more commonly between about 3 minutes and 6 minutes) while the individual is in a flat, supine position (or nearly supine, such as with the head and/or heart elevated slightly to an angle of less than about 5 degrees relative to horizontal) prior to causing the actuator to elevate the upper support 1104 and the individual to an intermediate and/or final height. In some embodiments where the individual has been primed flat, the controller may perform an additional priming step at an intermediate elevation position prior to elevating the individual to the final/highest elevation position. In other embodiments, the individual may be primed by first elevating the individual's head and heart to one or more intermediate elevation positions (i.e. between about 10 and 25 degrees) and then performing chest compressions for a period of time prior to elevating the individual's heart and head to a final elevation position (i.e. between 20 and 45 degrees). Thus, in some embodiments the starting elevation position may range between about 0 and 25 degrees, and more commonly between about 0 and 15-20 degrees. Such starting elevation positions may result in the individual's heart being at a position of between about 0 cm to 8 cm above horizontal and the individual's head being at a position of between about 0 and 15 cm above horizontal. The chest compressions may be continued during the elevation adjustment periods after each priming step.

The controller may also control the rate of elevation of the upper support 1104. As just one example, the controller may maintain the elevation speed at a rate of not faster than 1° over each 0.3 second period. The lift speed may be linear and/or non-linear throughout each elevation step.

Blood drains rapidly from the head when the patient has no blood pressure and the head and upper body are elevated. As a result, there is a need to lower the head fairly rapidly to prevent blood loss in the brain if CPR is stopped while the head is elevated. Typically, this means that the patient's head and upper body may be elevated at a different rate than it is lowered. The patient's head may be lowered by the controller between about 1 and 10 seconds, and typically between about 1-5 seconds.

The controller may also be configured to cause the actuator to slowly and continuously raise the upper support 1104 (and individual's heart, shoulders, and head) from a starting elevation position to a final elevation position. For example, a starting elevation position may include the individual being positioned in a generally flat, supine position (with the head elevated less than 5° relative to horizontal). The individual's head, shoulders, and heart may be slowly raised (linearly and/or non-linearly) from the starting elevation position to a position where the head is elevated between about 20 and 45 degrees relative to horizontal (an absolute elevation of the heart by about 5-10 cm and an absolute elevation of the head by about 15-25 cm, although these ranges may vary based on the age, size, and/or physiology of a specific individual) over a period of between about 30 seconds and 10 minutes, more commonly between 2 minutes and 8 minutes, and optimally between about 3 minutes and 6 minutes, while CPR is performed. For example, the head, shoulders, and heart may be raised at a rate of between about 2.25°/second and about 1.5°/minute. In other embodiments, an individual may be quickly raised to a starting elevation position of between about 8-15 degrees before slowly elevating the head, shoulders, and heart to a final elevation positon over a period of between about 30 seconds and 10 minutes, more commonly between 2 minutes and 8 minutes, and optimally between about 3 minutes and 6 minutes, while CPR is performed.

In some embodiments, the controller may receive data from one or more physiological sensors and use this data to determine rates and timing of elevation and lowering. For example, the patient on the elevation device 1100 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the upper support 1104. For example, once it is detected that the patient has a stable heart rhythm, the controller may alert medical personnel that chest compressions should be ceased, and may send a signal to the motor or other actuator to cause the upper support 1104 to rapidly lower. In some embodiments, alerting medical personnel may involve producing a visual indicator, such as lighting up a light emitting diode (LED) or other light source and/or presenting a textual and/or image-based display on a screen of the elevation device 1100. In one embodiment, upon detecting a stable heart rhythm, the controller may send a command to the automatic chest compression device that causes the chest compression device to stop the delivery of chest compressions and/or decompressions. In another embodiment, upon detecting the stable heart rhythm, the controller will alert medical personnel, who may then operate the elevation device 1100 to lower the upper support 1104. It will be appreciated that other sensors may be used in conjunction with the elevation device 1100 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

The elevation device 1100 elevates the head above the heart, with the level of elevation optionally varying depending upon the method of CPR. CPR itself is inherently inefficient, providing only about 20% of normal blood flow to the heart and brain. Elevation of the head is not safe during conventional CPR as it is not possible to consistently or safely push enough blood "uphill" to the head to take advantage of the effects of gravity of the venous side of the arterial-venous circuit that is integral to cerebral perfusion. Methods of CPR that generate the most forward flow provide the opportunity to elevate the head above the heart more than those methods that provide less forward flow. For example, active compression decompression (ACD) CPR with an impedance threshold device (ITD) can triple blood flow to the heart and brain compared with conventional manual CPR alone and therefore the head can be elevated higher and still get enough perfusion to take advantage of the effects of gravity with HUP CPR. By contrast, the head should not be elevated as much with conventional CPR and the ITD as forward blood flow without ACD CPR is less, and therefore too much elevation of the head could worsen outcomes. For these reasons the optimal head elevation may vary both depending upon the method of CPR used and the condition of the patient.

The relative vertical distance between the head and the heart is important as the amount of pressure needed to "lift" or pump the blood from the heart to the brain is related to this distance. Further, the vertical distance between the head and the heart affects the amount of cerebral perfusion. Although the amount of elevation of the head relative to the heart may vary depending upon the method of CPR (which is the mechanism used to pump the blood), it is generally preferred to have the head elevated relative to the heart by a distance in the range from about 2 cm to about 42 cm. In the specific case where ACD-CPR is being performed with an ITD, the distance may be in the range from about 5 cm to about 25 cm, for standard CPR with an ITD between about 5 cm and about 20 cm, for ACD CPR by itself between about 5 cm and about 20 cm, and with conventional or standard CPR between about 3 cm and about 15 cm. Further, the distance that the heart may be elevated relative to a support surface upon which the lower portion of the patient is resting (such as a table, floor, gurney, stretcher, or the ground) may be in the range from about 2 cm to about 20 cm (with ranges between about 4 cm and 10 cm being common), while the height of the head relative to the support surface may be in the range from about 5 cm to about 45 cm (with ranges between about 10 cm and 40 cm being common). When performing ACD-CPR+ITD, the distance that the heart may be elevated relative to a support surface upon which the patient is resting may be in the range from about 2 cm to about 20 cm, while the height of the head relative to the support surface may be in the range from about 5 cm to about 45 cm. Of course, these relative heights can also be thought of in terms of an angle of elevation of the upper body relative to the lower body when the patient is bent at the waist when performing CPR. Such angles are described herein. Typically, the angle between the patient's heart and brain is between 10 degrees and 40 degrees relative to horizontal to achieve the necessary elevation, although it will be appreciated that such angles are largely driven by the patient's physiology (height, distance between head and heart, etc.).

In some embodiments the heart will not be elevated. For example, a small head-only elevation device may be used that would only elevate the head, while allowing the heart to remain in the horizontal plane along with the lower body. Such elevation devices may be particular useful when performing CPR without the use of a CPR assist device/ automated chest compression device as it reduces the amount of force needed to pump blood to the patient's brain during CPR. In such cases, the head would be raised to a distance in the range from about 5 to 20 cm relative to the heart (which is not elevated relative to the support surface).

In some embodiments, the controller be configured to detect a type of CPR being delivered and may automatically adjust an elevation of the heart and/or head based on the detected level of force. This may be done, for example, by allowing a user to input a type of CPR being performed into the elevation device 1100. In other embodiments, such as those where a chest compression device is coupled with or formed integrally with the elevation device, the elevation device may communicate with the chest compression device to determine if the chest compression device is being used to deliver compressions and/or an amount of force being delivered and may make any necessary elevation adjustments based on this data. In other embodiments, one or more physiological sensors may be used to detect physiological parameters, such as cerebral perfusion pressure, intrathoracic pressure, and the like. This sensor data may be used to determine a compression force and/or otherwise determine how high to elevate the head and heart.

It should be noted that the elevation devices/head up devices (HUD) could serve as a platform for additional CPR devices and aids. For example, an automatic external defibrillator could be attached to the HUD or embodied within it and share the same power source. Electrodes could be provided and attached rapidly to the patient once the patient is place on the HUD. Similarly, ECG monitoring, end tidal $CO_2$ monitoring, brain sensors, a defibrillator, and the like could be co-located on the HUD. In addition, devices that facilitate the cooling of a patient could be co-located on the HUD to facilitate rapid cooling during and after CPR.

In addition or alternatively to one or more of the techniques described above, in some embodiments, the chest compression device will be coupled to a device to elevate the head and thorax that includes one or more support restraints (such as straps, belts, rods, cloth strips, and the like) to stabilize the patient on the elevation device.

It should be further noted that during the performance of CPR the compression rate and depth and force applied to the chest might vary depending upon whether the patient is in the flat horizontal plane or whether the head and thorax are elevated. For example, CPR may be performed with compressions at a rate of 80/min using active compression decompression CPR when flat but at 100 per minute with head and thorax elevation in order to maintain an adequate perfusion pressure to the brain when the head is elevated. Moreover, with head elevation there is better pulmonary circulation so the increase in circulation generated by the higher compression rates will have a beneficial effect on circulation and not "overload" the pulmonary circulation which could happen when the patient is in the flat horizontal plane.

It will be appreciated that some embodiments may utilize simplified elevation devices. For example, an elevation device may include only a base an upper support, and an actuator for raising and lowering the upper support relative to the base. The upper support may have one or more generally planar surfaces, with one or more of the surfaces optionally being contoured to match a shape of a patient's back. Additionally, the curved profile may make the support surface flexible. This flexibility helps when the elevation device 1100 is used in conjunction with a chest compression device, as the flexibility ensures that the right amount force applied to the patient's chest. For example, a central portion of the upper support may flex in the presence of excessive force, thereby acting as a flexible back plate to absorb some of the force. For example, as a plunger of a chest compression device is pressed into the patient's chest, some force is transmitted through the patient to the upper support. The upper support may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing back plate, rather than the ribs or other body structures, absorbs a significant portion of the excess force. Such a design is particularly useful when the elevation device is used in conjunction with a chest compression device such as the LUCAS device, sold by Physio-Control, Inc. and/or the Zoll AutoPulse and/or devices that combine the concepts underlying the load-distributing band in the AutoPulse and automated active compression decompression (ACD) as in the LUCAS. However, it will be appreciated that the flexible upper support may be used in conjunction with any of the embodiments of elevation devices described herein. It should be appreciated that the portion of the elevation device under the heart and thorax could also contain force, pressure, impedance, and/or position sensors to provide feedback to the chest compression device, assuring the proper compression depth and force are delivered, even though the amounts needed to provide the proper CPR may differ from patient to patient and may change over time. In some embodiments, the chest compression device may be coupled with the elevation device 1100 in such a manner that compressive and/or decompressive force from the chest compression device remains generally perpendicular (within 5 degrees) to the patient's sternum at all elevation positions.

In some embodiments, the patient's upper body may be elevated at a same angle on a single surface of the upper support, while in other embodiments the upper support may have two or more generally planar surfaces that elevate the heart and head at different angles relative to horizontal. The actuator may be manual and/or automatically driven with operating controls that enable the upper support to be to be raised and lowered in a controlled manner necessary to perform sequential elevation as described herein. For example, the elevation device may be fitted with controllers, motors, threaded rods, lead screws, pneumatic and/or hydraulic actuators, motor driven telescopic rods, other elevation mechanisms, and/or combinations thereof. In some embodiments, the motors may be coupled with a controller or other computing device. The controller may communicate with one or more input devices such as a keypad. This allows a user to select an angle and/or height of the heart and/or head to be raised using the motor and/or other actuator, along with a rate of elevation or other timing element of the elevation process. Additionally, the controller may be coupled with one or more sensors, such as flow and pressure sensors. Sensor inputs may be used to automatically control the motor and angle of the supports based on flow and pressure measurements. A type of CPR and/or ITP regulation may also be controlled using these and/or other sensor inputs. In some embodiments, the electro-mechanical lift mechanisms may include disengagement mechanisms that allow the elevation device to be operated manually. This allows the elevation device to be operable even if a power source for the electromechanical features is unavailable, such as when a battery is dead or when there is no power outlet or other power source available.

In some embodiments, the upper support may define an opening that is configured to receive a portion of a patient's head. This opening may help maintain the patient in the sniffing position for optimal airway management. Oftentimes, a head support may be included on the upper support. It will be appreciated that in some embodiments the head support may extend around the entire opening. The head support may be formed of contoured padding, such as foam padding, such that patients having heads of different sizes and shapes may be supported adequately by the single head support.

In some embodiments, the chest compression device and the elevation device may share a common power source. For example, the chest compression device or the elevation device may include a power source, such as a power cord and/or battery. The non-powered device may then plug into the other device to share the power source. In other embodiments, the chest compression device and the elevation device may be formed as a single device, with the elevation mechanism of the elevation device and the chest compression device both being wired to a single power source.

In some embodiments, the chest compression device and elevation device may be configured to communicate with each other. For example, one or more network or other data cables and/or wireless interfaces may couple processors and/or sensors of each device to one another. Data regarding elevation height, speed of elevation, speed of declination, CPR rate, force applied to the patient, and/or other data may be measured and shared between the devices. Additionally, data from physiological sensors may be shared with the elevation device and/or the chest compression device. This physiological data, such as ICP, blood flow data, blood pressure, intrathoracic pressure measurements, and the like may be used to control the various parameters such as elevation timing, elevation angle, chest compression depth and/or force, and the like.

Additionally, the chest compression device and/or elevation device may be configured to communicate with other devices, such as computers, mobile devices like mobile phones and tablet computers, e-readers, other medical equipment, such as electrocardiographs and defibrillators, and the like. To enable such communication, one or more wired and/or wireless communication networks may be established. For example, various data cables may be used to communicatively couple the chest compression device and/or elevation device to one or more remote devices. In some embodiments, the chest compression device and/or elevation device may include a wireless communications interface that is configured to communicate with one or more remote devices using WiFi, Bluetooth, 3G, 4G, LTE, and/or other wireless communications protocols.

In some embodiments, the elevation device may be coupled with a stretcher-like device for transport that has features that allow the heart and head to be elevated above the plane of the abdomen and lower extremities. For example, the stretcher or stretcher-like device may include rails or other rigid or semi-rigid support members that may be used to secure the elevation device and/or the chest compression device to the stretcher. The elevation device and/or the chest compression device may be coupled to the support members using clamps cables, and/or other securement mechanisms that may ensure the elevation device and/or the chest compression device do not shift relative to the stretcher.

In some embodiments, the elevation device may include a stowable shelf (not shown). The stowable shelf may be configured to be maintained in a stowed position in which most or all of the shelf is disposed within an interior of the elevation device, with only a handle and/or outer surface of the stowable shelf remaining exposed exteriorly of the elevation device. The stowable shelf may be extended outward into an extended position in which all or a large portion of the stowable shelf protrudes from a side of the wedge 1100. This protruding portion may be used by medical personnel as a support for their knees so that the rescuer may be elevated relative to the ground and positioned properly for administering CPR. For example, the stowable shelf may be configured to elevate the rescuer to a height of between about 2 and 4 inches relative to the ground. Oftentimes, the stowable shelf may be positioned on a roller track or other sliding mechanism that enables the stowable shelf to be manipulated between the stowed position and the extended position.

Oftentimes it may be beneficial to gather data related to actual cases where CPR was performed. To gather this data, the elevation devices and/or intrathoracic pressure regulation devices may include sensors that are configured to measure and record various data related to the performance of CPR. Additional sensors and devices may also be used in conjunction with the elevation devices and/or intrathoracic pressure regulation devices to gather relevant data. Oftentimes this data may serve as feedback that drives various aspects of the CPR process. This data may also be useful in further advancing the science behind HUP CPR techniques, as well as to provide training data to help medical personnel learn and perfect the necessary techniques.

Figure 12:
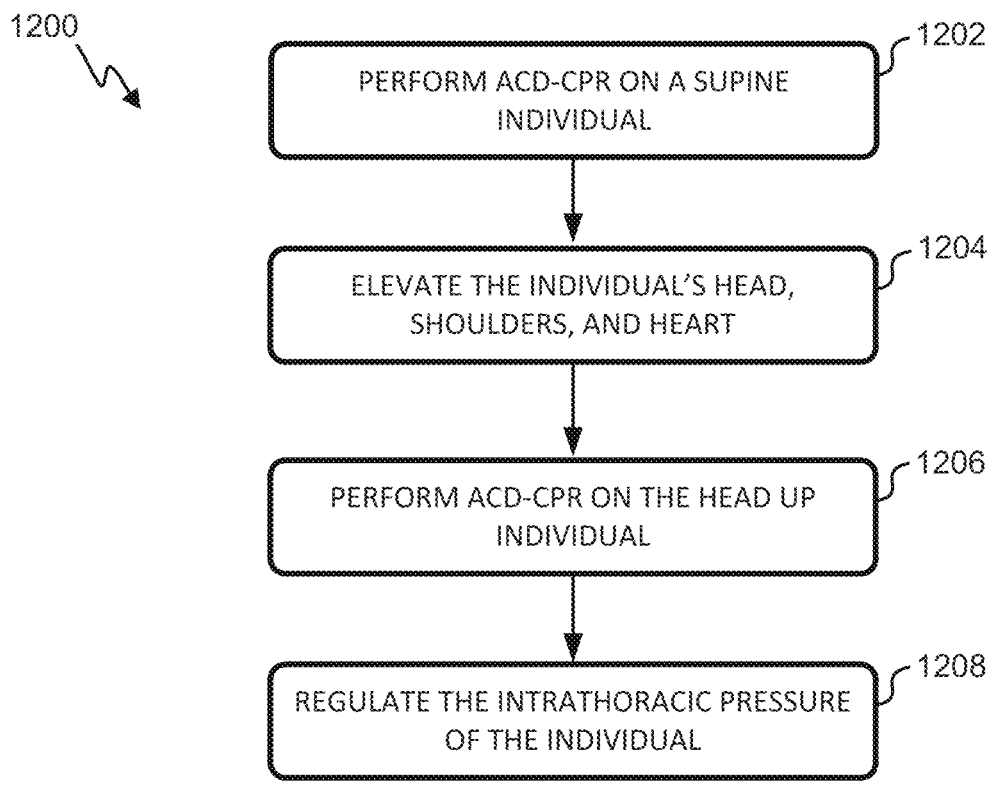
FIG. 12 is a flowchart of a process for treating brain edema according to embodiments.

The elevation devices described herein are used to reduce brain injury and brain swelling. As just one example, FIG. 12 depicts a process 1200 for reducing brain injury and brain swelling. Process 1200 may be performed using any of the elevation devices described herein. Process 1200 may begin by performing active compression decompression cardiopulmonary resuscitation (ACD-CPR) on an individual while the individual is in a supine position in general alignment with a horizontal plane at block 1202. At block 1204, the individual's head, shoulders, and heart may be elevated relative to the individual's lower body while the individual's lower body remains generally aligned with the horizontal plane. The head may be elevated to a height of between about 10 cm and 30 cm above the horizontal plane and the heart may be elevated to a height of between about 1 cm to 10 cm or 2 cm and 10 cm above the horizontal plane. The individual's chest may be compressed and actively decompressed while the individual's head, shoulders, and heart are elevated at block 1206. At block 1208, the intrathoracic pressure of the individual may be regulated using an impedance threshold device or other ITPR device both while the individual is in the supine position and while the individual's head, shoulders, and heart are elevated relative to the lower body, thereby reducing brain edema during CPR.

In some embodiments, head up CPR may be used in combination with a technique to reduce reperfusion injury. For example, prior to performing ACD-CPR on the individual, chest compressions may be performed on the individual for a period of between about 20-40 seconds. After performing the chest compressions on the individual and prior to performing ACD-CPR on the individual, halting the performance of chest compressions on the individual for a period of between about 20-40 seconds. By incorporating several of these rounds of supine chest compressions followed by halting the performance of chest compressions, reperfusion injury may be reduced. For example, the supine chest compressions followed by halting the performance of chest compressions on the individual may be repeated between 2-5 times prior to performing ACD-CPR to further reduce the risk of edema and brain swelling.

In some embodiments, upon stopping the performance of CPR, the individual may be maintained in a head up position with the individual's head, shoulders, and heart elevated as long as a sufficient mean arterial pressure (or blood pressure) is maintained to support blood flow to the brain in the head up position. For example, a sufficient mean arterial pressure to maintain adequate blood flow to the brain may be between about 60 mm Hg and 70 mm Hg. Such additional time in the head up position may further prevent brain edema and swelling.

The multiple methods and devices described above reduce brain swelling and elevated brain pressures during and after CPR. In the clinical setting of a patient with brain injury not in cardiac arrest, ICP is used to determine if a given therapy is effective in reducing brain swelling. For example, when the ICP is measured with an intracranial bolt, levels above 15 mmHg are generally considered dangerous and numerous approaches are used to treat such patients. These may include removing spinal fluid through the intracranial bolt, treatment with mannitol or hypertonic saline, hypothermia, hyperventilation to reduce CO2 in the blood which secondarily constricts of the arterial blood vessels to the brain (when brain autoregulation is intact), use of an intrathoracic pressure regulator to generate negative intrathoracic pressure following a positive pressure during mechanical ventilation, and elevation of the head. A reduction in ICP by even 2-4 mmHg is considered clinically important since the brain damage associated with elevated ICP is exponential due to the fact the brain is in a confined space. As the brain swelling rises there is no place for the brain tissue to go. In the most extreme cases the brain tissues herniates through the foramen magnum, the hole that connects the spinal column and cord to the brain.

In some embodiments, upon commencing CPR, therapeutic hypothermia and/or other cooling techniques may be performed to further reduce brain edema. For example, cooling of the individual may be done intravascularly and/or intraosseously with iced saline, or equivalent cooling through the nose, lungs, veins, and/or esophagus, with one of a variety of means and solutions that would work synergistically to reduce brain swelling and damage associated with cardiac arrest. This cooling may be performed during and/or after the performance and/or conclusion of CPR.

Example 1

The following experiments were performed to demonstrate that the methods and devices in this patent reduce brain edema during CPR and after resuscitation. The studies demonstrate that ICP, the measurement that is used clinically to determine whether or not the brain swelling, and cerebral oximetry, the non-invasive measure of brain oxygen, both improve clinically when the invention is used. The studies were performed as follows:

Female Yorkshire farm pigs weighing between 36-44 kg were fasted overnight after acclimatizing in the animal care facility for at least three days. Intramuscular ketamine (10 mL of 100 mg/mL) was administered in the holding pen. The animals were then transferred to the surgical suite where they were treated with inhaled isoflurane at 1% to 2.5% for anesthesia. The animals were then intubated with a 7.5 French endotracheal tube and ventilation was performed using a ventilator (Narkomed, North American Dräger, Telford, PA) with tidal volume 10 mL/kg. ETCO2 and oxygen saturation were recorded with a CO2SMO Plus® (Novametrix Systems, Wallingford, CT). The respiratory rate and FiO2 were adjusted to keep oxygen saturation above 92% and ETCO2 between 37 and 43 mmHg. Intravenous (IV) access with an 18-gauge catheter was obtained through a lateral ear vein. All animals received room air temperature normal saline bolus of 1000 ml during preparatory phase to maintain the mean right atrial pressure between 4 and 7 mmHg. Temperature was monitored with an esophageal probe. Temperature was maintained between 36.5 and 38.5° C. using a warming blanket, as needed. This Methodology was fully described in an article entitled, "Head and thorax elevation during active compression decompression cardiopulmonary resuscitation an impedance threshold device improves cerebral perfusion in a swine model of prolonged of cardiac arrest" by Johanna C Moore MD, Nicolas Segal MD PhD, Michael C Lick BA, Kenneth W Dodd MD, Bayert J Salverda BA, Mason B Hinke BA, Aaron E Robinson MD MPH, Guillaume Debaty MD PhD, and Keith G Lurie MD. to be published in Resuscitation in 2017. Intracranial pressure (ICP) was measured by creating a burr hole in the skull, and then insertion of a micromanometer-tipped catheter (Mikro-Tip Transducer, Millar Instruments, Houston, TX) catheter into the parietal lobe. All animals received a 100 units/kg bolus of heparin intravenously every hour.

Figure 13A:
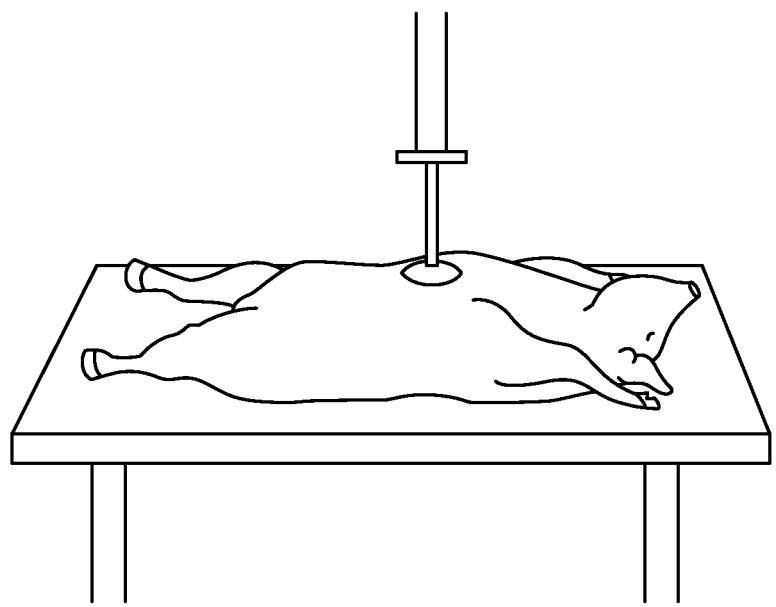
FIG. 13A is a schematic showing experimental protocol involving a supine specimen according to embodiments.
Figure 13B:
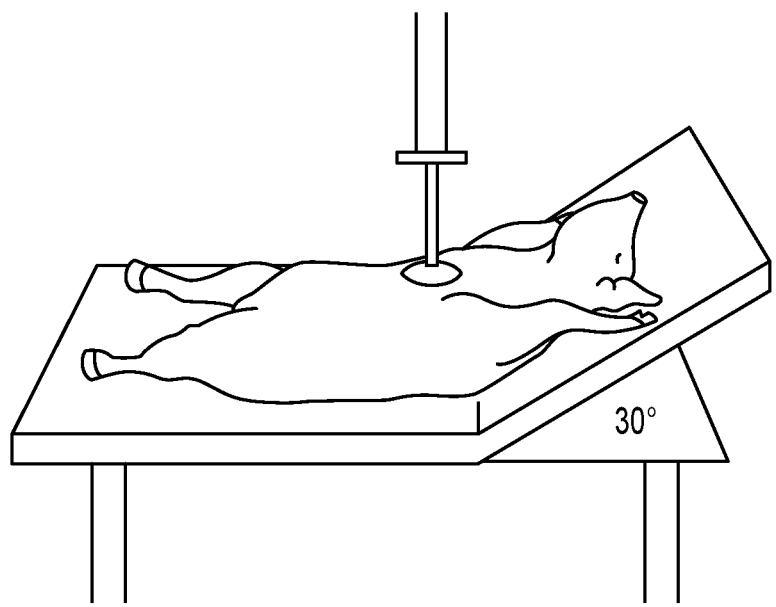
FIG. 13B is a schematic showing experimental protocol involving a head up specimen according to embodiments.

Data were recorded continuously using the BioPac computer system (BioPac; BioPac Systems Inc, Goleta CA). When the preparatory phase was complete and the animal was hemodynamically stable, isoflurane was discontinued, and after 3 minutes ventricular fibrillation (VF) was induced with delivery of direct electrical current from a pacing wire placed in the right ventricle. ACD CPR+ITD was performed with an automatic piston device (Pneumatic Compression Controller; Ambu International, Glostrup, Denmark) or with a LUCAS 2 device that pulls up only 3 pounds during the decompression phase (Physio-control, Redmond WA). ACD CPR was performed at a rate of 80 compressions/min, with a 50% duty cycle and depth of 22.5% of antero-posterior chest diameter, and the chest was pulled upwards after each compression with a suction cup on the skin at a decompression force of approximately 10 kg. The LUCAS 2 compressed at 100 compressions/min. An ITD, (ResQPOD-16, Zoll Medical, Minneapolis, MN) was placed at the end of the endotracheal tube in all studies. The HUP CPR device used in this study elevated just the head and shoulders and upper thorax 30° such that the heart and head heights were ~5 and ~25 cm above the horizontal plane, respectively, as shown in FIGS. 13A and 13B.

While transitioning from supine to the HUP CPR was performed in an uninterrupted manner. During CPR, positive pressure ventilation was delivered with oxygen, titrated to a SpO2 of ≥92%, with a tidal volume of 10 mL/kg. If the animal was noted to gasp during the resuscitation, time at first gasp was recorded. Succinylcholine was administered at a dose of 3 mg (0.075/kg) to inhibit gasping after the third gasp.

Regional Cerebral oximetry saturation (rSO2) was measured with an INVOS™ regional oximetry probe (Metronic-Covidien) applied to the pig's forehead. The approach uses near infrared spectroscopy to assess rSO2. Data were measured and recorded continuously as described above.

Experimental Protocol

After 8 minutes of untreated VF, ACD CPR+ITD or LUCAS 2+ITD was performed with a 30:2 compression:ventilation ratio, and positive pressure ventilation with room air was provided while all pigs were in the supine position (SUP) to simulate basic life support. After 2 minutes of CPR, animals were randomized either HUP CPR or SUP CPR and continuous asynchronous CPR+ITD was continued for 18 minutes with a 10:1 compression: ventilation ratio to simulate advanced life support. After 19 total minutes of CPR, 0.5 mg of adrenaline was administered intravenously followed by 25 mg of amiodarone. One minute later, pigs were defibrillated with up to three 200 J biphasic shocks (X-series, Zoll Medical, Chelmsford MA). Animals were monitored and were euthanized with an intravenous injection of KCl 20 minutes later.

ICP measurements were made from 3 sequential compression-decompression cycles between positive pressure breaths. These values were averaged for each of the compression-decompression cycle measurements for each time point in each animal study. Data are expressed as mean values.

Eighteen female pigs weighing 39.5±8.2 kg were randomized to ACD+ITD CPR in HUP (n=8) or SUP (n=10). ICP (mmHg) was measured in one pig from each group 15 minutes after successful resuscitation. Pigs treated with HUP ACD+ITD CPR had significantly lower intracranial pressure (ICP) after 15 minutes of ACD CPR+ITD and after 15 minutes return of spontaneous circulation (ROSC) and successful resuscitation versus SUP. These findings are shown in Table 1 below.

TABLE 1

| | ICP after 15 min. CPR | ICP post ROSC |
|---|---|---|
| CPR flat or supine | 17.7 | 22.6 |
| CPR Head and thorax elevated | 7.7 | 8.3 |

Two sets of studies with cerebral oximetry as the main endpoint were performed with the protocol described above to demonstrate the importance of the invention: one was performed using the LUCAS 2 that provides up to 3 pounds of upward force and the other with the ACD device that provides up to 20 pounds of decompression force.

Figure 14:
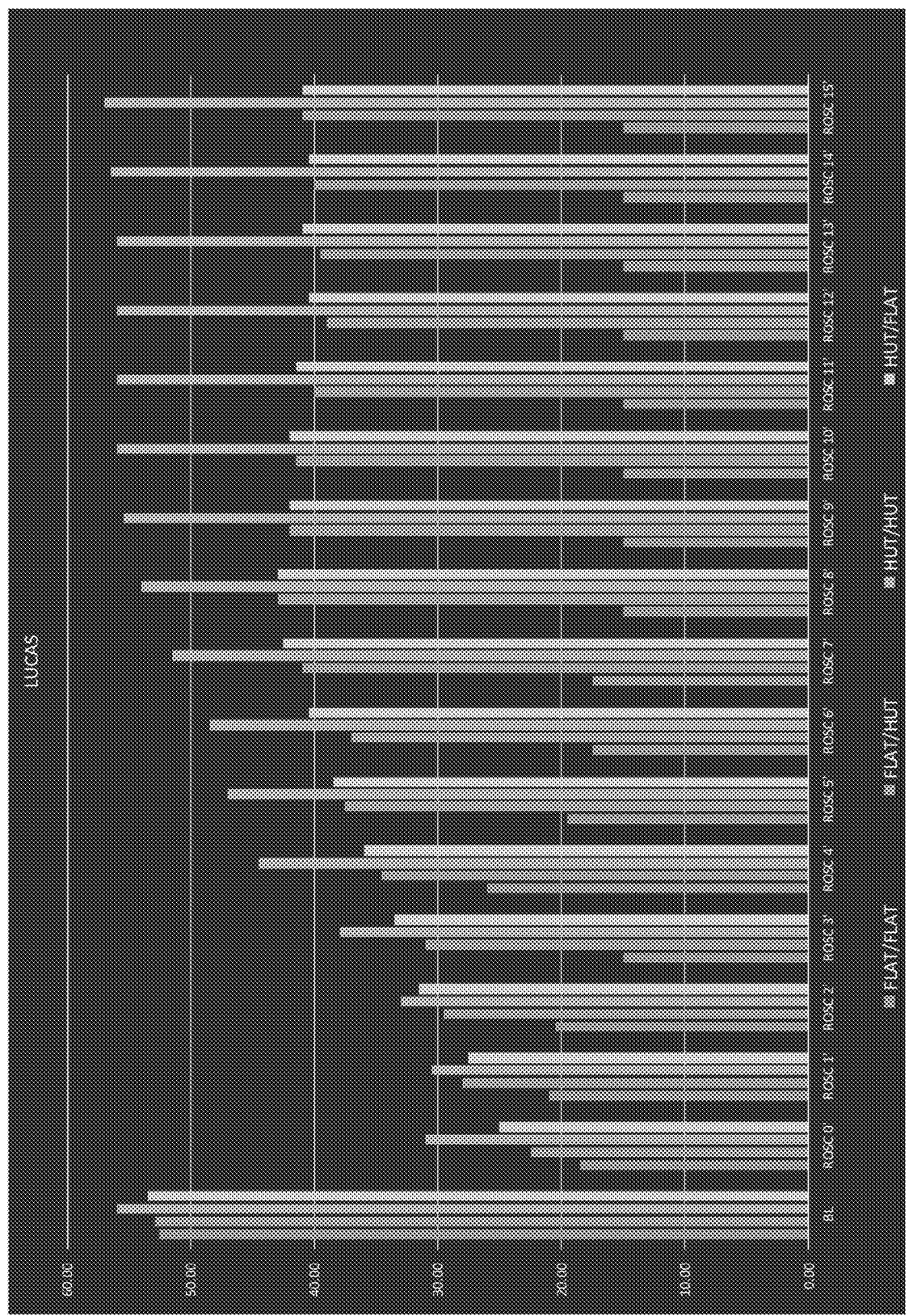
FIG. 14 is a chart showing cerebral oximetry saturation values during the performance of various types of CPR.
Figure 15:
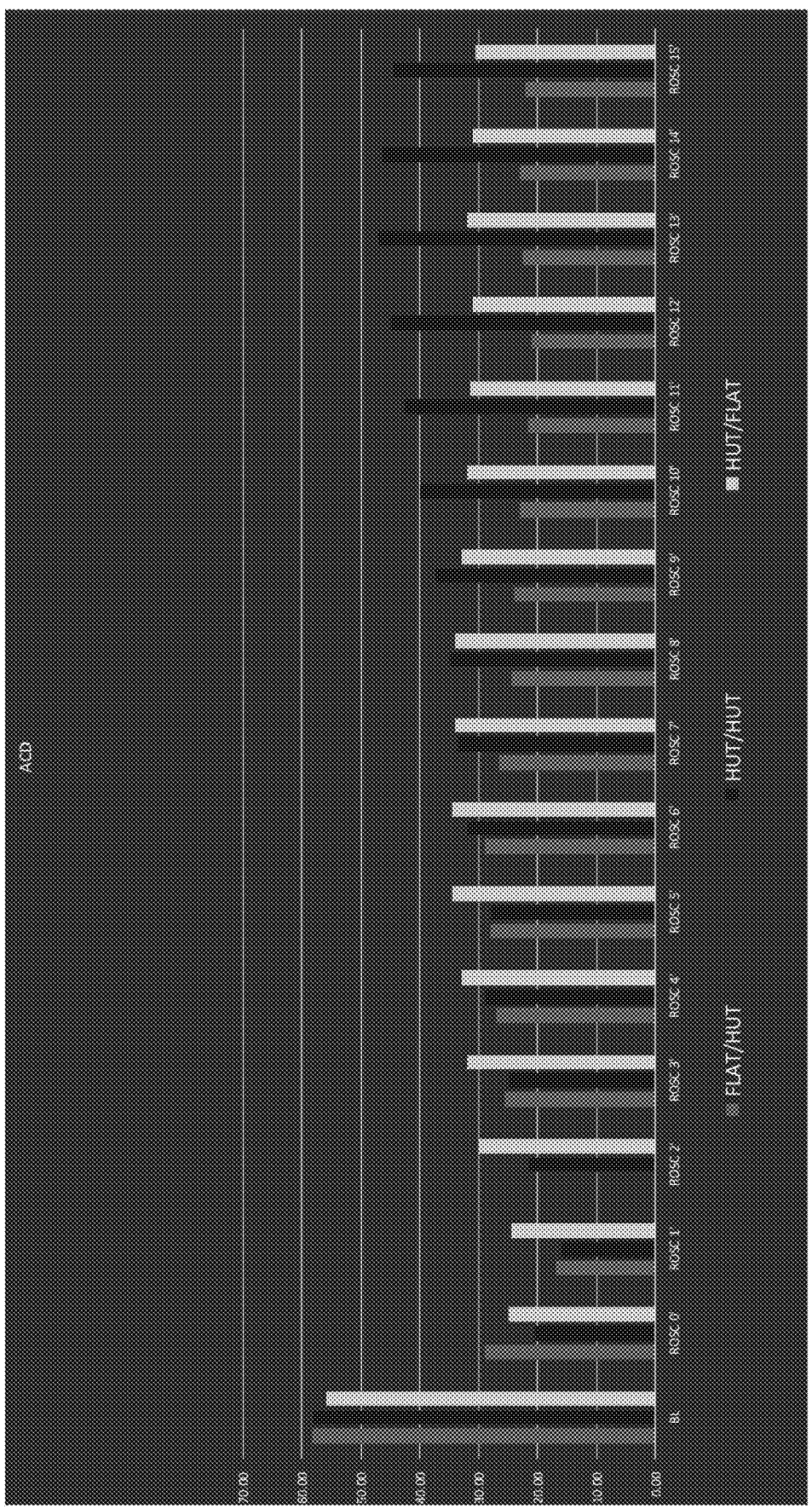
FIG. 15 is a chart showing cerebral oximetry saturation values during the performance of various types of CPR.

As shown in FIG. 14 with the LUCAS 2+ITD devices to provide CPR, the regional cerebral oximetry saturation values were highest with the head and thorax elevated during and after successful resuscitation with the lowest values when the head and thorax flat during CPR and after resuscitation. The unit of the Y-axis is regional cerebral oxygen saturation. Similar findings were observed with the ACD+ITD device that pulls upwards with 20 pounds of force during the active decompression phase as shown in FIG. 15. Taken together, these studies show that elevation of the head and thorax during and after CPR results in less brain edema, as measured by ICP, compared with pigs treated with CPR in the flat or horizontal plane. This is reflected in the normal ICP values when treatment is head and thorax elevation during CPR and after resuscitation. Similarly, cerebral oxygen saturation levels in pigs treated with elevation of the head and thorax during and after CPR were normal versus much lower when CPR was performed in the flat position and the pigs were kept flat after resuscitation.

With CPR performed with the body in the flat position, which is the standard of care throughout the world today, the ICP values during CPR and after resuscitation were nearly twice as high as those treated with head and thorax elevation. Similarly, the cerebral oxygen levels were normal after resuscitation with head and thorax elevation versus much lower in pigs treated with flat CPR.

These studies demonstrate the invention is effective to reduce brain edema as measured by ICP and cerebral oxygenation and also demonstrate that the head and thorax needed to be elevated during CPR and after resuscitation. Moreover, elevation of the head and thorax either just during CPR or just after resuscitation was not sufficient to restore normal brain oxygen levels or maximally reduce brain edema after resuscitation. It should be noted the invention reduces brain swelling after resuscitation, and it can be used synergistically with all other drugs, devices, methods, and techniques that are known to lower ICP and brain swelling to optimize long-term neurological outcomes after cardiac arrest. It should also be restated that the head and thorax can only be safely elevated after successful resuscitation to optimize the benefits of the invention if the mean arterial pressure is sufficient to pump blood up to the brain, typically it should be at least ~65 mmHg. This can be maintained, if necessary, with the aid of pharmacological agents such as adrenaline and the like.

Figure 16:
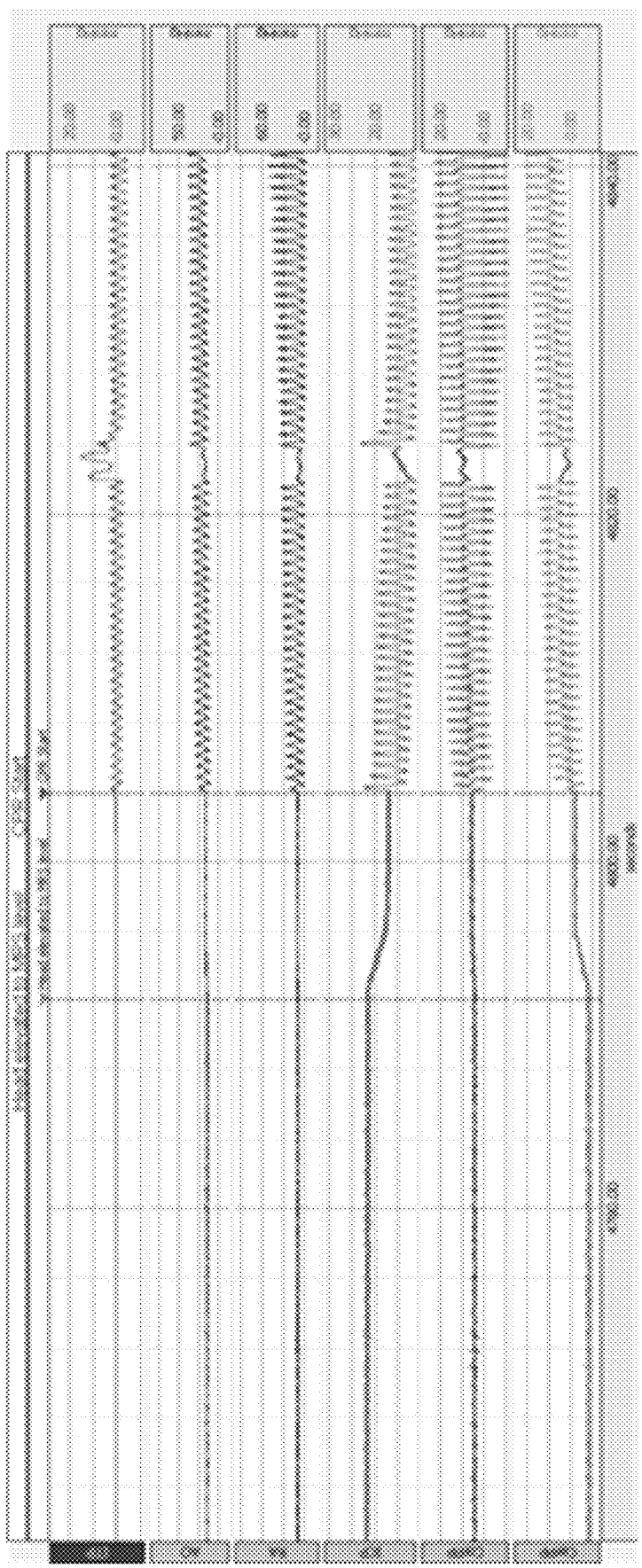
FIG. 16 is a chart showing various pressure values during the performance of head up CPR.

A reduction in intracranial pressure (ICP), recognizing that measurement of ICP is a means to directly assess the pressure within the brain that is also highly correlated with brain edema, occurs immediately upon elevation of the head during cardiac arrest. This new observation is shown in FIG. 16. In this figure, all pressures are measured in mmHg. The top pressure tracing, labeled ITP, is the intrathoracic pressure, the second pressure tracing labeled AO is aortic pressure, the third RA is right atrial pressure, the fourth ICP is intracranial pressure, the fifth is the calculated coronary perfusion pressure (AO-RA) and the sixth is the calculated cerebral perfusion pressure (Ao-ICP).

What is shown in this representative tracing from pigs in cardiac arrest as described above, is that after a period of untreated cardiac arrest, in this case 8 minutes, elevation of the head by 10 cm while this pig is being placed from the horizontal flat position onto a head up CPR device as shown in FIG. 16, (at the time point of 4795 seconds on the graph), there is an immediate reduction in ICP by 5 mmHg whereas the aortic pressure remains constant. The results of the effect of gravity are shown: ICP falls and the cerebral perfusion pressure rises, simply with elevation of the head and thorax onto the elevated CPR device shown in FIG. 6. By reducing ICP, even before starting CPR, the likelihood of brain damage and brain edema is reduced.

In general brain edema can result from prolonged periods of no flow and trauma to the brain. The prolonged periods of reduced blood flow to the brain associated with CPR performed on the body when in the flat or horizontal plane combined with the concussive forces from the arterial and venous pressure waves that bombard the brain with each chest compression result severe brain edema in ⅓ to ⅔ of patients who arrive at the hospital alive. Such patients rarely, if ever, wake up after a cardiac arrest. In the US, the national average for neurologically-intact survival in <10% and has remain that way for decades. By contrast, elevation of the head and thorax, as described within this application, results in an immediate reduction in ICP, even before starting CPR as shown in FIG. 16. Head up applications are also described in U.S. application Ser. No. 15/986,466, U.S. application Ser. No. 15/601,494, U.S. application Ser. No. 15/285,063, U.S. application Ser. No. 15/160,492, U.S. application Ser. No. 15/133,967, U.S. application Ser. No. 14/996,147, U.S. application Ser. No. 14/935,262, U.S. application Ser. No. 14/677,562, 2015, U.S. Provisional Application No. 61/941,670, U.S. Provisional Application No. 62/000,836, and U.S. Provisional Application No. 62/087,717, and U.S. Provisional Application No. 62/242,655, the complete disclosures of which are hereby incorporated by reference for all intents and purposes), the entire contents of which are hereby incorporated by reference, These applications demonstrate that elevation of the head and heart during CPR result in a marked reduction in ICP and a marked increase in cerebral and coronary perfusion and perfusion pressures. By reducing the overall ischemic burden (lack of blood flow to the brain and heart) with head and thorax elevation, and reducing the trauma from the 'concussion with every compression', the likelihood of brain edema is reduced. This is also shown by the lower ICP values in the pigs treated with head up CPR compared with flat CPR during and after resuscitation (as shown in Table 1 above).

Example 2

Data was analyzed from a Head Up CPR Registry with 227 patients from 6 US Sites where the Head Up CPR method was performed. The data was collected upon approval from the Western Institutional Review Board (IRB), a central IRB. This data demonstrated that the rapid performance of Head Up CPR resulted in increased neurologically intact survival rates compared with conventional flat CPR controls with the same time to CPR from 3 multi-site national NIH funded CPR studies where 911 to EMS CPR start time was recorded (NIH-funded Resuscitation Outcomes Consortium PRIMED and ALPS and the ResQTrial).

The case-controlled or propensity matched analysis controlled for age, sex, witnessed status, and if bystander CPR was performed. The data was broken down into rapid start of Head Up CPR versus delay start. The statistical analysis is summarized in Table 2 as follows:

TABLE 2

Comparison of favorable neurological outcome at hospital discharge according to standard versus head-up cardiopulmonary resuscitation stratified by time from dispatch to first responder CPR for patients enrolled in four primary studies.

| Alive at hospital discharge | Standard CPR, n (%) | Head-up CPR, n (%) | Odds ratio (95% Confidence Interval) |
|---|---|---|---|
| Time from dispatch to first response CPR ≤ 10 min | | | |
| Unadjusted | 545/4482 (12) | 10/67 (15) | 1.27 (0.64-2.50) |
| Adjusted | | | 2.28 (0.98-5.34) |
| Propensity-matched | 23/331 (7.0) | 10/67 (15) | 2.35 (1.06-5.20) |
| Time from dispatch to first response CPR ≥ 11 min | | | |
| Unadjusted | 65/827 (7.9) | 3/160 (1.9) | 0.22 (0.07-0.72) |
| Adjusted | | | 1.04 (0.26-4.10) |
| Propensity-matched | 7/145 (4.8) | 3/58 (5.2) | 1.08 (0.27-4.31) |

The data above shows that with propensity matching, 15% of patients in the Head Up group versus 7% of patient in the control group survived with good brain function. The likelihood of this occurring, or the odd ratio, was 2.35 times more with Head-Up CPR with 95% confidence intervals of 1.06-5.20. Thus, the likelihood of this being correct is >95%. This registry data shows that rapid application and the performance of Head up CPR (with a 911 call to start of Head-up CPR of less than or equal to 10 minutes by first responder) may more than double neurologically-intact survival rates in cardiac arrest patients compared to standard/flat CPR. Patients in this registry study received manual CPR initially and then active compression decompression CPR with an impedance threshold device.

What is claimed is:

1. A method to improve neurologically-intact survival rates after cardiac arrest, comprising:
    performing CPR on an individual in cardiac arrest while the individual is in a supine position in general alignment with a horizontal plane;
    elevating the individual's head, shoulders, and heart relative to the individual's lower body while the individual's lower body remains generally aligned with the horizontal plane to cause blood to actively drain venous blood from the individual's brain to reduce intracranial pressure;
    performing chest compressions on the individual and actively decompressing the individual's chest while the individual's head, shoulders, and heart are elevated; and
    after a successful resuscitation and CPR is no longer needed, lowering the individual's head, shoulders, and heart over a period of between about 1 and 10 seconds upon detecting that a sufficient mean arterial pressure is no longer maintained.

2. The method to improve neurologically-intact survival rates after cardiac arrest of claim 1, wherein:
    the head is elevated to a height of between about 10 cm and 30 cm above the horizontal plane and the heart is elevated to a height of between about 2 cm and 10 cm above the horizontal plane.

3. The method to improve neurologically-intact survival rates after cardiac arrest of claim 1, further comprising:
    regulating an intrathoracic pressure of the individual while the individual's head, shoulders, and heart are elevated relative to the lower body.

4. The method to improve neurologically-intact survival rates after cardiac arrest of claim 1, wherein:
    elevating the individual's head, shoulders, and heart relative to the individual's lower body comprises elevating the individual's head, shoulders, and heart to an intermediate elevation position; and
    the method further comprises:
        elevating the individual's head, shoulders, and heart a second time to a final elevation position; and
        performing chest compressions on the individual and actively decompressing the individual's chest while the individual's head, shoulders, and heart are at the final elevation position.

5. The method to improve neurologically-intact survival rates after cardiac arrest of claim 4, wherein:
    the individual's head, shoulders, and heart are elevated to the intermediate elevation position at a rate that is slower than a rate at which the individual's head, shoulders, and heart are elevated to the final elevation position.

6. The method to improve neurologically-intact survival rates after cardiac arrest of claim 1, wherein:
when elevated, a vertical distance between the individual's head and heart is between about 5 cm and 20 cm.

7. A method to improve neurologically-intact survival rates after cardiac arrest, comprising:
performing active compression decompression cardiopulmonary resuscitation (ACD-CPR) on an individual in cardiac arrest while the individual's heart is at a position of between about 0 cm to 8 cm above horizontal and the individual's head is at a position of between about 0 and 15 cm above horizontal;
elevating the individual's head, shoulders, and heart relative to the individual's lower body while the individual's lower body remains generally aligned with a horizontal plane to cause blood to actively drain venous blood from the individual's brain to reduce intracranial pressure, wherein the head is elevated to a height of between about 10 cm and 30 cm above the horizontal plane and the heart is elevated to a height of between about 2 cm and 10 cm above the horizontal plane;
performing chest compressions on the individual and actively decompressing the individual's chest while the individual's head, shoulders, and heart are elevated; and
lowering the individual's head, shoulders, and heart over a period of between about 1 and 10 seconds upon detection of a stable heart rhythm.

8. The method to improve neurologically-intact survival rates after cardiac arrest of claim 7, wherein:
regulating an intrathoracic pressure of the individual using an intrathoracic pressure regulation device while the individual's head, shoulders, and heart are elevated relative to the lower body.

9. The method to improve neurologically-intact survival rates after cardiac arrest of claim 7, wherein:
upon stopping the performance of CPR, maintaining the individual in a head up position with the individual's head, shoulders, and heart elevated as long as a sufficient mean arterial pressure is maintained to support blood flow to the brain in the head up position.

10. The method to improve neurologically-intact survival rates after cardiac arrest of claim 9, wherein:
the sufficient mean arterial pressure is between about 60 mm Hg and 70 mm Hg.

11. The method to improve neurologically-intact survival rates after cardiac arrest of claim 7, further comprising:
detecting a stable heart rhythm; and
halting the performance of chest compressions based on the detection of the stable heart rhythm.

12. The method to improve neurologically-intact survival rates after cardiac arrest of claim 11, wherein:
the stable heart rhythm is detected using an electrocardiogram.

13. A method to improve neurologically-intact survival rates after cardiac arrest, comprising:
performing cardiopulmonary resuscitation (CPR) on an individual in cardiac arrest while the individual's heart is at a position of between about 0 cm to 8 cm above horizontal and the individual's head is at a position of between about 0 and 15 cm above horizontal;
elevating the individual's head, shoulders, and heart relative to the individual's lower body while the individual's lower body remains generally aligned with a horizontal plane to cause blood to actively drain venous blood from the individual's brain to reduce intracranial pressure, wherein the head is elevated to a height of between about 10 cm and 30 cm above the horizontal plane and the heart is elevated to a height of between about 2 cm and 10 cm above the horizontal plane;
delivering chest compressions to the individual's chest using a CPR assist device while the individual's head, shoulders, and heart are elevated;
upon stopping the performance of CPR, maintaining the individual in a head up position with the individual's head, shoulders, and heart elevated as long as a sufficient mean arterial pressure is maintained to support blood flow to the brain in the head up position; and
lowering the individual's head, shoulders, and heart over a period of between about 1 and 10 seconds upon detecting that the sufficient mean arterial pressure is no longer maintained.

14. The method to improve neurologically-intact survival rates after cardiac arrest of claim 13, further comprising:
regulating an intrathoracic pressure of the individual using an intrathoracic pressure regulation device while the individual's head, shoulders, and heart are elevated relative to the lower body.

15. The method to improve neurologically-intact survival rates after cardiac arrest of claim 13, wherein:
the individual's head, shoulders, and heart are elevated within 10 minutes of onset of cardiac arrest.

16. The method to improve neurologically-intact survival rates after cardiac arrest of claim 13, further comprising:
therapeutically cooling the individual during the delivery of chest compressions.

17. The method to improve neurologically-intact survival rates after cardiac arrest of claim 13, further comprising:
therapeutically cooling the individual after halting the delivery of chest compressions.

18. An after-cardiac arrest brain trauma reduction system, comprising:
a base;
a support surface that is movably coupled with the base;
a cardiopulmonary resuscitation (CPR) assist device that is positionable in alignment with the heart and thorax of the individual;
one or more processors; and
a memory having instructions stored thereon that, when executed, cause the one or more processors to:
send instructions to raise the support surface to elevate the head, shoulders, and heart of an individual such that the heart is elevated between about 2 and 10 cm above the horizontal plane and the head is elevated between about 5 and 30 cm above the horizontal plane;
cause the CPR assist device to repeatedly compress the individual's chest while the support surface is raised; and
send instructions to halt chest compressions and lower the individual's head, shoulders, and heart over a period of between about 1 and 10 seconds upon detecting that a sufficient mean arterial pressure is no longer maintained.

* * * * *